US009840719B2

(12) United States Patent
High et al.

(10) Patent No.: US 9,840,719 B2
(45) Date of Patent: Dec. 12, 2017

(54) VARIANT AAV AND COMPOSITIONS, METHODS AND USES FOR GENE TRANSFER TO CELLS, ORGANS AND TISSUES

(71) Applicant: The Children's Hospital of Philadelphia, Philadelphia, PA (US)

(72) Inventors: Katherine High, Merion, PA (US); Mustafa Yazicioglu, Philadelphia, PA (US); Xavier Anguela, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 194 days.

(21) Appl. No.: 14/338,200

(22) Filed: Jul. 22, 2014

(65) Prior Publication Data

US 2015/0023924 A1 Jan. 22, 2015

Related U.S. Application Data

(60) Provisional application No. 61/985,365, filed on Apr. 28, 2014, provisional application No. 61/857,161, filed on Jul. 22, 2013.

(51) Int. Cl.
| | | |
|---|---|---|
| *C12N 15/86* | (2006.01) | |
| *C07K 14/005* | (2006.01) | |
| *C12N 9/64* | (2006.01) | |
| *A61K 48/00* | (2006.01) | |
| *A61K 38/00* | (2006.01) | |

(52) U.S. Cl.
CPC ........... *C12N 15/86* (2013.01); *C07K 14/005* (2013.01); *C12N 9/6408* (2013.01); *C12Y 304/21022* (2013.01); *A61K 38/00* (2013.01); *A61K 48/0058* (2013.01); *C12N 2750/14122* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | |
|---|---|---|
| 6,156,303 A | 12/2000 | Russell et al. |
| 6,468,524 B1 | 10/2002 | Chiorini et al. |
| 6,531,298 B2 | 3/2003 | Stafford et al. |
| 2008/0044386 A1 | 2/2008 | Ji et al. |
| 2008/0220015 A1 | 9/2008 | Abina |
| 2009/0197338 A1 | 8/2009 | Vandenberghe et al. |
| 2009/0317417 A1 | 12/2009 | Vandenberghe et al. |
| 2010/0286242 A1 | 11/2010 | Bohn et al. |
| 2011/0263027 A1 | 10/2011 | Gao et al. |
| 2014/0271550 A1 | 9/2014 | Rabinowitz et al. |
| 2014/0323956 A1 | 10/2014 | Mendell et al. |

| | | |
|---|---|---|
| 2015/0273082 A1 | 10/2015 | Nathwani et al. |
| 2016/0201088 A1* | 7/2016 | Gao ............... C07K 14/755 424/93.2 |
| 2016/0375110 A1 | 12/2016 | High et al. |

FOREIGN PATENT DOCUMENTS

| | | |
|---|---|---|
| WO | 2004027019 A2 | 4/2004 |
| WO | 2007120542 A2 | 10/2007 |
| WO | 2011133890 A1 | 10/2011 |
| WO | 2011133933 A2 | 10/2011 |
| WO | 2013078316 A1 | 5/2013 |
| WO | 2013078400 A1 | 5/2013 |
| WO | 2013123457 A1 | 8/2013 |
| WO | 2013123503 A1 | 8/2013 |
| WO | 2013/158879 A1 | 10/2013 |

OTHER PUBLICATIONS

Gao et al., J. Virol., 2004, 78: 6381-6388.*
Sequence alignment, 2016.*
PCT International Application No. PCT/US2014/047670, International Search Report and Written Opinion, dated Jan. 30, 2015.
Martin et al., Overexpression of Galgt2 in skeletal muscle prevents injury resulting from eccentric contractions in both mdx and wild-type mice, Am. J. Physiol. Cell Physiol., 2009, 296:C476-88.
Rodino-Klapac et al., A translational approach for limb vascular delivery of the micro-dystrophin gene without high volume or high pressure for treatment of Duchenne muscular dystrophy, J. Transl. Med., 2007, 5(45):1-11.
Gao, G., et al., Glades of Adeno-Associated Viruses are Widely Disseminated in Human Tissues, Journal of Virology, 2004, 78(12):6381-6388.
Herzog, R.W., et al., Long-Term Correction of Canine Hemophilia B by Gene Transfer of Blood Coagulation Factor IX Mediated by Adeno-Associated Viral Vector, Nature Medicine, 1999 (5(1):56-63.
Chirmule, N. et al., Humoral Immunity to Adeno-Associated Virus Type 2 Vectors Following Administration to Murine and Nonhuman Primate Muscle, Journal of Virology, 2000, 74(5):2420-2425.
Katz et al., Cardiac Gene Therapy: Optimization of Gene Delivery Techniques In Vivo, Human Gene Therapy, 2010, 21:371-380.
Daya et al., Gene Therapy Using Adeno-Associated Virus Vectors, Clinical Microbiology Reviews, 2008, pp. 583-593.
Fumoto et al., Targeted Gene Delivery: Importance of Administration Routes, Intech, 2013, pp. 3-31.
Wright, J.F. et al., Manufacturing and Characterizing AAV-Based Vectors for Use in Clinical Studies, Gene Therapy, 2008, 15:840-848.

(Continued)

*Primary Examiner* — Ileana Popa
(74) *Attorney, Agent, or Firm* — Pillsbury Winthrop Shaw Pittman LLP

(57) ABSTRACT

The invention relates to adeno-associated virus (AAV) serotype AAV-Rh74 and related AAV vectors, and AAV-Rh74 and related AAV vector mediated gene transfer methods and uses. In particular, AAV-Rh74 and related AAV vectors target polynucleotides to cells, tissues or organs for expression (transcription) of genes encoding therapeutic proteins and peptides, and polynucleotides that function as or are transcribed into inhibitory nucleic acid sequences.

21 Claims, 9 Drawing Sheets
(2 of 9 Drawing Sheet(s) Filed in Color)

(56) References Cited

OTHER PUBLICATIONS

Guo et al., Protein Tolerance to Random Amino Acid Change, PNAS, 2004, 101(25):9205-9210.

Lesk et al., Prediction of Protein Function from Protein Sequence and Structure, p. 27 and 28, downloaded Sep. 16, 2007.

Mingozzi, F. et al., Overcoming Preexisting Humoral Immunity to AAV Using Capsid Decoys, Science Translational Medicine, 2013, 5(192-196):122-130.

Qu, G., et al., Separation of Adeno-Associated Virus Type 2 Empty Particles from Genome Containing Vectors by Anion-Exchange Column Chromatography, Journal of Virological Methods, 2007, 140:183-192.

Scallan et al., Human Immunoglobulin Inhibits Liver Transduction by AAV Vectors at Low AAV2 Neutralizing Titers in SCID Mice, Blood, 2005, 107:1810-1817.

Urabe et al., Removal of Empty Capsids from Type 1 Adeno-Associated Virus Vector Stocks by Anion-Exchange Chromatography Potentiates Transgene Expression, Molecular Therapy, 2006, 13(4):823-28.

Kay et al., Evidence for Gene Transfer and Expression of Factor IX in Haemophilia B Patients Treated with an AAV Vector, Nature Genetics, 2000, 24(3):257-61.

Halbert, C.L., et al., Adeno-associated virus type 6 (AAV6) vectors mediate efficient transduction of airway epithelial cells in mouse lungs compared to that of AAV2 vectors, Journal of Virology, 2001, 75(14):6615-6624.

Hodges, B.L. et al., Long-term transgene expression from plasmid DNA gene therapy vectors is negatively affected by CpG dinucleotides, Molecular Therapy, 2004, 10(2):269-278.

McIntosh, J., et al., Therapeutic levels of FVIII following a since peripheral vein administration of rAAV vector encoding a novel human factor VIII variant, Blood, 2013, 121(17):3335-3344.

NCBI, GenBank accession No. AAS99242.1 (Jun. 24, 2004).

Rogers, G.L. et al., Role of the vector genome and underlying factor IX mutation in immune responses to AAV gene therapy for hemophilia B., Journal of Translational Medicine, 2014, 12(1):e25 (inner pp. 1-10).

Yew, N.S., et al., CpG-Depleted Plasmid DNA Vectors with Enhanced Safety and Long-Term Gene Expression in vivo, Molecular Therapy, 2002, 5(6):731-738.

Nair, A.R., et al., Effect of different UCOE-promoter combinations in creation of engineered cell lines for the production of Factor VIII, BMC Research Notes, 2011, 4:178.

NCBI, GenBank accession No. EU159410.1 (Jul. 23, 2009) See the whole sequence.

NCBI, GenBank accession No. NM_000132.3 (Sep. 11, 2015) See the who sequence.

Ketterling, R.P., et al., The Rates of G:C->C:G Transversions at CpG Dinucleotides in the Human Factgor IX Gene, Am. J. Hum. Genet., 1994, 54:831-835.

Simioni, P., et al., X-Linked Thrombophilia with a Mutant Factor IX (Factor IX Padua), The New England Journal of Medicine, 2009, 361(17):1671-1675.

* cited by examiner

Figure 3A (SEQ ID NOs:1-5)

Rh74 VP1 Amino Acid (SEQ ID NO:1):
MAADGYLPDWLEDNLSEGIREWWDLKPGAPKPKANQQKQDNGRGLVLPGYKYLGPFNGLDKG
EPVNAADAAALEHDKAYDQQLQAGDNPYLRYNHADAEFQERLQEDTSFGGNLGRAVFQAKKRV
LEPLGLVESPVKTAPGKKRPVEPSPQRSPDSSTGIGKKGQQPAKKRLNFGQTGDSESVPDPQPIGE
PPAGPSGLGSGTMAAGGGAPMADNNEGADGVGSSSGNWHCDSTWLGDRVITTSTRTWALPTYN
NHLYKQISNGTSGGSTNDNTYFGYSTPWGYFDFNRFHCHFSPRDWQRLINNNWGFRPKRLNFK
LFNIQVKEVTQNEGTKTIANNLTSTIQVFTDSEYQLPYVLGSAHQGCLPPFPADVFMIPQYGYLTL
NNGSQAVGRSSFYCLEYFPSQMLRTGNNFEFSYNFEDVPFHSSYAHSQSLDRLMNPLIDQYLYYLS
RTQSTGGTAGTQQLLFSQAGPNNMSAQAKNWLPGPCYRQQRVSTTLSQNNNSNFAWTGATKYH
LNGRDSLVNPGVAMATHKDDEERFFPSSGVLMFGKQGAGKDNVDYSSVMLTSEEEIKTTNPVAT
EQYGVVADNLQQQNAAPIVGAVNSQGALPGMVWQNRDVYLQGPIWAKIPHTDGNFHPSPLMGG
FGLKHPPPQILIKNTPVPADPPTTFNQAKLASFITQYSTGQVSVEIEWELQKENSKRWNPEIQYTS
NYYKSTNVDFAVNTEGTYSEPRPIGTRYLTRNL.

Rh74 VP1 DNA (SEQ ID NO:2):
ATGGCTGCCGATGGTTATCTTCCAGATTGGCTCGAGGACAACCTCTCTGAGGGCATTCGCGAGTG
GTGGGACCTGAAACCTGGAGCCCCGAAACCCAAAGCCAACCAGCAAAAGCAGGACAACGGCCGG
GGTCTGGTGCTTCCTGGCTACAAGTACCTCGGACCCTTCAACGGACTCGACAAGGGGGAGCCCGT
CAACGCGGCGGACGCAGCGGCCCTCGAGCACGACAAGGCCTACGACCAGCAGCTCCAAGCGGGTG
ACAATCCGTACCTGCGGTATAATCACGCCGACGCCGAGTTTCAGGAGCGTCTGCAAGAAGATAC
GTCTTTTGGGGGCAACCTCGGGCGCGCAGTCTTCCAGGCCAAAAAGCGGGTTCTCGAACCTCTGG
GCCTGGTTGAATCGCCGGTTAAGACGGCTCCTGGAAAGAAGAGACCGGTAGAGCCATCACCCCA
GCGCTCTCCAGACTCCTCTACGGGCATCGGCAAGAAGGCCAGCAGCCCGCAAAAAAGAGACTCA
ATTTTGGGCAGACTGGCGACTCAGAGTCAGTCCCCGACCCTCAACCAATCGGAGAACCACCAGCA
GGCCCCTCTGGTCTGGGATCTGGTACAATGGCTGCAGGCGGTGGCGCTCCAATGGCAGACAATAA
CGAAGGCGCCGACGGAGTGGGTAGTTCCTCAGGAAATTGGCATTGCGATTCCACATGGCTGGGC
GACAGAGTCATCACCACCAGCACCCGCACCTGGGCCCTGCCCACCTACAACAACCACCTCTACAA
GCAAATCTCCAACGGGACCTCGGGAGGAAGCACCAACGACAACACCTACTTCGGCTACAGCACCC
CCTGGGGGTATTTTGACTTCAACAGATTCCACTGCCACTTTTCACCACGTGACTGGCAGCGACTC
ATCAACAACAACTGGGGATTCCGGCCCAAGAGGCTCAACTTCAAGCTCTTCAACATCCAAGTCAA
GGAGGTCACGCAGAATGAAGGCACCAAGACCATCGCCAATAACCTTACCAGCACGATTCAGGTC
TTTACGGACTCGGAATACCAGCTCCCGTACGTGCTCGGCTCGGCGCACCAGGGCTGCCTGCCTCC
GTTCCCGGCGGACGTCTTCATGATTCCTCAGTACGGGTACCTGACTCTGAACAATGGCAGTCAGG
CTGTGGGCCGGTCGTCCTTCTACTGCCTGGAGTACTTTCCTTCTCAAATGCTGAGAACGGGCAAC
AACTTTGAATTCAGCTACAACTTCGAGGACGTGCCCTTCCACAGCAGCTACGCGCACAGCCAGAG
CCTGGACCGGCTGATGAACCCTCTCATCGACCAGTACTTGTACTACCTGTCCCGGACTCAAAGCA
CGGGCGGTACTGCAGGAACTCAGCAGTTGCTATTTTCTCAGGCCGGGCCTAACAACATGTCGGCT
CAGGCCAAGAACTGGCTACCCGGTCCCTGCTACCGGCAGCAACGCGTCTCCACGACACTGTCGCA
GAACAACAACAGCAACTTTGCCTGGACGGGTGCCACCAAGTATCATCTGAATGGCAGAGACTCT
CTGGTGAATCCTGGCGTTGCCATGGCTACCCACAAGGACGACGAAGAGCGATTTTTTCCATCCAG
CGGAGTCTTAATGTTTGGGAAACAGGGAGCTGGAAAAGACAACGTGGACTATAGCAGCGTGATG
CTAACCAGCGAGGAAGAAATAAAGACCACCAACCCAGTGGCCACAGAACAGTACGGCGTGGTGG
CCGATAACCTGCAACAGCAAAACGCCGCTCCTATTGTAGGGGCCGTCAATAGTCAAGGAGCCTTA
CCTGGCATGGTGTGGCAGAACCGGGACGTGTACCTGCAGGGTCCCATCTGGGCCAAGATTCCTCA
TACGGACGGCAACTTTCATCCCTCGCCGCTGATGGGAGGCTTTGGACTGAAGCATCCGCCTCCTC
AGATCCTGATTAAAAACACACCTGTTCCCGCGGATCCTCCGACCACCTTCAATCAGGCCAAGCTG
GCTTCTTTCATCACGCAGTACAGTACCGGCCAGGTCAGCGTGGAGATCGAGTGGGAGCTGCAGA
AGGAGAACAGCAAACGCTGGAACCCAGAGATTCAGTACACTTCCAACTACTACAAATCTACAAA

Figure 3B

TGTGGACTTTGCTGTCAATACTGAGGGTACTTATTCCGAGCCTCGCCCCATTGGCACCCGTTACC
TCACCCGTAATCTGTAA

Rh74 VP2 Amino Acid (SEQ ID NO:3):

TAPGKKRPVEPSPQRSPDSSTGIGKKGQQPAKKRLNFGQTGDSESVPDPQPIGEPPAGPSGLGSGTMAAGGGAPMAD
NNEGADGVGSSSGNWHCDSTWLGDRVITTSTRTWALPTYNNHLYKQISNGTSGGSTNDNTYFGYSTPWGYFDFNRFH
CHFSPRDWQRLINNNWGFRPKRLNFKLFNIQVKEVTQNEGTKTIANNLTSTIQVFTDSEYQLPYVLGSAHQGCLPPF
PADVFMIPQYGYLTLNNGSQAVGRSSFYCLEYFPSQMLRTGNNFEFSYNFEDVPFHSSYAHSQSLDRLMNPLIDQYL
YYLSRTQSTGGTAGTQQLLFSQAGPNNMSAQAKNWLPGPCYRQQRVSTTLSQNNNSNFAWTGATKYHLNGRDSLVNP
GVAMATHKDDEERFFPSSGVLMFGKQGAGKDNVDYSSVMLTSEEEIKTTNPVATEQYGVVADNLQQQNAAPIVGAVN
SQGALPGMVWQNRDVYLQGPIWAKIPHTDGNFHPSPLMGGFGLKHPPPQILIKNTPVPADPPTTFNQAKLASFITQY
STGQVSVEIEWELQKENSKRWNPEIQYTSNYYKSTNVDFAVNTEGTYSEPRPIGTRYLTRNL

Rh74 VP3 Amino Acid (SEQ ID NO:4):

MAAGGGAPMADNNEGADGVGSSSGNWHCDSTWLGDRVITTSTRTWALPTYNNHLYKQISNGTSGGSTNDNTYFGYST
PWGYFDFNRFHCHFSPRDWQRLINNNWGFRPKRLNFKLFNIQVKEVTQNEGTKTIANNLTSTIQVFTDSEYQLPYVL
GSAHQGCLPPFPADVFMIPQYGYLTLNNGSQAVGRSSFYCLEYFPSQMLRTGNNFEFSYNFEDVPFHSSYAHSQSLD
RLMNPLIDQYLYYLSRTQSTGGTAGTQQLLFSQAGPNNMSAQAKNWLPGPCYRQQRVSTTLSQNNNSNFAWTGATKY
HLNGRDSLVNPGVAMATHKDDEERFFPSSGVLMFGKQGAGKDNVDYSSVMLTSEEEIKTTNPVATEQYGVVADNLQQ
QNAAPIVGAVNSQGALPGMVWQNRDVYLQGPIWAKIPHTDGNFHPSPLMGGFGLKHPPPQILIKNTPVPADPPTTFN
QAKLASFITQYSTGQVSVEIEWELQKENSKRWNPEIQYTSNYYKSTNVDFAVNTEGTYSEPRPIGTRYLTRNL

RHM4-1 VP1 Amino Acid (SEQ ID NO:5)

```
  1  maadgylpdwlednlsegirewwdlkpgapkpkanqqkqdngrglvlpgykylgpfngld
 61  kgepvnaadaaalehdkaydqqlqagdnpylrynhadaefqerlqedtsfggnlgravfq
121  akkrvleplglvespvktapgkkrpvepspqrspdsstgigkkgqqpakkrlnfgqtgds
181  esvpdpqpigeppaapsgvgpntmaagggapmadnnegadgvgsssgnwhcdstwlgdrv
241  ittstrtwalptynnhlykqisngtsggstndntyfgystpwgyfdfnrfhchfsprdwq
301  rlinnnwgfrpkrlnfklfniqvkevtqnegtktianlltstiqvftdseyqlpyvlgsa
361  hqgclppfpadvfmipqygyltlnngsqav grssfycleyfpsqmlrtgnnfefsynfed
421  vpfhssyahsqsldrlmnplidqylyylsrtqstggtagtqqllfsqagpnnmsaqaknw
481  lpgpcyrqqrvsttlsqnnnsnfawtgatkyhlngrdslvnpgvamathkddeerffpss
541  gvlmfgkqgagkdnvdyssvmltseeeikttnpvateqygvvadnlqqqnaapivgavns
601  qgalpgmvwqnrdvylqgpiwakiphtdgnfhpsplmggfglkhpppqiliknttpvpadp
661  pttfnqaklasfitqystgqvsveiewelqkenskrwnpeiqytsnyykstnvdfavnte
721  gtyseprpigtryltrnl
```

| | |
|---|---|
| RHM4_1 | G195A-L199V-S201P-G202N |
| RHM15_2 | G195A-L199V-S201P-G202N K(137/259/333/530/552/569/38/51/77/163/169)R |
| RHM15_3 | G195A-L199V-S201P-G202N K(137/259/333/530/552/569/38/51/77/163/547)R |
| RHM15_4 | G195A-L199V-S201P-G202N K(137/259/333/530/552/569/38/51/77/163/668)R |
| RHM15_5 | G195A-L199V-S201P-G202N K(137/259/333/530/552/569/38/51/77/547/163)R |
| RHM15_6 | G195A-L199V-S201P-G202N K(137/259/333/530/552/569/38/51/77/547/688)R |

Figure 7

| | AAV2 | AAV8 | RHM4-1 | RHM15-5 |
|---|---|---|---|---|
| GenImm 005 | <1:3.16 | <1:1 | <1:1 | <1:1 |
| GenImm 015 | <1:1 | <1:1 | <1:1 | <1:1 |
| GenImm 040 | <1:1 | <1:1 | <1:1 | <1:1 |
| GenImm 058 | 1:3.1-1:10 | <1:1 | <1:1 | 1:1-1:3.16 |
| GenImm 070 | 1:10-1:31.6 | <1:1 | <1:1 | <1:1 |
| GenImm 080 | 1:10-1:31.6 | <1:1 | <1:1 | <1:1 |
| GenImm 082 | 1:3.1-1:10 | <1:1 | <1:1 | <1:1 |
| GenImm 083 | Neat | <1:1 | <1:1 | <1:1 |
| GenImm 087 | 1:3.1-1:10 | <1:1 | <1:1 | <1:1 |
| GenImm 095 | 1:3.1-1:10 | <1:1 | <1:1 | 1:1-1:3.16 |
| GenImm 099 | <1:1 | <1:1 | <1:1 | <1:1 |
| GenImm 102 | <1:1 | <1:1 | <1:1 | <1:1 |
| GenImm 105 | <1:1 | <1:1 | <1:1 | <1:1 |
| GenImm 100 | <1:1 | <1:1 | <1:1 | ND |
| GenImm 124 | <1:1 | <1:1 | <1:1 | <1:1 |
| GenImm 125 | 1:3.1-1:10 | <1:1 | <1:1 | 1:1-1:3.16 |
| GenImm 130 | <1:1 | <1:1 | <1:1 | <1:1 |
| GenImm 131 | 1:1-1:3.1 | <1:1 | <1:1 | <1:1 |
| GenImm 133 | <1:1 | <1:1 | <1:1 | <1:1 |
| GenImm 150 | ND | <1:1 | <1:1 | <1:1 |
| GenImm 151 | ND | <1:1 | <1:1 | <1:1 |
| GenImm 154 | ND | <1:1 | <1:1 | <1:1 |
| GenImm 155 | ND | <1:1 | <1:1 | <1:1 |
| GenImm 143 | 1:1-1:3.1 | <1:1 | <1:1 | <1:1 |
| GenImm 145 | 1:1-1:3.1 | <1:1 | <1:1 | <1:1 |
| GenImm 140 | ND | <1:1 | <1:1 | <1:1 |
| GenImm 141 | ND | <1:1 | <1:1 | <1:1 |
| GenImm 011 | ND | <1:1 | <1:1 | <1:1 |
| GenImm 049 | <1:1 | <1:1 | <1:1 | 1:1-1:3.1 |
| GenImm 146 | 1:1-1:3.1 | 1:1-1:3.1 | <1:1 | ND |
| GenImm 147 | 1:1-1:3.1 | 1:1-1:3.1 | <1:1 | ND |
| GenImm 007 | 1:100-1:316 | 1:3.16-1:10 | ND | ND |
| GenImm 084 | 1:3.1-1:10 | 1:3.1-1:10 | <1:1 | <1:1 |
| GenImm 127 | 1:100-1:316 | 1:3.1-1:10 | 1:3.1-1:10 | 1:3.16-1:10 |
| GenImm 137 | 1:100-1:316 | 1:3.1-1:10 | 1:3.1-1:10 | 1:1-1:3.16 |
| GenImm 153 | ND | 1:3.1-1:10 | 1:10-1:31.6 | 1:10-1:31.6 |
| GenImm 001 | 1:100-1:316 | 1:10-1:31.6 | ND | ND |
| GenImm 006 | 1:31.6-1:100 | 1:10-1:31.6 | 1:10-1:31.6 | 1:10-1:31.6 |
| GenImm 110 | 1:316-1:1000 | 1:10-1:31.6 | 1:31.6-1:100 | >1:31.6 |
| GenImm 128 | 1:1000-1:3160 | 1:10-1:31.6 | 1:31.6-1:100 | >1:31.6 |
| GenImm 129 | 1:31.6-1:100 | 1:10-1:31.6 | 1:3.1-1:10 | 1:3.16-1:10 |

Figure 7 (Cont.)

| | | | | |
|---|---|---|---|---|
| GenImm 148 | ND | 1:10-1:31.6 | 1:100-1:316 | >1:31.6 |
| GenImm 157 | ND | 1:10-1:31.6 | 1:3.1-1:10 | 1:10-1:31.6 |
| GenImm 158 | ND | 1:10-1:31.6 | 1:3.1-1:10 | ND |
| GenImm 028 | 1:3.1-1:10 | 1:10-1:31.6 | <1:1 | 1:1-1:3.16 |
| GenImm 016 | 1:10-1:31.6 | 1:31.6-1:100 | 1:10-1:31.6 | ND |
| GenImm 075 | 1:316-1:1000 | 1:31.6-1:100 | 1:10-1:31.6 | 1:10-1:31.6 |
| GenImm 126 | >1:3160 | 1:31.6-1:100 | 1:100-1:316 | >1:31.6 |
| GenImm 139 | ND | 1:31.6-1:100 | 1:31.6-1:100 | >1:31.6 |
| GenImm 149 | ND | 1:31.6-1:100 | 1:31.6-1:100 | ND |
| GenImm 068 | 1:3160 | 1:316-1:1000 | 1:31.6-1:100 | >1:31.6 |
| GenImm 088 | >1:3160 | 1:316-1:1000 | 1:316-1:1000 | >1:31.6 |
| GenImm 138 | ND | 1:316-1:1000 | 1:316-1:1000 | >1:31.6 |
| GenImm 004 | 1:316-1:1000 | 1:100-1:316 | ND | ND |
| GenImm 035 | >1:3160 | 1:100-1:316 | 1:100-1:316 | >1:31.6 |
| GenImm 074 | 1:3160 | 1:100-1:316 | 1:100-1:316 | >1:31.6 |
| GenImm 142 | ND | 1:100-1:316 | 1:1000-1:3160 | >1:31.6 |
| GenImm 152 | ND | 1:100-1:316 | 1:31.6-1:100 | >1:31.6 |
| GenImm 156 | ND | 1:100-1:316 | 1:100-1:316 | >1:31.6 |
| GenImm 072 | 1:3.1-1:10 | 1:100-1:316 | <1:1 | <1:1 |
| GenImm 144 | >1:3160 | 1:316-1:1000 | 1:316-1:1000 | >1:31.6 |
| GenImm 060 | >1:3160 | 1:1000-1:3160 | 1:100-1:316 | >1:31.6 |
| GenImm 069 | >1:3160 | >1:3160 | 1:1000-1:3160 | >1:31.6 |
| GenImm 017 | >1:3160 | >3160 | 1:316-1:1000 | >1:31.6 |
| GenImm 002 | <1:2 | ND | ND | ND |
| GenImm 003 | <1:2 | ND | <1:1 | <1:1 |

| | AAV2 | AAV8 | RHM4-1 | RHM15-5 |
|---|---|---|---|---|
| <1:1 | 13 | 29 | 35 | 27 |
| Total | 66 | 66 | 66 | 66 |
| % of <1:1 | 19.7 | 43.9 | 53.0 | 40.9 |

VARIANT AAV AND COMPOSITIONS, METHODS AND USES FOR GENE TRANSFER TO CELLS, ORGANS AND TISSUES

CROSS-REFERENCE TO RELATED APPLICATIONS

This application claims priority to U.S. Provisional Application No. 61/985,365, filed Apr. 28, 2014 and U.S. Provisional Application No. 61/857,161, filed Jul. 22, 2013, all of which applications are incorporated herein by reference in their entirety.

INTRODUCTION

Genetic disorders, caused by absence or a defect in a desirable gene (loss of function) or expression of an undesirable or defective gene or (gain of function) lead to a variety of diseases. One example of a loss of function genetic disorder is hemophilia, an inherited bleeding disorder caused by deficiency in either coagulation factor VIII (FVIII, hemophilia A) or factor IX (FIX, hemophilia B). One example of a gain of function genetic disorder is Huntington's disease, a disease caused by a pathologic "HTT" gene (encodes the huntingtin protein) that encodes a mutated protein that accumulates within and leads to gradual destruction of neurons, particularly in the basal ganglia and the cerebral cortex.

Current treatment for hemophilia consists in the intravenous administration of recombinant clotting factor either on demand, in case a bleeding occurs, or prophylactically. However, this therapeutic approach has several drawbacks such as the need for repeated infusions, the cost of the treatment, the risk of developing anti-therapeutic factor immune responses, and the risk of potentially fatal bleedings. These limitations have prompted the development of gene-based therapies for hemophilia. To this end, hemophilia is ideal for gene transfer based therapy as 1) the therapeutic window is very wide, as levels just above 1% of normal already can result in a change in phenotype from severe to moderate, and levels of 100% are not associated to any side effects; 2) tissue specific expression of the therapeutic transgene is not strictly required; and 3) there is a considerable experience in measuring the endpoints of therapeutic efficacy. Furthermore, liver expression of clotting factor has been demonstrated to induce immunological tolerance to the clotting factor itself, reducing the likelihood of potentially harmful immune responses against clotting factor.

Currently, adeno-associated virus (AAV) vectors are recognized as the gene transfer vectors of choice since they have the best safety and efficacy profile for the delivery of genes in vivo. Of the AAV serotypes isolated so far, AAV2 and AAV8 have been used to target the liver of humans affected by severe hemophilia B. Both vectors worked efficiently and in the case of AAV8 long-term expression of the therapeutic transgene was documented. Recent data in humans showed that targeting the liver with an AAV vector achieves long-term expression of the FIX transgene at therapeutic levels.

While these data are promising, the identification of AAV serotypes with high tropism for liver and low seroprevalence in humans (a natural host for wild type AAV) is fundamental for 1) achieving therapeutic levels of transgene expression in liver at the lowest vector dose possible to decrease risk of triggering anti-AAV capsid immune responses; and 2) alternate AAV serotypes with unique seroprevalence will allow to treat those patients populations otherwise not eligible for AAV gene transfer due to pre-existing humoral immunity to AAVs. The invention addresses these needs and provides additional benefits.

SUMMARY

The invention provides adeno-associated virus (AAV) serotype AAV-Rh74 vector, and related AAV vectors and viral particles. Such vectors include AAV-Rh74 which target hepatocyte cells of the liver, among other cell types. As a vector for polynucleotide sequence delivery, AAV-Rh74 and related AAV vectors drive expression of the polynucleotide in cells. Polynucleotides that encode proteins, such as proteins for therapeutic applications are able to be expressed at therapeutic levels after administration.

Exemplary AAV-Rh74 and related AAV vectors include AAV-Rh74 variants. Particular capsid variants include an Rh74 capsid sequence with an amino acid substitution at any one of amino acid positions 195, 199, 201 or 202, of RH74 VP1 capsid sequence (SEQ ID NO:1). In particular aspects, the residues correspond to an A, V, P or N amino acid at any one of amino acid positions 195, 199, 201 or 202 of RH74 VP1 capsid sequence (SEQ ID NO:1). In more particular aspects, the capsid sequence has an A residue at amino acid position 195; a V residue at amino acid positions 199, a P residue at amino acid position 201, or an N residue at amino acid position 202 of RH74 VP1 capsid sequence (SEQ ID NO:1). In further more particular aspects, the capsid sequence has any two, three or all four of the following: an A residue at amino acid position 195; a V residue at amino acid positions 199, a P residue at amino acid position 201, or an N residue at amino acid position 202 of RH74 VP1 capsid sequence (SEQ ID NO:1).

Recombinant AAV particles of the invention include an AAV capsid sequence of any capsid variant such as RHM4-1 (SEQ ID NO:5), RHM15-1 (SEQ ID NO:6), RHM15-2 (SEQ ID NO:7), RHM15-3/RHM15-5 (SEQ ID NO:8), RHM15-4 (SEQ ID NO:9) or RHM15-6 (SEQ ID NO:10). In particular embodiments, a recombinant AAV particle encapsidates or packages a vector genome (e.g., viral vector such as an AAV vector genome). Such invention recombinant AAV particles include a viral (e.g., AAV) vector genome which also includes a heterologous polynucleotide sequence.

AAV-Rh74 and related AAV vector mediated polynucleotide transfer produced protein expression levels that were significantly higher than several other serotypes currently studied in preclinical and clinical settings. In particular, AAV-Rh74 targets polynucleotides to the liver with efficiency at least comparable or superior to the gold standard for liver transduction, AAV8, both in mice and in hemophilia B dogs. (see, e.g., FIGS. 1 and 2). AAV-Rh74 variants such as, for example, capsid variant RHM4-1 (SEQ ID NO:5) target polynucleotides to the liver with efficiency comparable to or superior to AAV8 and superior to Rh74 AAV in mice (see, e.g., FIG. 5). In addition, data in non-human primates show that AAV-Rh74 and AAV-Rh74 variants such as RHM4-1 are approximately two-fold more potent than AAV8 at mediating liver-derived expression of hFIX (see, e.g., FIGS. 4 and 6).

Thus, AAV-Rh74 and AAV-Rh74 variants such as capsid variants (e.g., RHM4-1) can be used to deliver polynucleotides, such as gene coding sequences, to express proteins that provide a desirable or therapeutic benefit, as well as for inhibitory nucleotides that reduce or inhibit expression of an undesirable or defective gene, thereby treating a variety of diseases. For example, AAV-Rh74 and AAV-Rh74capsid variants (e.g., RHM4-1) can be used as vectors to deliver to cells, tissues and organs, such as liver therapeutic genes (e.g., FIX, FVIII) to treat hemophilia A, B, etc. Such AAV-Rh74 and AAV-Rh74capsid variant (e.g., RHM4-1) vectors can also be used to deliver genes for a wide range of other metabolic or plasma protein deficiencies, or for other therapeutic purposes, such as but not limited to genes encoding zinc finger nucleases to carry out genome editing in the liver, and for local (liver) delivery of immunomodulatory agents such as alpha-interferon for treatment of hepatitis virus infections, or to treat virtually any disease that requires either liver transduction or presence of the therapeutic transgene product in the bloodstream (which can be achieved by targeting the transgenes for liver expression).

In addition to efficient delivery of polynucleotides by AAV-Rh74 and related AAV vectors such as AAV-Rh74 variants such as capsid variants (e.g., RHM4-1) into cells in vitro, ex vivo and in vivo, prevalence of anti-AAV-Rh74 antibodies in humans is lower than anti-AAV2 antibodies, and differs from that of anti-AAV8 antibodies (FIG. 7). Owing to low sero-prevalence, AAV-Rh74 and related AAV vectors such as AAV-Rh74 (capsid) variants (e.g., RHM4-1) can be used in a greater percentage of humans which otherwise would not be eligible for gene transfer, for example, humans that may be sero-positive for other AAV serotypes (e.g., AAV1, AAV2, AAV3, AAV4, AAV5, AAV6, AAV7, AAV8, AAV9, AAV10, AAV11, etc.). In addition, AAV-Rh74 and related vectors such as AAV-Rh74 variants including capsid variants (e.g., RHM4-1) can be efficiently produced at high titers (Table 2). Thus, AAV-Rh74 and related AAV vectors can be produced in large amounts for more prevalent clinical diseases.

In accordance with the invention, there are provided recombinant AAV-Rh74 vectors and related AAV vectors such as AAV-Rh74 variants such as capsid variants (e.g., RHM4-1) particles that include (encapsidate, package) AAV vector genomes. In one embodiment, a recombinant AAV vector includes a heterologous polynucleotide sequence. In another embodiment, a recombinant AAV vector genome is encapsidated or packaged by an AAV-Rh74 capsid or a related AAV such as AAV-Rh74 variants such as a capsid variant (e.g., RHM4-1).

In invention recombinant AAV vectors, such as AAV-Rh74 vectors and related AAV vectors such as AAV-Rh74 (capsid) variants (e.g., RHM4-1) particles that include (encapsidate, package) recombinant AAV vector genomes, the heterologous polynucleotide sequence may or be transcribed and subsequently translated into a protein. Alternatively, the heterologous polynucleotide may be transcribed into a transcript that in itself has a function or activity (e.g., as an inhibitory nucleic acid).

In various aspects, the heterologous polynucleotide sequence encodes a therapeutic protein. In particular aspects, the protein is a blood clotting factor (e.g., Factor XIII, Factor IX, Factor X, Factor VIII, Factor VIIa, or protein C), CFTR (cystic fibrosis transmembrane regulator protein), an antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor (e.g., insulin-like growth factors 1 and 2, platelet derived growth factor, epidermal growth factor, nerve growth factor, neurotrophic factor-3 and -4, brain-derived neurotrophic factor, glial derived growth factor, transforming growth factor α and β, etc.), a cytokine (e.g., α-interferon, β-interferon, interferon-γ, interleukin-2, interleukin-4, interleukin 12, granulocyte-macrophage colony stimulating factor, lymphotoxin, etc.), a suicide gene product (e.g., herpes simplex virus thymidine kinase, cytosine deaminase, diphtheria toxin, cytochrome P450, deoxycytidine kinase, tumor necrosis factor, etc.), a drug resistance protein (e.g, that provides resistance to a drug used in cancer therapy), a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitopes, or hCDR1, insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USH1C (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, gene deficiencies causative of lysosomal storage diseases (e.g., sulfatases, N-acetylglucosamine-1-phosphate transferase, cathepsin A, GM2-AP, NPC1, VPC2, Sphingolipid activator proteins, etc.), one or more zinc finger nucleases for genome editing, or donor sequences used as repair templates for genome editing.

In additional aspects, the heterologous polynucleotide sequence encodes a therapeutic protein that in turn inhibits expression or function of an undesirable or aberrant (dysfunctional) protein present (endogenous) in a subject. In further aspects, the heterologous polynucleotide sequence is a polynucleotide which, when transcribed, is transcribed into an inhibitory nucleic acid (e.g., inhibitory RNA). In more particular aspects, an inhibitory nucleic acid is a single-stranded sequence, or forms a double- or triple-stranded sequence. In additional more particular aspects, an inhibitory nucleic acid is a micro-RNA (miRNA), siRNA, shRNA, trans-splicing RNA, antisense RNA or triplex forming RNA.

In further more particular aspects, an inhibitory nucleic acid inhibits expression of: huntingtin (HTT) gene, a gene associated with dentatorubropallidolusyan atropy (e.g., atrophin 1, ATN1); androgen receptor on the X chromosome in spinobulbar muscular atrophy, human Ataxin-1, -2, -3, and -7, $Ca_v2.1$ P/Q voltage-dependent calcium channel is encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercoloesterolemia; HIV Tat, human immunodeficiency virus transactivator of transcription gene, in HIV infection; HIV TAR, HIV TAR, human immunodeficiency virus transactivator response element gene, in HIV infection; C-C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DAN damage-inducible transcript 4 protein, in diabetic macular oedma (DME) or age-related macular degeneration; vascular endothelial growth factor receptor I (VEGFR1) in age-related macular degeneration or choroidal neivascularization, caspase 2 in non-arteritic ischaemic optic neuropathy; Keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and HLA-allele specific in transplant; mutant rhodopsin gene (RHO) in autosomal dominantly inherited retinitis pigmentosa (adRP); or the inhibitory nucleic acid binds to a transcript of any of the foregoing genes or sequences.

Invention recombinant AAV vectors and AAV-Rh74 and related AAV vectors such as AAV-Rh74 vector variants such as capsid variants (e.g., RHM4-1) particles that include (encapsidate, package) recombinant AAV vector genome include additional elements that function in cis or in trans. In particular embodiments, a recombinant viral (e.g., AAV) vector and/or AAV-Rh74 vector or related AAV vector such as a AAV-Rh74 (capsid) variants (e.g., RHM4-1) particle that includes (encapsidate, package) recombinant AAV vector genome also has: one or more inverted terminal repeat (ITR) sequences that flank the 5' or 3' terminus of the heterologous polynucleotide sequence; an expression control sequence that drives transcription of the heterologous polynucleotide sequence (e.g., a promoter or enhancer that contributes to transcription of the heterologous polynucleotide sequence, such as a constitutive or regulatable control element, or tissue-specific expression control element); a poly-Adenine sequence located 3' of the heterologous polynucleotide sequence; a selectable marker (e.g., a protein that provides antibiotic resistance, such as Kanamycin resistance); and/or an origin of replication.

Invention recombinant AAV vectors and AAV-Rh74 vectors and related AAV vectors such as AAV-Rh74 variants including capsid variant (e.g., RHM4-1) particles that include (encapsidate, package) recombinant AAV vector genome can also include additional elements. In one embodiment, a recombinant vector genome includes a heterologous polynucleotide sequence and a filler or stuffer polynucleotide sequence. In particular aspects, a heterologous polynucleotide sequence has a length less than about 4.7 Kb. In further particular aspects, a heterologous polynucleotide sequence has a length less than 4.7 Kb and is positioned within two adeno-associated virus (AAV) ITR sequences. In additional particular aspects, a filler or stuffer polynucleotide sequence has a length that when combined with the heterologous polynucleotide sequence the total combined length of the heterologous polynucleotide sequence and filler or stuffer polynucleotide sequence is between about 3.0-5.5 Kb, or between about 4.0-5.0 Kb, or between about 4.3-4.8 Kb.

Filler or stuffer polynucleotide sequences can be located in the vector sequence at any desired position such that it does not prevent a function or activity of the vector. In one aspect, a filler or stuffer polynucleotide sequence is not positioned between a 5' and/or 3' ITR that flanks the respective 5' and/or 3' termini of a heterologous polynucleotide sequence. In another aspect, a filler or stuffer polynucleotide sequence is positioned within a 5' and/or 3' ITR that flanks the respective 5' and/or 3' termini of a heterologous polynucleotide sequence. In an additional aspect, a filler or stuffer polynucleotide sequence is positioned adjacent to 5' and/or 3' ITR that flanks the respective 5' and/or 3' termini of a heterologous polynucleotide sequence. In a further aspect, a filler or stuffer polynucleotide sequence is positioned within a heterologous polynucleotide sequence, e.g., analogous to an intron within a genomic nucleic acid.

Accordingly, in various embodiments, a filler or stuffer polynucleotide sequence is positioned adjacent to an AAV ITR sequence; positioned within two adeno-associated virus (AAV) ITR sequences; positioned outside two adeno-associated virus (AAV) ITR sequences; or there are two filler or stuffer polynucleotide sequences, a first filler or stuffer polynucleotide sequence positioned within two adeno-associated virus (AAV) ITR sequences, and a second filler or stuffer polynucleotide sequence positioned outside two adeno-associated virus (AAV) ITR sequences.

In more particular aspects, a filler or stuffer polynucleotide sequence has a length that when combined with said heterologous polynucleotide sequence the total combined length of the heterologous polynucleotide sequence and filler or stuffer polynucleotide sequence is between about 3.0-5.5 Kb, between about 4.0-5.0 Kb, or between about 4.3-4.8 Kb, when positioned within two adeno-associated virus (AAV) ITR sequences. In other more particular aspects, a filler or stuffer polynucleotide sequence has a length greater than 4.7 Kb, between about 5.0-10.0 Kb, or between about 6.0-8.0 Kb, when positioned outside two adeno-associated virus (AAV) ITR sequences.

In various additional aspects, a filler or stuffer polynucleotide sequence is a sequence between about 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000 nucleotides in length.

Typically, a filler or stuffer polynucleotide sequence is inert or innocuous and has no function or activity. In various particular aspects, a filler or stuffer polynucleotide sequence is not a bacterial polynucleotide sequence, a filler or stuffer polynucleotide sequence is not a sequence that encodes a protein or peptide, a filler or stuffer polynucleotide sequence is a sequence distinct from any of: the heterologous polynucleotide sequence, an AAV inverted terminal repeat (ITR) sequence, an expression control element, an origin of replication, a selectable marker or a poly-Adenine (poly-A) sequence.

In various additional particular aspects, a filler or stuffer polynucleotide sequence is an intron sequence that is related to or unrelated to the heterologous polynucleotide sequence. In particular aspects, the intron sequence is positioned within the heterologous polynucleotide sequence. In other particular aspects, the intron sequence is related to the heterologous polynucleotide sequence as the intron is in genomic DNA, such as the genomic DNA that encodes a protein which protein is also encoded by the heterologous polynucleotide sequence.

Invention recombinant AAV vectors and AAV-Rh74 and related AAV vectors such as AAV-Rh74 variants such as capsid variant (e.g., RHM4-1) particles that include (encapsidate, package) recombinant AAV vector genome can be included within cells. In such embodiments, cells can comprise helper cells lysed to produce virus (AAV) particles (e.g., AAV-Rh74 vectors or related AAV vectors such as AAV-Rh74 capsid variants (e.g., RHM4-1)), or target cells in which it is desired to express the heterologous polynucleotide sequence.

Invention recombinant AAV vectors and AAV-Rh74 vectors and related AAV vectors such as AAV-Rh74 variants (e.g., capsid variants such as RHM4-1) particles that include (encapsidate, package) recombinant AAV vector genome can be included within pharmaceutical compositions. Such compositions are useful for administration of recombinant vector (e.g., AAV) and virus particles such as AAV-Rh74 vectors and related AAV vectors such as AAV-Rh74 variants (e.g., capsid variants such as RHM4-1) that include (encapsidate, package) recombinant vector (e.g., AAV) genomes to a subject.

Invention recombinant AAV vectors and AAV-Rh74 vectors and related AAV vectors such as AAV-Rh74 variants (e.g., capsid variants such as RHM4-1) particles that include (encapsidate, package) recombinant AAV vector genome may be employed in various methods and uses. Accordingly, there are provided methods and uses for delivering or transferring a heterologous polynucleotide sequence into an organism or cell, such as a mammal or a cell of a mammal.

In one embodiment, a method or use includes administering an adeno-associated virus (AAV) vector that includes a heterologous polynucleotide sequence (e.g., via an AAV-Rh74 vector or related AAV such as AAV-Rh74 variants (e.g., capsid variants such as RHM4-1)) particle that includes (encapsidate, package) the vector genome to a mammal or a cell of a mammal under suitable conditions to deliver or transfer the heterologous polynucleotide sequence into the mammal or the cell of a mammal. In one aspect, the method or use allows transfer/delivery of the heterologous polynucleotide into the mammal and/or cell. In another aspect, the method allows transfer/delivery of the heterologous polynucleotide into the mammal and/or cell, and subsequent transcription of the heterologous polynucleotide thereby forming a transcript. In a further aspect, the method allows transfer/delivery of the heterologous polynucleotide into the cell, subsequent transcription to form a transcript and subsequent translation to form a gene product (protein). In particular, for example, in the latter two aspects a heterologous polynucleotide sequence is operably linked to an expression control element conferring transcription of the heterologous polynucleotide sequence, and optionally subsequent translation of the transcript.

In additional embodiments, a method or use is for delivering or transferring a heterologous polynucleotide sequence into a subject (e.g., mammal) or a cell of a subject (e.g., mammal), and includes administering a viral (e.g., AAV-Rh74 or related AAV such as AAV-Rh74 capsid variants (e.g., RHM4-1)) particle, a plurality of such viral (e.g., AAV) particles, or a pharmaceutical composition of such a viral (e.g., AAV-Rh74 or related AAV such as AAV-Rh74 capsid variants (e.g., RHM4-1)) particle or plurality of such viral (e.g., AAV) particles to a subject (e.g., mammal) or a cell of the subject (e.g., mammal), thereby delivering or transferring a heterologous polynucleotide sequence into the subject (e.g., mammal) or cell of the subject (e.g., mammal)

In another embodiment, a method or use is for treating a subject (e.g., mammal) deficient or in need of protein expression or function, or in need of reduced expression or function of an endogenous protein (e.g., an undesirable, aberrant or dysfunctional protein), that includes providing a viral (e.g., AAV-Rh74 and related AAV such as AAV-Rh74 variants (e.g., capsid variants such as RHM4-1)) particle, a plurality of such viral (e.g., AAV) particles, or a pharmaceutical composition of a viral (e.g., AAV-Rh74 and related AAV such as AAV-Rh74 variants (e.g., capsid variants such as RHM4-1)) particle or plurality of such viral (e.g., AAV) particles; and administering the viral (e.g., AAV-Rh74 and related AAV such as AAV-Rh74 variants (e.g., capsid variants such as RHM4-1)) particle, plurality of such viral (e.g., AAV) particles, or pharmaceutical composition of viral (e.g., AAV-Rh74 and related AAV such as AAV-Rh74 variants (e.g., capsid variants such as RHM4-1)) particle or plurality of such viral (e.g., AAV) particles to the subject (e.g., mammal), where the heterologous polynucleotide sequence is expressed in the mammal, or wherein the heterologous polynucleotide sequence encodes an inhibitory sequence or protein that reduces expression or function of an endogenous protein (e.g., an undesirable, aberrant or dysfunctional protein) in the subject (e.g., mammal).

Methods and uses for administration or delivery include any mode compatible with a subject. In particular embodiments, a viral (e.g., AAV-Rh74 or related AAV such as AAV-Rh74 capsid variant (e.g., RHM4-1)) particle or plurality of such viral (e.g., AAV) particles (e.g., AAV-Rh74 vectors or related AAV vectors such as AAV-Rh74 capsid variants (e.g., RHM4-1)) is administered or delivered intravenously, intraarterially, intramuscularly, subcutaneously, orally, by intubation, via catheter, dermally, intra-cranially, via inhalation, intra-cavity, or mucosally.

Subjects include mammals, such as humans and non-humans (e.g., primates). In particular embodiments, a subject would benefit from or is in need of expression of a heterologous polynucleotide sequence.

In accordance with the invention, methods of producing recombinant vector (e.g., AAV) plasmids and virus (e.g., AAV-Rh74 and related AAV such as AAV-Rh74 variants (e.g., capsid variants such as RHM4-1)) particles that include (encapsidate, package) recombinant vector (e.g., AAV) are provided. In one embodiment, a method of producing recombinant viral or AAV particles includes introducing into a packaging helper cell a recombinant vector (e.g., AAV) plasmid to produce a productive viral (e.g., AAV-Rh74 and related AAV such as AAV-Rh74 variants (e.g., capsid variants such as RHM4-1)) infection; and culturing the helper cells under conditions to produce recombinant viral (e.g., AAV-Rh74 or related AAV such as AAV-Rh74 capsid variants (e.g., RHM4-1)) particles. In another embodiment, a method of producing recombinant viral or AAV particles with reduced amounts of recombinant viral (e.g., AAV-Rh74 and related AAV such as AAV-Rh74 variants (e.g., capsid variants such as RHM4-1)) particles in which the recombinant viral vector includes contaminating nucleic acid, includes introducing into a packaging helper cell a recombinant vector (e.g., AAV) plasmid; and culturing the helper cells under conditions to produce recombinant viral (e.g., AAV-Rh74 and related AAV such as AAV-Rh74 variants (e.g., capsid variants such as RHM4-1)) particles, wherein the recombinant viral (e.g., AAV-Rh74 and related AAV such as AAV-Rh74 variants (e.g., capsid variants such as RHM4-1)) particles produced have reduced numbers of viral (e.g., AAV-Rh74 and related AAV such as AAV-Rh74 variants (e.g., capsid variants such as RHM4-1)) particles with recombinant vector genomes that contain contaminating nucleic acid compared to the numbers of viral (e.g., AAV-Rh74 and related AAV such as AAV-Rh74 variants (e.g., capsid variants such as RHM4-1)) particles that contain contaminating nucleic acid produced under conditions in which the filler or stuffer polynucleotide sequence is absent from the recombinant viral vector. In particular aspects, the contaminating nucleic acid is bacterial nucleic acid; or a sequences other than the heterologous polynucleotide sequence, or ITR, promoter, enhancer, origin of replication, poly-Adenine sequence, or selectable marker.

Helper cells include mammalian cells. In particular embodiments, a helper cell provides helper (e.g., AAV) functions to package the heterologous polynucleotide sequence into a viral particle (e.g., AAV particle such as AAV-Rh74 and related AAV vectors such as AAV-Rh74 variants (e.g., capsid variants such as RHM4-1)). In particular aspects, a helper cell provides AAV Rep and/or Cap proteins (e.g., Rep78 or/and Rep68 proteins); a helper cell is stably or transiently transfected with polynucleotide(s) encoding Rep and/or Cap protein sequence(s); a helper cell is stably or transiently transfected with Rep78 and/or Rep68 protein polynucleotide encoding sequence(s).

Invention recombinant vector (e.g., AAV) plasmids can be based upon any strain or serotype, including hybrids or chimeras of different serotypes. Invention recombinant viral (e.g., AAV) particles are typically based upon AAV-Rh74 or related AAV such as AAV-Rh74 and related AAV such as AAV-Rh74 variants (e.g., capsid variants such as RHM4-1)), but also include hybrids or chimeras with different serotypes. Representative AAV serotypes include, without limitation, AAV1, AAV2, AAV3, AAV4, AAV5, AAV6, AAV7, AAV8, AAV9, AAV10, AAV11, and Rh10 serotypes. Accordingly, invention recombinant viral (e.g., AAV) particles comprising vector genomes can include a capsid protein from a different serotype, a mixture of serotypes, or hybrids or chimeras of different serotypes, such as a VP1, VP2 or VP3 capsid protein of AAV1, AAV2, AAV3, AAV4, AAV5, AAV6, AAV7, AAV8, AAV9, AAV10, AAV11, Rh10 serotype. Furthermore, invention recombinant vectors (e.g., AAV), sequences, plasmids, vector genomes, can include elements from any one serotype, a mixture of serotypes, or hybrids or chimeras of different serotypes. In various embodiments, a recombinant AAV vector includes a Cap, Rep, and/or ITR sequence derived from AAV1, AAV2, AAV3, AAV4, AAV5, AAV6, AAV7, AAV8, AAV9, AAV10, AAV11, Rh74, or Rh10 serotype, or a mixture, hybrid or chimera of any of the foregoing AAV serotypes.

DESCRIPTION OF DRAWINGS

The patent or application file contains at least one drawing executed in color. Copies of this patent or patent application publication with color drawing(s) will be provided by the Office upon request and payment of the necessary fee.

FIGS. 3A-3B show AAV-Rh74 VP1, VP2, and VP3 amino acid sequences and, for VP1, polynucleotide (DNA) sequence (SEQ ID NOs:1-4).

FIG. 7 shows anti-AAV neutralizing antibodies (NAb) measured in humans with an in vitro assay.

DETAILED DESCRIPTION

Figure 1:
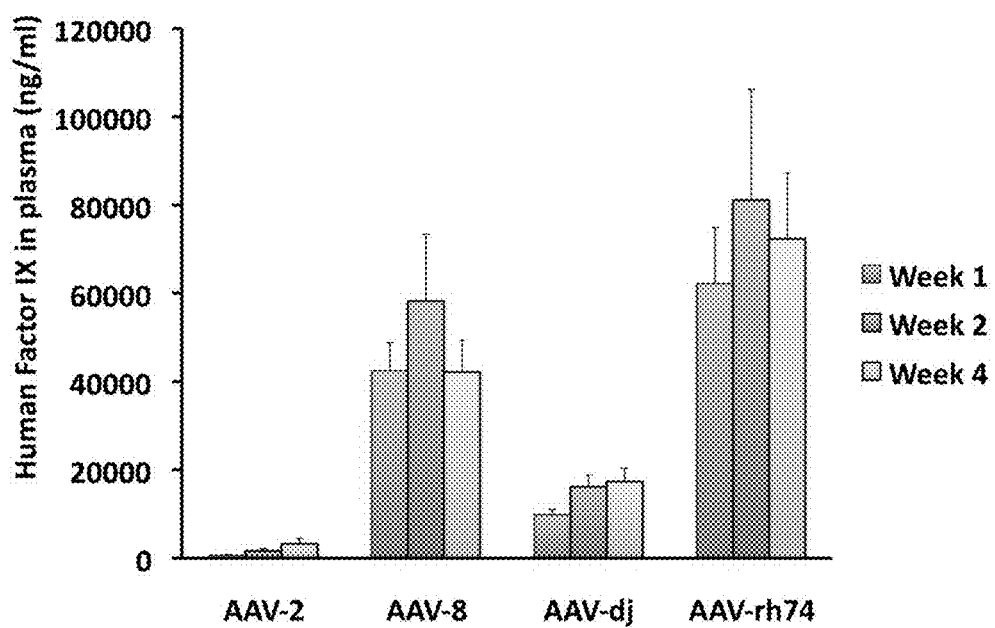
FIG. 1 shows human factor IX (FIX) plasma levels in C57BL/6 mice (n=5 per group) injected via the tail vein with AAV vectors expressing the FIX transgene under the control of a liver-specific promoter. Vector dose $2.5^{10}$ vector genomes per mouse. FIX transgene product (FIX protein) plasma levels were measured by ELISA at weeks 1, 2, and 4 post gene transfer. AAV-Rh74 conferred the highest levels of FIX transgene expression.

The invention is based, at least in part, on data indicating that adeno-associated virus (AAV) serotype AAV-Rh74 and related AAV variants such as AAV-Rh74 capsid variants (e.g., RHM4-1, RHM15-1, RHM15-2, RHM15-3/RHM15-5, RHM15-4 and RHM15-6) have a high tropism for hepatocytes, which are cells of the liver. As a vector for polynucleotide (e.g. genes, inhibitory nucleic acid, etc.) transfer/delivery into cells, AAV-Rh74 and related AAV variants such as AAV-Rh74 variants (e.g., capsid variants such as RHM4-1, RHM15-1, RHM15-2, RHM15-3/RHM15-5, RHM15-4 and RHM15-6) can be used to provide therapeutic levels of expression in liver after intravenous administration. Furthermore, AAV-Rh74 vectors and related AAV variants such as AAV-Rh74 variants (e.g., capsid variants such as RHM4-1, RHM15-1, RHM15-2, RHM15-3/RHM15-5, RHM15-4 and RHM15-6) mediated gene transfer/delivery produced protein expression levels that were significantly higher than several other serotypes (see, e.g., FIGS. 1, 2, 4, 5 and 6). In particular, AAV-Rh74 vector and related AAV-Rh74 capsid variants (e.g., RHM4-1) target genes for delivery to the liver with efficiency at least comparable and typically superior to the gold standard for liver transduction, AAV8, in hemophilia B dogs and/or in mice and/or macaques. Thus, AAV-Rh74 vectors and related AAV variants such as AAV-Rh74 capsid variants (e.g., RHM4-1) can be used to transfer/deliver heterologous polynucleotides, such as coding sequences (genes) for proteins that provide a desirable or therapeutic benefit, as well as inhibitory (e.g., anti-sense) nucleic acid that reduce or inhibit expression of an undesirable or defective (e.g., pathologic) gene, thereby treating a variety of diseases. For example, a recombinant vector (e.g., AAV) genome can be packaged or encapsidated within AAV-Rh74 vector or related AAV variants such as AAV-Rh74 capsid variants (e.g., RHM4-1, RHM15-1, RHM15-2, RHM15-3/RHM15-5, RHM15-4 and RHM15-6) in order to transfer/deliver a heterologous polynucleotide into a cell.

As set forth herein, adeno-associated virus (AAV) serotype AAV-Rh74 and related AAV variants such as AAV-Rh74 capsid variants (e.g., RHM4-1, RHM15-1, RHM15-2, RHM15-3/RHM15-5, RHM15-4 and RHM15-6) provide a means for delivery of polynucleotide sequences into cells ex vivo, in vitro and in vivo. Such polynucleotide sequences can encode proteins such that the cells into which the polynucleotides are delivered express the encoded proteins. For example, a recombinant AAV vector can include heterologous polynucleotides encoding a desired protein or peptide, or a heterologous polynucleotide that when transcribed comprises an inhibitory sequence (e.g., RNA), for example, a sequence that targets a gene for inhibition of expression. Vector delivery or administration to a subject (e.g., mammal) therefore provides not only heterologous polynucleotides encoding proteins and peptides to the subject, but also inhibitory nucleic acids that target genes for inhibition of expression or function in the subject.

Thus, in accordance with the invention AAV-Rh74 vectors and related AAV vector variants such as AAV-Rh74 variants (e.g., capsid variants such as RHM4-1, RHM15-1, RHM15-2, RHM15-3/RHM15-5, RHM15-4 and RHM15-6) that include (encapsidate or package) vector genome including polynucleotide sequences encoding peptides and proteins, as well as polynucleotide sequences which directly or when transcribed comprise inhibitory nucleic acids that target genes for inhibition of expression or function, are provided.

A recombinant "vector" or "AAV vector" is derived from the wild type genome of a virus, such as AAV by using molecular methods to remove the wild type genome from the virus (e.g., AAV), and replacing with a non-native nucleic acid, such as a heterologous polynucleotide sequence (e.g., a therapeutic gene expression cassette). Typically, for AAV one or both inverted terminal repeat (ITR) sequences of the wild type AAV genome are retained in the AAV vector. A recombinant viral vector (e.g., AAV) is distinguished from a viral (e.g., AAV) genome, since all or a part of the viral genome has been replaced with a non-native sequence with respect to the viral (e.g., AAV) genomic nucleic acid such as a heterologous polynucleotide sequence. Incorporation of a non-native sequence such as a heterologous polynucleotide therefore defines the viral vector (e.g., AAV) as a "recombinant" vector, which in the case of AAV can be referred to as an "rAAV vector."

A recombinant vector (e.g., AAV) sequence can be packaged into a virus (also referred to herein as a "particle" or "virion") for subsequent infection (transformation) of a cell, ex vivo, in vitro or in vivo. Where a recombinant vector sequence is encapsidated or packaged into an AAV particle, the particle can be referred to as a "rAAV." Such particles or virions will typically include proteins that encapsidate or package the vector genome. Particular examples include viral envelope proteins, and in the case of AAV capsid proteins.

In particular embodiments, a recombinant vector (e.g., AAV) is a parvovirus vector. Parvoviruses are small viruses with a single-stranded DNA genome. "Adeno-associated viruses" (AAV) are in the parvovirus family.

Parvoviruses including AAV are viruses useful as gene therapy vectors as they can penetrate cells and introduce nucleic acid/genetic material so that the nucleic acid/genetic material may be stably maintained in cells. In addition, these viruses can introduce nucleic acid/genetic material into specific sites, for example, such as a specific site on chromosome 19. Because AAV are not associated with pathogenic disease in humans, AAV vectors are able to deliver heterologous polynucleotide sequences (e.g., therapeutic proteins and agents) to human patients without causing substantial AAV pathogenesis or disease.

AAV-Rh74 and related AAV variants such as AAV-Rh74 or related AAV such as AAV-Rh74 variants (e.g., capsid variants such as RHM4-1) serotypes (e.g., VP1, VP2, and/or VP3 sequences) may or may not be distinct from other AAV serotypes, including, for example, AAV1-AAV11 or Rh10 (e.g., distinct from VP1, VP2, and/or VP3 sequences of any of AAV1-AAV11, or Rh10 serotypes). As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV-Rh74 variants including capsid variants may not be serologically distinct from Rh74 or other AAV, they differ by at least one nucleotide or amino acid residue compared to Rh74 or other AAV.

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

Recombinant vector (e.g., AAV) plasmids, as well as methods and uses thereof, include any viral strain or serotype. As a non-limiting example, a recombinant vector (e.g., AAV) plasmid can be based upon any AAV genome, such as AAV-1, -2, -3, -4, -5, -6, -7, -8, -9, -10, -11, -rh74, -rh10 or AAV-2i8, for example. Such vectors can be based on the same of strain or serotype (or subgroup or variant), or be different from each other. As a non-limiting example, a recombinant vector (e.g., AAV) plasmid based upon one serotype genome can be identical to one or more of the capsid proteins that package the vector. In addition, a recombinant vector (e.g., AAV) plasmid can be based upon an AAV (e.g., AAV2) serotype genome distinct from one or more of the capsid proteins that package the vector, in which case at least one of the three capsid proteins could be a AAV-Rh74 or related AAV variant such as AAV-Rh74 or related AAV such as AAV-Rh74 variants (e.g., capsid variants such as RHM4-1, RHM15-1, RHM15-2, RHM15-3/RHM15-5, RHM15-4 and RHM15-6), for example.

AAV-Rh74 has gene/protein sequences identical to sequences characteristic for AAV-Rh74 (see, e.g., VP1, VP2, VP3 of FIG. 3). As used herein, an "AAV vector related to AAV-Rh74" and grammatical variations thereof refers to one or more AAV proteins (e.g., VP1, VP2, and/or VP3 sequences) that has substantial sequence identity to one or more polynucleotides or polypeptide sequences that comprise AAV-Rh74. Such AAV vectors related to AAV-Rh74 can therefore have one or more distinct sequences from AAV-Rh74, but can exhibit substantial sequence identity to one or more genes and/or have one or more functional characteristics of AAV-Rh74 (e.g., such as cell/tissue tropism). For example, AAV-Rh74 related AAV variant RHM4-1 has a capsid with four amino acids different from Rh74 capsid. Exemplary AAV-Rh74 and related AAV variants such as AAV-Rh74 or related AAV such as AAV-Rh74 variants (e.g., capsid variants such as RHM4-1, RHM15-1, RHM15-2, RHM15-3/RHM15-5, RHM15-4 and RHM15-6) sequences include VP1, VP2, and/or VP3 set forth herein, for example, in FIG. 3. In one non-limiting exemplary embodiment, an AAV vector related to AAV-Rh74 has a polynucleotide, polypeptide or subsequence thereof that includes or consists of a sequence at least 80% or more (e.g., 85%, 90%, 95%, 96%, 97%, 98%, 99%, 99.5%, etc.) identical to one or more AAV-Rh74 VP1, VP2, and/or VP3 sequences set forth in FIG. 3.

In accordance with the invention, methods and uses include AAV-Rh74 sequences (polypeptides and nucleotides) and subsequences thereof that exhibit less than 100% sequence identity to a reference AAV-Rh74 gene or protein sequence (e.g., VP1, VP2, and/or VP3 sequences set forth in FIG. 3), but are distinct from and not identical to known AAV genes or proteins, such as AAV1-AAV11, AAV-Rh10, genes or proteins, etc. In one embodiment, an AAV-Rh74 polypeptide or subsequence thereof includes or consists of a sequence at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical to any reference AAV-Rh74 sequence or subsequence thereof (e.g., VP1, VP2 and/or VP3 sequences set forth in FIG. 3). In particular aspects, an AAV-Rh74 related variant has one, two, three or four of the four amino acid substitutions set forth in AAV-Rh74 (e.g., capsid variant RHM4-1, RHM15-1, RHM15-2, RHM15-3/RHM15-5, RHM15-4 and RHM15-6).

Recombinant vectors (e.g., AAV), including AAV1, AAV2, AAV3, AAV4, AAV5, AAV6, AAV7, AAV8, AAV9, AAV10, AAV11, Rh10, Rh74 or AAV-2i8 and variant, related, hybrid and chimeric sequences, can be constructed using recombinant techniques that are known to the skilled artisan, to include one or more heterologous polynucleotide sequences (transgenes) flanked with one or more functional AAV ITR sequences. Such vectors can have one or more of the wild type AAV genes deleted in whole or in part, for example, a rep and/or cap gene, but retain at least one functional flanking ITR sequence, as necessary for the rescue, replication, and packaging of the recombinant vector into an AAV vector particle. An AAV vector genome would therefore include sequences required in cis for replication and packaging (e.g., functional ITR sequences)

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides include naturally occurring, synthetic, and intentionally altered or modified polynucleotides as well as analogues and derivatives. Polynucleotides can be single, double, or triplex, linear or circular, and can be of any length. In discussing polynucleotides, a sequence or structure of a particular polynucleotide may be described herein according to the convention of providing the sequence in the 5' to 3' direction.

A "heterologous" polynucleotide refers to a polynucleotide inserted into a vector (e.g., AAV) for purposes of vector mediated transfer/delivery of the polynucleotide into a cell. Heterologous polynucleotides are typically distinct from vector (e.g., AAV) nucleic acid, i.e., are non-native with respect to viral (e.g., AAV) nucleic acid. Once transferred/delivered into the cell, a heterologous polynucleotide, contained within the virion, can be expressed (e.g., transcribed, and translated if appropriate). Alternatively, a transferred/delivered heterologous polynucleotide in a cell, contained within the virion, need not be expressed. Although the term "heterologous" is not always used herein in reference to polynucleotides, reference to a polynucleotide even in the absence of the modifier "heterologous" is intended to include heterologous polynucleotides in spite of the omission.

The "polypeptides," "proteins" and "peptides" encoded by the "polynucleotide sequences," include full-length native sequences, as with naturally occurring proteins, as well as functional subsequences, modified forms or sequence variants so long as the subsequence, modified form or variant retains some degree of functionality of the native full-length protein. In methods and uses of the invention, such polypeptides, proteins and peptides encoded by the polynucleotide sequences can be but are not required to be identical to the endogenous protein that is defective, or whose expression is insufficient, or deficient in the treated mammal.

Invention adeno-associated virus (AAV) serotype AAV-Rh74 and related AAV variants such as AAV-Rh74 variants (e.g., capsid variants such as RHM4-1, RHM4-1, RHM15-1, RHM15-2, RHM15-3/RHM15-5, RHM15-4 and RHM15-6), can be used to introduce/deliver polynucleotides stably or transiently into cells and progeny thereof. The term "transgene" is used herein to conveniently refer to such a heterologous polynucleotide that has been introduced into a cell or organism. Transgenes include any polynucleotide, such as a gene that encodes a polypeptide or protein, a polynucleotide that is transcribed into an inhibitory polynucleotide, or a polynucleotide that is not transcribed (e.g., lacks a expression control element, such as a promoter that drives transcription).

For example, in a cell having a transgene, the transgene has been introduced/transferred by way of vector, such as AAV, "transformation" of the cell. The terms "transform," and "transfect" refer to introduction of a molecule such as a polynucleotide into a cell or host organism.

A cell into which the transgene has been introduced is referred to as a "transformed cell" or "transformant"

Accordingly, a "transformed" or "transfected" cell (e.g., in a mammal, such as a cell or tissue or organ cell), means a genetic change in a cell following incorporation of an exogenous molecule, for example, a polynucleotide or protein (e.g., a transgene) into the cell. Thus, a "transfected" or "transformed" cell is a cell into which, or a progeny thereof in which an exogenous molecule has been introduced, for example. The cell(s) can be propagated and the introduced protein expressed, or nucleic acid transcribed. For gene therapy uses and methods, a transformed cell can be in a subject.

The introduced polynucleotide may or may not be integrated into nucleic acid of the recipient cell or organism. If an introduced polynucleotide becomes integrated into the nucleic acid (genomic DNA) of the recipient cell or organism it can be stably maintained in that cell or organism and further passed on to or inherited by progeny cells or organisms of the recipient cell or organism. Finally, the introduced nucleic acid may exist in the recipient cell or host organism only transiently.

Cells that may be transformed include a cell of any tissue or organ type, of any origin (e.g., mesoderm, ectoderm or endoderm). Non-limiting examples of cells include liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (e.g., retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells. Additional examples include stem cells, such as pluripotent or multipotent progenitor cells that develop or differentiate into liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells.

A "therapeutic molecule" in one embodiment is a peptide or protein that may alleviate or reduce symptoms that result from an absence or defect in a protein in a cell or subject. Alternatively, a "therapeutic" peptide or protein encoded by a transgene is one that confers a benefit to a subject, e.g., to correct a genetic defect, to correct a gene (expression or functional) deficiency, or an anti-cancer effect.

Particular non-limiting examples of heterologous polynucleotides encoding gene products (e.g., therapeutic proteins) which are useful in accordance with the invention include, but are not limited to: genes that comprise or encode CFTR (cystic fibrosis transmembrane regulator protein), a blood coagulation (clotting) factor (Factor XIII, Factor IX, Factor X, Factor VIII, Factor VIIa, protein C etc.) including gain of function blood coagulation factors, an antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor (e.g., insulin-like growth factors 1 and 2, platelet derived growth factor, epidermal growth factor, nerve growth factor, neurotrophic factor-3 and -4, brain-derived neurotrophic factor, glial derived growth factor, transforming growth factor α and β, etc.), a cytokine (e.g., α-interferon, β-interferon, interferon-γ, interleukin-2, interleukin-4, interleukin 12, granulocyte-macrophage colony stimulating factor, lymphotoxin, etc.), a suicide gene product (e.g., herpes simplex virus thymidine kinase, cytosine deaminase, diphtheria toxin, cytochrome P450, deoxycytidine kinase, tumor necrosis factor, etc.), a drug resistance protein (e.g, that provides resistance to a drug used in cancer therapy), a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitopes [de Groot et al., Blood 2008 Oct. 15; 112(8):3303], or hCDR1 [Sharabi et al., Proc Natl Acad Sci USA. 2006 Jun. 6; 103(23):8810-5], insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USH1C (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, gene deficiencies causative of lysosomal storage diseases (e.g., sulfatases, N-acetylglucosamine-1-phosphate transferase, cathepsin A, GM2-AP, NPC1, VPC2, Sphingolipid activator proteins, etc.), one or more zinc finger nucleases for genome editing, or donor sequences used as repair templates for genome editing.

Further non-limiting examples of heterologous polynucleotides encoding gene products (e.g., therapeutic proteins) which are useful in accordance with the invention include those that may be used in the treatment of a disease or disorder including, but not limited to, cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), and diseases of solid organs (e.g., brain, liver, kidney, heart).

All mammalian and non-mammalian forms of polynucleotides encoding gene products, including the non-limiting genes and proteins disclosed herein are expressly included, either known or unknown. Thus, the invention includes genes and proteins from non-mammals, mammals other than humans, and humans, which genes and proteins function in a substantially similar manner to the human genes and proteins described herein. A non-limiting example of non-mammalian gene is a Fok nuclease domain, which is bacterial in origin. Non-limiting examples of mammalian non-human FIX sequences are described in Yoshitake et al., 1985, supra; Kurachi et al., 1995, supra; Jallat et al., 1990, supra; Kurachi et al., 1982, Proc. Natl. Acad. Sci. USA 79:6461-6464; Jaye et al., 1983, Nucl. Acids Res. 11:2325-2335; Anson et al., 1984, EMBO J. 3: 1053-1060; Wu et al., 1990, Gene 86:275-278; Evans et al., Proc Natl Acad Sci USA 86:10095 (1989), Blood 74:207-212; Pendurthi et al., 1992, Thromb. Res. 65:177-186; Sakar et al., 1990, Genom-

*ics* 1990, 6:133-143; and, Katayama et al., 1979, *Proc. Natl. Acad. Sci. USA* 76:4990-4994.

As set forth herein, heterologous polynucleotide sequences (transgenes) include inhibitory and antisense nucleic acid sequences Inhibitory, antisense, siRNA (small interfering RNA), miRNA (micro RNA), shRNA (small hairpin RNA), RNAi and antisense oligonucleotides can modulate expression of a target gene. Such molecules include those able to inhibit expression of a target gene involved in mediation of a disease process, thereby reducing, inhibiting or alleviating one or more symptoms of a disease.

Antisense includes single, double or triple stranded polynucleotides and peptide nucleic acids (PNAs) that bind RNA transcript or DNA (e.g., genomic DNA). Oligonucleotides derived from the transcription initiation site of a target gene, e.g., between positions −10 and +10 from the start site, are another particular example. Triplex forming antisense can bind to double strand DNA thereby inhibiting transcription of the gene. "RNAi" is the use of single or double stranded RNA sequences for inhibiting gene expression (see, e.g., Kennerdell et al., *Cell* 95:1017 (1998); and Fire et al., *Nature,* 391:806 (1998)). Double stranded RNA sequences from a target gene coding region may therefore be used to inhibit or prevent gene expression/transcription in accordance with the methods and uses of the invention. Antisense and RNAi can be produced based upon nucleic acids encoding target gene sequences (e.g., huntingtin, or HTT), such as nucleic acid encoding mammalian and human HTT. For example, a single or double stranded nucleic acid (e.g., RNA) can target HTT transcript (e.g., mRNA).

A "siRNA" refers to a therapeutic molecule involved in the RNA interference process for a sequence-specific post-transcriptional gene silencing or gene knockdown. siRNAs have homology with the sequence of the cognate mRNA of the targeted gene. Small interfering RNAs (siRNAs) can be synthesized in vitro or generated by ribonuclease III cleavage from longer dsRNA and are the mediators of sequence-specific mRNA degradation. siRNA or other such nucleic acids of the invention can be chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting mRNA of a target gene may be between 15-50 nucleotides in length, and more typically about 20-30 nucleotides in length. Such nucleic acid molecules can be readily incorporated into the viral vectors disclosed herein using conventional methods known to one of skill in the art.

Particular non-limiting examples of genes (e.g., genomic DNA) or transcript of a pathogenic gene (e.g., RNA or mRNA) that may be targeted with inhibitory nucleic acid sequences in accordance with the invention include, but are not limited to: genes associated with polynucleotide repeat diseases such as huntingtin (HTT) gene, a gene associated with dentatorubropallidolusyan atropy (e.g., atrophin 1, ATN1); androgen receptor on the X chromosome in spinobulbar muscular atrophy, human Ataxin-1, -2, -3, and -7, $Ca_v2.1$ P/Q voltage-dependent calcium channel is encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercoloesterolemia; HIV Tat, human immunodeficiency virus transactivator of transcription gene, in HIV infection; HIV TAR, HIV TAR, human immunodeficiency virus transactivator response element gene, in HIV infection; C-C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DAN damage-inducible transcript 4 protein, in diabetic macular edema (DME) or age-related macular degeneration; vascular endothelial growth factor receptor I (VEGFR1) in age-related macular degeneration or choroidal neivascularization, caspase 2 in non-arteritic ischaemic optic neuropathy; Keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and HLA-allele specific in transplant; or mutant rhodopsin gene (RHO) in autosomal dominantly inherited retinitis pigmentosa (adRP).

Polynucleotides, polypeptides and subsequences thereof include modified and variant forms. As used herein, the terms "modify" or "variant" and grammatical variations thereof, mean that a polynucleotide, polypeptide or subsequence thereof deviates from a reference sequence. Modified and variant sequences may therefore have substantially the same, greater or less activity or function than a reference sequence, but at least retain partial activity or function of the reference sequence.

Accordingly, the invention also includes naturally and non-naturally occurring variants. Such variants include AAV-Rh74 variants such as AAV-Rh74 capsid variants. Particular examples of such AAV-Rh74 capsid variants include RHM 15-1, RHM 15-2, RHM 15-3, RHM 15-4, RHM 15-5, RHM 15-6 and RHM4-1 (see, for example, FIG. 5).

Such variants also include gain and loss of function variants. For example, wild type human FIX DNA sequences, which protein variants or mutants retain activity, or are therapeutically effective, or are comparably or even more therapeutically active than invariant human FIX in the methods and uses of the invention. In a particular example, collagen IV serves to trap FIX, meaning that when introduced into the muscle tissue of a mammal some of the FIX is not available for participation in blood coagulation because it is retained in the interstitial spaces in the muscle tissue. A mutation in the sequence of FIX that results in a protein with reduced binding to collagen IV (e.g., loss of function) is a mutant useful in the methods of the invention, for example, for treatment of hemophilia. An example of such a mutant human FIX gene encodes a human FIX protein with the amino acid alanine in place of lysine in the fifth amino acid position from the beginning of the mature protein.

Non-limiting examples of modifications include one or more nucleotide or amino acid substitutions (e.g., 1-3, 3-5, 5-10, 10-15, 15-20, 20-25, 25-30, 30-40, 40-50, 50-100, or more nucleotides or residues), such as an arginine for a lysine residue (e.g., one or more arginine substitution of a lysine as set forth in any of RHM4-1, RHM15-1, RHM15-2, RHM15-3/RHM15-5, RHM15-4 and RHM15-6) additions (e.g., insertions or 1-3, 3-5, 5-10, 10-15, 15-20, 20-25, 25-30, 30-40, 40-50, 50-100, or more nucleotides or residues) and deletions (e.g., subsequences or fragments) of a reference sequence. In particular embodiments, a modified or variant sequence retains at least part of a function or an activity of unmodified sequence. Such modified forms and variants can have less than, the same, or greater, but at least a part of, a function or activity of a reference sequence, for example, as described herein.

A variant can have one or more non-conservative or a conservative amino acid sequence differences or modifications, or both. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine (e.g., RHM15-1, RHM15-2, RHM15-3/RHM15-5, RHM15-4 and RHM15-6), glutamic for aspartic acids, or glutamine for asparagine, serine for threonine, and the like. Particular examples of conservative substitutions include the substitution of a hydrophobic residue such as isoleucine, valine, leucine or methionine for another, or the substitution of a polar residue for another, such as the substitution of arginine for lysine, glutamic for aspartic acids, or glutamine for asparagine, and the like. For example, conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

Accordingly, the invention includes gene and protein variants (e.g., of polynucleotides encoding proteins described herein) which retain one or more biological activities (e.g., function in blood clotting, etc.). Such variants of proteins or polypeptides include proteins or polypeptides which have been or may be modified using recombinant DNA technology such that the protein or polypeptide possesses altered or additional properties, for example, variants conferring enhanced protein stability in plasma or enhanced activity of the protein. Variants can differ from a reference sequence, such as naturally occurring polynucleotides, proteins or peptides.

At the nucleotide sequence level, a naturally and non-naturally occurring variant gene will typically be at least about 50% identical, more typically about 70% identical, even more typically about 80% identical (90% or more identity) to the reference gene. At the amino acid sequence level, a naturally and non-naturally occurring variant protein will typically be at least about 70% identical, more typically about 80% identical, even more typically about 90% or more identity to the reference protein, although substantial regions of non-identity are permitted in non-conserved regions (e.g., less, than 70% identical, such as less than 60%, 50% or even 40%). In other embodiments, the sequences have at least 60%, 70%, 75% or more identity (e.g., 80%, 85% 90%, 95%, 96%, 97%, 98%, 99% or more identity) to a reference sequence. Procedures for the introduction of nucleotide and amino acid changes in a polynucleotide, protein or polypeptide are known to the skilled artisan (see, e.g., Sambrook et al., *Molecular Cloning: A Laboratory Manual* (2007)).

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid) sequences, often containing corrections for missing or additional bases or amino acids (gaps) as compared to a reference sequence The identity can extend over the entire sequence length or a portion of the sequence. In particular aspects, the length of the sequence sharing the percent identity is 2, 3, 4, 5 or more contiguous polynucleotide or amino acids, e.g., 6, 7, 8, 9, 10, 11, 12, 13, 14, 15, 16, 17, 18, 19, 20, etc. contiguous amino acids. In additional particular aspects, the length of the sequence sharing identity is 20 or more contiguous polynucleotide or amino acids, e.g., 20, 21, 22, 23, 24, 25, 26, 27, 28, 29, 30, 31, 32, 33, 34, 35, etc. contiguous amino acids. In further particular aspects, the length of the sequence sharing identity is 35 or more contiguous polynucleotide or amino acids, e.g., 35, 36, 37, 38, 39, 40, 41, 42, 43, 44, 45, 45, 47, 48, 49, 50, etc., contiguous amino acids. In yet further particular aspects, the length of the sequence sharing identity is 50 or more contiguous polynucleotide or amino acids, e.g., 50-55, 55-60, 60-65, 65-70, 70-75, 75-80, 80-85, 85-90, 90-95, 95-100, 100-110, etc. contiguous polynucleotide or amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) between two sequences can be ascertained using a computer program and mathematical algorithm. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Polynucleotides include additions and insertions, for example, heterologous domains. An addition (e.g., heterologous domain) can be a covalent or non-covalent attachment of any type of molecule to a composition. Typically additions and insertions (e.g., a heterologous domain) confer a complementary or a distinct function or activity.

Additions and insertions include chimeric and fusion sequences, which is a polynucleotide or protein sequence having one or more molecules not normally present in a reference native (wild type) sequence covalently attached to the sequence. The terms "fusion" or "chimeric" and grammatical variations thereof, when used in reference to a molecule means that a portions or part of the molecule contains a different entity distinct (heterologous) from the molecule as they do not typically exist together in nature. That is, for example, one portion of the fusion or chimera, includes or consists of a portion that does not exist together in nature, and is structurally distinct.

The term "vector" refers to a plasmid, virus (e.g., AAV vector), cosmid, or other vehicle that can be manipulated by insertion or incorporation of a polynucleotide. Such vectors can be used for genetic manipulation (i.e., "cloning vectors"), to introduce/transfer polynucleotides into cells, and to transcribe or translate the inserted polynucleotide in cells. A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

As used herein, the term "recombinant," as a modifier of viral vector, such as recombinant AAV vectors, as well as a modifier of sequences such as recombinant polynucleotides and polypeptides, means that the compositions (e.g., AAV or sequences) have been manipulated (i.e., engineered) in a fashion that generally does not occur in nature. A particular example of a recombinant vector, such as an AAV vector would be where a polynucleotide that is not normally present in the wild-type viral (e.g., AAV) genome is inserted within the viral genome. For example, an example of a recombinant polynucleotide would be where a heterologous polynucleotide (e.g., gene) encoding a protein is cloned into a vector, with or without 5', 3' and/or intron regions that the gene is normally associated within the viral (e.g., AAV) genome. Although the term "recombinant" is not always used herein in reference to viral vectors, such as AAV vectors, as well as sequences such as polynucleotides and polypeptides, recombinant forms of AAV, and sequences including polynucleotides and polypeptides, are expressly included in spite of any such omission.

A recombinant vector "genome" (e.g., an AAV vector genome) can be encapsidated or packaged into a virus (also referred to herein as a "particle" or "virion") for subsequent infection (transduction or transformation) of a cell, ex vivo, in vitro or in vivo. Where a recombinant AAV vector genome is encapsidated or packaged into an AAV particle, the particle can be referred to as a "rAAV." Such particles or virions will typically include proteins that encapsidate or package the vector genome. Particular examples include viral capsid and envelope proteins, and in the case of AAV, AAV capsid proteins.

For a recombinant plasmid, a vector "genome" refers to the portion of the recombinant plasmid sequence that is ultimately packaged or encapsidated to form a viral particle. In case where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the 'plasmid backbone,' which is important for cloning and amplification of the plasmid, a process that is needed for propagation and recombinant virus production, but is not itself packaged or encapsidated into virus (e.g., AAV) particles.

Thus, a vector "genome" refers to the portion of the vector plasmid that is packaged or encapsidated by virus (e.g., AAV), and which contains a heterologous polynucleotide sequence. The non vector genome portion of the recombinant plasmid includes the backbone that is important for cloning and amplification of the plasmid, but is not itself packaged or encapsidated by virus (e.g., AAV).

A viral vector is derived from or based upon one or more nucleic acid elements that comprise a viral genome. Particular viral vectors include parvovirus vectors, such as adeno-associated virus (AAV) vectors.

Recombinant vector sequences are manipulated by insertion or incorporation of a polynucleotide. As disclosed herein, a vector plasmid generally contains at least an origin of replication for propagation in a cell and one or more expression control elements.

Vector sequences including AAV vectors can include one or more "expression control elements." Typically, expression control elements are nucleic acid sequence(s) that influence expression of an operably linked polynucleotide. Control elements, including expression control elements as set forth herein such as promoters and enhancers, present within a vector are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis but may also act in trans.

Expression control can be effected at the level of transcription, translation, splicing, message stability, etc. Typically, an expression control element that modulates transcription is juxtaposed near the 5' end of the transcribed polynucleotide (i.e., "upstream"). Expression control elements can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, 5000 to 10,000 or more nucleotides from the polynucleotide), even at considerable distances. Nevertheless, owing to the polynucleotide length limitations, for AAV vectors, such expression control elements will typically be within 1 to 1000 nucleotides from the polynucleotide.

Functionally, expression of operably linked heterologous polynucleotide is at least in part controllable by the element (e.g., promoter) such that the element modulates transcription of the polynucleotide and, as appropriate, translation of the transcript. A specific example of an expression control element is a promoter, which is usually located 5' of the transcribed sequence. Another example of an expression control element is an enhancer, which can be located 5', 3' of the transcribed sequence, or within the transcribed sequence.

A "promoter" as used herein can refer to a DNA sequence that is located adjacent to a polynucleotide sequence that encodes a recombinant product. A promoter is typically operatively linked to an adjacent sequence, e.g., heterologous polynucleotide. A promoter typically increases an amount expressed from a heterologous polynucleotide as compared to an amount expressed when no promoter exists.

An "enhancer" as used herein can refer to a sequence that is located adjacent to the heterologous polynucleotide Enhancer elements are typically located upstream of a promoter element but also function and can be located downstream of or within a DNA sequence (e.g., a heterologous polynucleotide). Hence, an enhancer element can be located 100 base pairs, 200 base pairs, or 300 or more base pairs upstream or downstream of a heterologous polynucleotide. Enhancer elements typically increase expressed of a heterologous polynucleotide above increased expression afforded by a promoter element.

Expression control elements (e.g., promoters) include those active in a particular tissue or cell type, referred to herein as a "tissue-specific expression control elements/ promoters." Tissue-specific expression control elements are typically active in specific cell or tissue (e.g., liver, brain, central nervous system, spinal cord, eye, retina, bone, muscle, lung, pancreas, heart, kidney cell, etc.). Expression control elements are typically active in these cells, tissues or organs because they are recognized by transcriptional activator proteins, or other regulators of transcription, that are unique to a specific cell, tissue or organ type.

For instance, if expression in skeletal muscle is desired, a promoter active in muscle may be used. These include promoters from genes encoding skeletal α-actin, myosin light chain 2A, dystrophin, muscle creatine kinase, as well as synthetic muscle promoters with activities higher than naturally-occurring promoters (see, e.g., Li, et al., *Nat. Biotech.* 17:241-245 (1999)). Examples of promoters that are tissue-specific for liver are albumin, Miyatake, et al. *J. Virol.*, 71:5124-32 (1997); hepatitis B virus core promoter, Sandig, et al., *Gene Ther.* 3:1002-9 (1996); alpha-fetoprotein (AFP), Arbuthnot, et al., *Hum. Gene. Ther.*, 7:1503-14 (1996)], bone (osteocalcin, Stein, et al., *Mol. Biol. Rep.*, 24:185-96 (1997); bone sialoprotein, Chen, et al., *J. Bone Miner. Res.* 11:654-64 (1996)), lymphocytes (CD2, Hansal, et al., *J. Immunol.*, 161:1063-8 (1998); immunoglobulin heavy chain; T cell receptor a chain), neuronal (neuron-specific enolase (NSE) promoter, Andersen, et al., *Cell. Mol. Neurobiol.*, 13:503-15 (1993); neurofilament light-chain gene, Piccioli, et al., *Proc. Natl. Acad. Sci. USA*, 88:5611-5 (1991); the neuron-specific vgf gene, Piccioli, et al., *Neuron*, 15:373-84 (1995)]; among others.

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al, *Cell*, 41:521-530 (1985)), the SV40 promoter, the dihydrofolate reductase promoter, the cytoplasmic β-actin promoter and the phosphoglycerol kinase (PGK) promoter.

Expression control elements also can confer expression in a manner that is regulatable, that is, a signal or stimuli increases or decreases expression of the operably linked heterologous polynucleotide. A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. A regulatable element that decreases expression of the operably linked polynucleotide in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression. Particular non-limiting examples include zinc-inducible sheep metallothionine (MT) promoter; the steroid hormone-inducible mouse mammary tumor virus (MMTV) promoter; the T7 polymerase promoter system (WO 98/10088); the tetracycline-repressible system (Gossen, et al., *Proc. Natl. Acad. Sci. USA*, 89:5547-5551 (1992)); the tetracycline-inducible system (Gossen, et al., *Science.* 268:1766-1769 (1995); see also Harvey, et al., *Curr. Opin. Chem. Biol.* 2:512-518 (1998)); the RU486-inducible system (Wang, et al., *Nat. Biotech.* 15:239-243 (1997) and Wang, et al., *Gene Ther.* 4:432-441 (1997)]; and the rapamycin-inducible system (Magari, et al., *J. Clin. Invest.* 100:2865-2872 (1997); Rivera, et al., *Nat. Medicine.* 2:1028-1032 (1996)). Other regulatable control elements which may be useful in this context are those which are regulated by a specific physiological state, e.g., temperature, acute phase.

Expression control elements also include the native element(s) for the heterologous polynucleotide. A native control element (e.g., promoter) may be used when it is desired that expression of the heterologous polynucleotide should mimic the native expression. The native element may be used when expression of the heterologous polynucleotide is to be regulated temporally or developmentally, or in a tissue-specific manner, or in response to specific transcriptional stimuli. Other native expression control elements, such as introns, polyadenylation sites or Kozak consensus sequences may also be used.

As used herein, the term "operable linkage" or "operably finked" refers to a physical or functional juxtaposition of the components so described as to permit them to function in their intended manner. In the example of an expression control element in operable linkage with a polynucleotide, the relationship is such that the control element modulates expression of the nucleic acid. More specifically, for example, two DNA sequences operably finked means that the two DNAs are arranged (cis or trans) in such a relationship that at least one of the DNA sequences is able to exert a physiological effect upon the other sequence.

Vectors including AAV vectors can include still additional nucleic acid elements. These elements include, without limitation one or more copies of an AAV ITR sequence, a promoter/enhancer element, a transcription termination signal, 5' or 3' untranslated regions (e.g., polyadenylation sequences) which flank a polynucloetide sequence, or all or a portion of intron I. Such elements also optionally include a transcription termination signal. A particular non-limiting example of a transcription termination signal is the SV40 transcription termination signal.

As disclosed herein, AAV vectors typically accept inserts of DNA having a defined size range which is generally about 4 kb to about 5.2 kb, or slightly more. Thus, for shorter sequences, inclusion of a stuffer or filler in the insert fragment in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. In particular embodiments of an AAV vector, a heterologous polynucleotide sequence has a length less than 4.7 Kb and the filler or stuffer polynucleotide sequence has a length that when combined (e.g., inserted into a vector) with the heterologous polynucleotide sequence has a total length between about 3.0-5.5 Kb, or between about 4.0-5.0 Kb, or between about 4.3-4.8 Kb.

An intron can also function as a filler or stuffer polynucleotide sequence in order to achieve a length for AAV vector packaging into a virus particle. Introns and intron fragments (e.g. portion of intron I of FIX) that function as a filler or stuffer polynucleotide sequence also can enhance expression. For example, inclusion of an intron element may enhance expression compared with expression in the absence of the intron element (Kurachi et al., 1995, supra).

The use of introns is not limited to the inclusion of FIX intron I sequences, but also include other introns, which introns may be associated with the same gene (e.g., where the heterologous polynucleotide encodes FIX, the intron is derived from an intron present in the FIX genomic sequence) or associated with a completely different gene or other DNA sequence. Accordingly, other untranslated (non-protein encoding) regions of nucleic acid, such as introns found in genomic sequences from cognate (related) genes (the heterologous polynucleotide sequence encodes all or a portion of same protein encoded by the genomic sequence) and non-cognate (unrelated) genes (the heterologous polynucleotide sequence encodes a protein that is distinct from the protein encoded by the genomic sequence) can also function as filler or stuffer polynucleotide sequences in accordance with the invention.

A "portion of intron I" as used herein, is meant region of intron I having a nucleotide length of from about 0.1 kb to about 1.7 kb, which region enhances expression of FIX, typically by about 1.5-fold or more on a plasmid or viral vector template when compared with expression of FIX in the absence of a portion of intron I. A more specific portion is a 1.3 kb portion of intron 1.

The term "oligonucleotide" as used herein refers to sequences, primers and probes defined as a nucleic acid molecule comprised of two or more ribo- or deoxyribonucleotides, typically more than three. The exact size of the oligonucleotide will depend on various factors and on the particular application and use of the oligonucleotide, but typically an oligonucleotide has a length between about 5-50 nucleotides.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-30 or more nucleotides in length. The primer must be of sufficient complementarity to the desired template to prime the synthesis of the desired extension product, that is, to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188.

The phrase "specifically hybridize" refers to the association between two single-stranded nucleic acid molecules of sufficiently complementary sequence to permit hybridization under predetermined conditions generally used in the art (sometimes termed "substantially complementary"). In particular, the term refers to hybridization of two polynucleotide sequences with substantially complementary sequences, to the substantial exclusion of hybridization with other single-stranded non-complementary nucleic acid sequences.

A "selectable marker gene" refers to a gene that when expressed confers a selectable phenotype, such as antibiotic resistance (e.g., kanamycin), on a transformed cell. A "reporter" gene is one that provides a detectable signal. A non-limiting example of a reporter gene is the luciferase gene.

Polynucleotides and polypeptides including modified forms can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Polynucleotides and polypeptides including modified forms can also be produced by chemical synthesis using methods to the skilled artisan, for example, an automated synthesis apparatus (see, e.g., Applied Biosystems, Foster City, Calif.). Peptides can be synthesized, whole or in part, using chemical methods (see, e.g., Caruthers (1980). *Nucleic Acids Res. Symp. Ser.* 215; Horn (1980); and Banga, A. K., Therapeutic Peptides and Proteins, Formulation, Processing and Delivery Systems (1995) *Technomic Publishing Co.*, Lancaster, Pa.). Peptide synthesis can be performed using various solid phase techniques (see, e.g., Roberge Science 269:202 (1995); *Merrifield, Methods Enzymol.* 289:3 (1997)) and automated synthesis may be achieved, e.g., using the ABI 431A Peptide Synthesizer (Perkin Elmer) in accordance with the manufacturer's instructions.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude combinations produced by the hand of man, for example, a recombinant vector (e.g., AAV) sequence, or virus particle (e.g., AAV-Rh74 vector or related AAV vector such as AAV-Rh74 variants such as capsid variants (e.g., RHM4-1)) that packages or encapsidates a vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

Methods and uses of the invention provide a means for delivering (transducing) heterologous polynucleotides (transgenes) into a broad range of host cells, including both dividing and non-dividing cells. The recombinant vector (e.g., AAV) sequences, plasmids, vector genomes, recombinant virus particles (e.g., AAV-Rh74 or related AAV such as AAV-Rh74 variants such as capsid variants (e.g., RHM4-1)), methods, uses and pharmaceutical formulations of the invention are additionally useful in a method of administering a protein, peptide or nucleic acid to a subject in need thereof, as a method of treatment. In this manner, the protein, peptide or nucleic acid may thus be produced in vivo in a subject. The subject may benefit from or be in need of the protein, peptide or nucleic acid because the subject has a deficiency of the protein, peptide or nucleic acid, or because the production of the protein, peptide or nucleic acid in the subject may impart some therapeutic effect, as a method of treatment or otherwise. Alternatively, it may be desirable to inhibit or reduce expression or production of a target gene involved in a disease process, e.g., for the treatment of a neurodegenerative disease, cancer or atherosclerosis, for example to achieve a therapeutic effect.

In general, recombinant vector (e.g., AAV) sequences, plasmids, vector genomes, recombinant virus particles (e.g., AAV-Rh74 or related AAV such as AAV-Rh74 variants such as capsid variants (e.g., RHM4-1)), methods and uses may be used to deliver any heterologous polynucleotide (transgene) with a biological effect to treat or ameliorate one or more symptoms associated with any disorder related to insufficient or undesirable gene expression. Recombinant vector (e.g., AAV) sequences, plasmids, vector genomes, recombinant virus particles (e.g., AAV-Rh74 or related AAV such as AAV-Rh74 variants such as capsid variants (e.g., RHM4-1)) particles, methods and uses may be used to provide therapy for various disease states.

There are a number of inherited diseases in which defective genes are known and have been cloned. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus, recombinant vector (e.g., AAV) sequences, plasmids, vector genomes, recombinant virus particles (e.g., AAV-Rh74 vectors or related AAV vectors such as AAV-Rh74 variants such as capsid variants (e.g., RHM4-1)), methods and uses permit the treatment of genetic diseases. As used herein, a disease state is treated by partially or wholly remedying the deficiency or imbalance that causes the disease or makes it more severe. The use of site-specific integration of nucleic acid sequences to cause mutations or to correct defects is also possible.

Illustrative disease states include, but are not limited to: cystic fibrosis (and other diseases of the lung), hemophilia A, hemophilia B, thalassemia, anemia and other blood coagulation disorders, AIDs, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, Pompe's disease, congestive heart failure, retinal degenerative diseases (choroideremia, Leber's congenital amaurosis, and other diseases of the eye), diseases of solid organs (e.g., brain, liver, kidney, heart), and the like.

In accordance with the invention, treatment methods and uses are provided that include invention recombinant vectors (e.g., AAV), vector genomes, recombinant virus particles (e.g., AAV-Rh74 vectors or related AAV vectors such as AAV-Rh74 variants such as capsid variants (e.g., RHM4-1)) and invention viral particles (e.g., AAV-Rh74 or related AAV such as AAV-Rh74 variants such as capsid variants (e.g., RHM4-1)) including vector genomes. Methods and uses of the invention are broadly applicable to diseases amenable to treatment by introducing a gene encoding a protein, or increasing or stimulating gene expression or function, e.g., gene addition or replacement. Methods and uses of the invention are also broadly applicable to diseases amenable to treatment by reducing or decreasing gene expression or function, e.g., gene knockout or reduction of gene expression (gene knockdown).

Non-limiting particular examples of diseases treatable in accordance with the invention include those set forth herein as well as a lung disease (e.g., cystic fibrosis), a blood coagulation or bleeding disorder (e.g., hemophilia A or hemophilia B with or without inhibitors), thalassemia, a blood disorder (e.g., anemia), Alzheimer's disease, Parkinson's disease, Huntington's disease, amyotrophic lateral sclerosis (ALS), epilepsy, lysosomal storage diseases, a copper or iron accumulation disorders (e.g., Wilson's or Menkes disease) lysosomal acid lipase deficiency, a neurological or neurodegenerative disorder, cancer, type 1 or type 2 diabetes, Gaucher's disease, Hurler's disease, adenosine deaminase deficiency, a metabolic defect (e.g., glycogen storage diseases), a retinal degenerative disease (such as RPE65 deficiency or defect, choroideremia, and other diseases of the eye), and a disease of a solid organ (e.g., brain, liver, kidney, heart).

In addition, invention recombinant vectors (e.g., AAV), vector genomes, recombinant virus particles (e.g., AAV-Rh74 vectors or related AAV vectors such as AAV-Rh74 variants such as capsid variants (e.g., RHM4-1)), methods and uses may be employed to deliver nucleic acids encoding monoclonal antibodies or fragments thereof to provide beneficial biological effects to treat or ameliorate the symptoms associated with cancers, infectious diseases, and autoimmune diseases such as rheumatoid arthritis.

In one embodiment, a method or use of the invention includes: (a) providing a viral particle (e.g., AAV-Rh74 or related AAV such as AAV-Rh74 capsid variants (e.g., RHM4-1)) comprising a vector genome, the vector genome comprising a heterologous polynucleotide sequence (and, optionally a filler/stuffer polynucleotide sequence), wherein the heterologous polynucleotide sequence is operably linked to an expression control element conferring transcription of said polynucleotide sequence; and (b) administering an amount of the viral particle to the mammal such that said heterologous polynucleotide is expressed in the mammal.

In another embodiment, a method or use of the invention includes delivering or transferring a heterologous polynucleotide sequence into a mammal or a cell of a mammal, by administering a viral (e.g., AAV) particle (e.g., AAV-Rh74 or related AAV such as AAV-Rh74 variants such as capsid variants (e.g., RHM4-1)) or plurality of viral (e.g., AAV) particles (e.g., AAV-Rh74 or related AAV such as AAV-Rh74 variants such as capsid variants (e.g., RHM4-1)) comprising a vector genome, the vector genome comprising the heterologous polynucleotide sequence (and optionally a filler/stuffer polynucleotide sequence) to a mammal or a cell of a mammal, thereby delivering or transferring the heterologous polynucleotide sequence into the mammal or cell of the mammal.

In a further embodiment, a method or use of the invention for treating a mammal deficient in need of protein expression or function includes providing a viral (e.g., AAV) particle (e.g., AAV-Rh74 or related AAV such as AAV-Rh74 variants such as capsid variants (e.g., RHM4-1)) or plurality of viral (e.g., AAV) particles (e.g., AAV-Rh74 or related AAV such as AAV-Rh74 variants such as capsid variants (e.g., RHM4-1)) comprising a vector genome, the vector genome comprising a heterologous polynucleotide sequence (and optionally a filler/stuffer polynucleotide sequence); and administering the viral particle or plurality of viral particles to the mammal, where the heterologous polynucleotide sequence encodes a protein expressed in the mammal, or where the heterologous polynucleotide sequence encodes an inhibitory sequence or protein that reduces expression of an endogenous protein in the mammal.

In particular aspects of invention methods and uses disclosed herein, expression of the heterologous polynucleotide encodes a protein or inhibitory nucleic acid that provides a therapeutic benefit to the mammal (e.g., human) In further particular aspects, a filler/stuffer polynucleotide sequence is included in the vector sequence such that the combined length with the heterologous polynucleotide sequence has a total length of between about 3.0-5.5 Kb, or between about 4.0-5.0 Kb, or between about 4.3-4.8 Kb.

Methods and uses of the invention include treatment methods, which result in any therapeutic or beneficial effect. In various invention methods and uses, further included are inhibiting, decreasing or reducing one or more adverse (e.g., physical) symptoms, disorders, illnesses, diseases or complications caused by or associated with the disease, such as reduced blood clotting time, reduced administration dosage of supplemental clotting factor protein.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Compositions, such as vector genomes, recombinant virus particles (e.g., AAV-Rh74 vectors or related AAV vectors such as AAV-Rh74 variants such as capsid variants (e.g., RHM4-1)) including vector genomes, and methods and uses of the invention, can be administered in a sufficient or effective amount to a subject in need thereof. An "effective amount" or "sufficient amount" refers to an amount that provides, in single or multiple doses, alone or in combination, with one or more other compositions (therapeutic agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

The vector genome or virus particle (e.g., AAV, such as AAV-Rh74 vector or related AAV vector such as AAV-Rh74 variants such as capsid variants (e.g., RHM4-1)) dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can readily determine a virion dose range to treat a patient having a particular disease or disorder based on the aforementioned factors, as well as other factors. Generally, doses will range from at least $1 \times 10^8$, or more, for example, $1 \times 10^9$, $1 \times 10^{10}$, $1 \times 10^{11}$, $1 \times 10^{12}$, $1 \times 10^{13}$ or $1 \times 10^{14}$, or more, vector genomes per kilogram (vg/kg) of the weight of the subject, to achieve a therapeutic effect.

Using hemophilia as an example, generally speaking, it is believed that, in order to achieve a therapeutic effect, a blood coagulation factor concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a blood coagulation factor concentration greater than 5% of normal is needed. With respect to treating such a hemophilic subject, a typical dose is at least $1 \times 10^{10}$ vector genomes (vg) per kilogram (vg/kg) of the weight of the subject, or between about $1 \times 10^{10}$ to $1 \times 10^{11}$ vg/kg of the weight of the subject, or between about $1 \times 10^{11}$ to $1 \times 10^{12}$ vg/kg of the weight of the subject, or between about $1 \times 10^{12}$ to $1 \times 10^{13}$ vg/kg of the weight of the subject, to achieve a desired therapeutic effect.

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein for treatment of a clotting disorder (e.g., hemophilia A or B).

An effective amount or a sufficient amount need not be effective in each and every subject treated, or a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use. Thus, appropriate amounts will depend upon the condition treated, the therapeutic effect desired, as well as the individual subject (e.g., the bioavailability within the subject, gender, age, etc.).

The term "ameliorate" means a detectable or measurable improvement in a subject's disease or symptom thereof, or an underlying cellular response. A detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

Thus, a successful treatment outcome can lead to a "therapeutic effect," or "benefit" of decreasing, reducing, inhibiting, suppressing, limiting, controlling or preventing the occurrence, frequency, severity, progression, or duration of a disease, or one or more adverse symptoms or underlying causes or consequences of the disease in a subject. Treatment methods and uses affecting one or more underlying causes of the disease or adverse symptoms are therefore considered to be beneficial. A decrease or reduction in worsening, such as stabilizing the disease, or an adverse symptom thereof, is also a successful treatment outcome.

A therapeutic benefit or improvement therefore need not be complete ablation of the disease, or any one, most or all adverse symptoms, complications, consequences or underlying causes associated with the disease. Thus, a satisfactory endpoint is achieved when there is an incremental improvement in a subject's disease, or a partial decrease, reduction, inhibition, suppression, limit, control or prevention in the occurrence, frequency, severity, progression, or duration, or inhibition or reversal, of the disease (e.g., stabilizing one or more symptoms or complications), over a short or long duration of time (hours, days, weeks, months, etc.). Effectiveness of a method or use, such as a treatment that provides a potential therapeutic benefit or improvement of a disease, can be ascertained by various methods.

Invention methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention, for example, a therapeutic method of treating a subject for a blood clotting disease.

The compound, agent, drug, treatment or other therapeutic regimen or protocol can be administered as a combination composition, or administered separately, such as concurrently or in series or sequentially (prior to or following) delivery or administration of a vector genome or virus (e.g., AAV-Rh74 vector or related AAV vector such as AAV-Rh74 variants such as capsid variants (e.g., RHM4-1)) of the invention. The invention therefore provides combinations in which a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of a vector genome or virus (e.g., AAV-Rh74 vector or related AAV vector such as AAV-Rh74 variants such as capsid variants (e.g., RHM4-1)) of the invention, to a subject. Specific non-limiting examples of combination embodiments therefore include the foregoing or other compound, agent, drug, therapeutic regimen, treatment protocol, process, remedy or composition.

Methods and uses of the invention also include, among other things, methods and uses that result in a reduced need or use of another compound, agent, drug, therapeutic regimen, treatment protocol, process, or remedy. For example, for a blood clotting disease, a method or use of the invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the invention, methods and uses of reducing need or use of another treatment or therapy are provided.

The invention is useful in animals including veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases and others known to those of skill in the art.

As set forth herein, vectors and virus particles (e.g., AAV-Rh74 or related AAV such as AAV-Rh74 variants such as capsid variants (e.g., RHM4-1)) comprising such vectors can be used to provide a protein to a subject where there is an insufficient amount of the protein or a deficiency in a functional gene product (protein), or to provide an inhibitory nucleic acid or protein to a subject who produces an aberrant, partially functional or non-functional gene product (protein) which can lead to disease. Accordingly, subjects appropriate for treatment include those having or at risk of producing an insufficient amount or having a deficiency in a functional gene product (protein), or produce an aberrant, partially functional or non-functional gene product (protein), which can lead to disease. Subjects appropriate for treatment in accordance with the invention also include those having or at risk of producing an aberrant, or defective (mutant) gene product (protein) that leads to a disease such that reducing amounts, expression or function of the aberrant, or defective (mutant) gene product (protein) would lead to treatment of the disease, or reduce one or more symptoms or ameliorate the disease. Target subjects therefore include subjects that have such defects regardless of the disease type, timing or degree of onset, progression, severity, frequency, or type or duration of symptoms.

"Prophylaxis" and grammatical variations thereof mean a method in which contact, administration or in vivo delivery to a subject is prior to disease. Administration or in vivo delivery to a subject can be performed prior to development of an adverse symptom, condition, complication, etc. caused by or associated with the disease. For example, a screen (e.g., genetic) can be used to identify such subjects as candidates for invention methods and uses, but the subject may not manifest the disease. Such subjects therefore include those screened positive for an insufficient amount or a deficiency in a functional gene product (protein), or that produce an aberrant, partially functional or non-functional gene product (protein), which can lead to disease; and subjects that screen positive for an aberrant, or defective (mutant) gene product (protein) that leads to disease, even though such subjects do not manifest symptoms of the disease.

Methods and uses of the invention include delivery and administration systemically, regionally or locally, or by any route, for example, by injection, infusion, orally (e.g., ingestion or inhalation), or topically (e.g., transdermally) Such delivery and administration include intravenously, intramuscularly, intraperitoneally, intradermally, subcutaneously, intracavity, intracranially, transdermally (topical), parenterally, e.g. transmucosally or rectally. Exemplary administration and delivery routes include intravenous (i.v.), intraperitoneal (i.p.), intrarterial, intramuscular, parenteral, subcutaneous, intra-pleural, topical, dermal, intradermal, transdermal, parenterally, e.g. transmucosal, intra-cranial, intra-spinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, intralymphatic.

Doses can vary and depend upon whether the treatment is prophylactic or therapeutic, the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

Methods and uses of the invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the invention can be practiced 1-7, 7-14, 14-21, 21-48 or more days, months or years after a subject has been identified as having the disease targeted for treatment, has one or more symptoms of the disease, or has been screened and is identified as positive as set forth herein.

Recombinant vector (e.g., AAV, such as AAV-Rh74 vector or related AAV vector such as AAV-Rh74 variants such as capsid variants (e.g., RHM4-1)), sequences, plasmids, vector genomes, recombinant virus particles (e.g., AAV, such as AAV-Rh74 vector or related AAV vector such as AAV-Rh74 variants such as capsid variants (e.g., RHM4-1)) and other compositions, agents, drugs, biologics (proteins) can be incorporated into pharmaceutical compositions, e.g., a pharmaceutically acceptable carrier or excipient. Such pharmaceutical compositions are useful for, among other things, administration and delivery to a subject in vivo or ex vivo.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a viral vector or viral particle (e.g., AAV-Rh74 or related AAV such as AAV-Rh74 variants such as capsid variants (e.g., RHM4-1)) or transformed cell to a subject.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the vector genomes, virus particles (e.g., AAV-Rh74 vector or related AAV vector such as AAV-Rh74 variants such as capsid variants (e.g., RHM4-1)) and methods and uses of the invention are known in the art (see, e.g., Remington: The Science and Practice of Pharmacy (2003) 20$^{th}$ ed., Mack Publishing Co., Easton, Pa.; Remington's Pharmaceutical Sciences (1990) 18$^{th}$ ed., Mack Publishing Co., Easton, Pa.; The Merck Index (1996) 12$^{th}$ ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11$^{th}$ ed., Lippincott Williams & Wilkins, Baltimore, Md.; and Poznansky et al., Drug Delivery Systems (1980), R. L. Juliano, ed., Oxford, N.Y., pp. 253-315).

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., AAV) sequences, plasmids, vector genomes, recombinant virus particles (e.g., AAV-Rh74 vector or related AAV vector such as AAV-Rh74 capsid variants (e.g., RHM4-1)), and pharmaceutical compositions thereof can be packaged in single or multiple unit dosage form for ease of administration and uniformity of dosage.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a vector (e.g., AAV) genome or virus particle (e.g., AAV-Rh74 vector or related AAV vector such as AAV-Rh74 variants such as capsid variants (e.g., RHM4-1)) and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., a recombinant vector (e.g., AAV) sequence, plasmid, vector genome, or recombinant virus particle (e.g., AAV-Rh74 vector or related AAV vector such as AAV-Rh74 capsid variants (e.g., RHM4-1)) are an example of a genus of equivalent or similar features.

As used herein, the singular forms "a", "and," and "the" include plural referents unless the context clearly indicates otherwise. Thus, for example, reference to "a polynucleotide" includes a plurality of such polynucleotides, reference to "a vector" includes a plurality of such vectors, and reference to "a virus" or "particle" includes a plurality of such virions/particles.

As used herein, all numerical values or numerical ranges include integers within such ranges and fractions of the values or the integers within ranges unless the context clearly indicates otherwise. Thus, to illustrate, reference to at least 80% identity, includes 81%, 82%, 83%, 84%, 85%, 86%, 87%, 88%, 89%, 90%, 91%, etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 1,000, includes 999, 998, 997, etc. all the way down to the number one (1); and less than 100, includes 99, 98, 97, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as a percentage range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges of 11-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLES

Example 1

This example includes a description of various materials and methods.

Mice:

Male C57BL/6J (WT) mice 8-10 weeks of age, 1=5 per experimental group. The dog is a HB dog from the University of North Carolina Chapel Hill colony carrying a missense mutation in the FIX gene (Evans et al., *Proc Natl Acad Sci USA* 86:10095 (1989)).

AAV Vector Constructs:

The in vivo studies in mice were performed using a construct expressing human FIX under the control of the ApoE-hAAT liver specific promoter. The study in dogs used a nearly identical promoter and the canine FIX transgene.

Gene Transfer Methodology:

All vectors were delivered intravenously. In mice via the tail vein (a volume of 200 microliters per mouse was administered, vector was diluted in PBS). In dogs the vector was delivered via the saphenous vein.

FIX Expression Determination:

ELISA was used to measure FIX levels. In mice, the human FIX ELISA antibody pair (capture and secondary) is from Affinity Biologicals. In dogs, an antibody pair also from Affinity Biologicals was used as described in Haurigot et al. (*Mol Ther* 18:1318 (2010)).

Statistical Analysis:

Statistical analysis was performed with unpaired, two tailed t test. p values <0.05 were considered statistically significant.

AAV Antibody Measurements:

An in vitro neutralization assay described in Manno et al., (*Nat Med* 12:342 (2006)) and Mingozzi et al. (*Nat Med* 13:419 (2007)) was used for antibody measurement. In brief, two AAV vector constructs were used in the assay, a single-stranded vector expressing β-galactosidase under the control of the CMV promoter (ssAAV-LacZ), or a self-complementary vector expressing the Renilla reporter gene, AAV-Rh74-CBA-Renilla, under the control of the chicken β-actin promoter (CBA). To increase the efficiency of transduction of AAV vectors in vitro, 2V6.11 cells (ATCC) were used, which expressed the adenoviral gene E4 under the control of an inducible promoter. Cells were seeded in a 96-well plate at a density of $1.25 \times 10^4$ cells/well and a 1:1000 dilution of ponasterone A (Invitrogen) was added to the medium to induce E4 expression. At the day of assay, serial half-log dilutions of heat-inactivated test serum were mixed with medium containing virus. For the ssAAV-LacZ vector, virus concentration used in the assay was $\sim 1 \times 10^{10}$ vg/ml for AAV2 and $\sim 5.5 \times 10^{10}$ vg/ml for AAV5, 6, or 8. For the scAAV-Luc vector, virus concentration in the assay was between ~50 and 150-fold lower. Residual activity of the reporter transgene was measured using either a colorimetric assay (ssAAV-LacZ) or a luminometer (scAAV-Luc).

Anti-AAV capsid total IgG or Ig subclasses were measured with a capture assay; ELISA plates were coated with $5 \times 10^{10}$ capsid particles/ml of AAV empty capsids. Plates were blocked with 2% BSA, 0.05% Tween 20 in PBS for 2 hours at room temperature and serial dilutions of samples were loaded onto the wells and incubated overnight at 4° C. Biotin-conjugated anti-human IgG1, IgG2, IgG3, IgG4, or IgM antibody (Sigma) were used as detecting antibodies; streptavidin-HRP was the added for substrate detection. Ig concentration was determined against standard curves made with serial dilution of human purified IgG1, IgG2, IgG3, IgG4, or IgM (Sigma).

AAV Production:

The process for vector production is described in detail in Ayuso et al. (*Gene Ther* 17:503 (2010)).

Example 2

This example includes a description of human FIX gene transfer animal (Mice) studies and FIX expression after gene transfer.

C57BL/6 mice (n=5 per group) were injected via the tail vein with AAV vectors bearing the Factor IX (FIX) gene ($2.5^{10}$ vector genomes per mouse) under the control of a liver-specific promoter. Human FIX transgene product (protein) plasma levels in the mice were determined by ELISA at week 1, 2, and 4 post gene transfer, and are illustrated in FIG. 1. AAV-Rh74 showed the highest level of transgene expression in the animals.

Example 3

This example includes a description of animal studies and data demonstrating effective AAV-Rh74 mediated delivery of FIX at therapeutic levels in hemophilia dogs.

Figure 2:
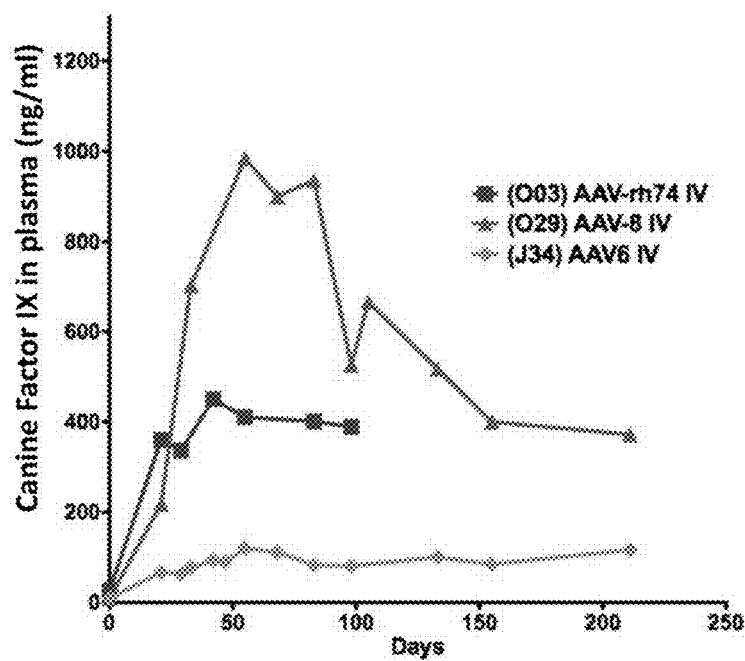
FIG. 2 shows canine FIX plasma levels in hemophilia B dogs after the delivery of $3^{12}$ vector genomes per kilogram (kg) of weight. AAV vectors were infused intravenously (IV) though the saphenous vein and FIX levels were monitored by ELISA. Expression of the therapeutic FIX transgene was driven by a liver specific promoter. AAV8 and AAV-Rh74 vectors performed roughly equally in hemophilia B dogs and were both superior to AAV6.

In brief, hemophilia B dogs were infused intravenously (IV) though the saphenous vein with $3 \times 10^{12}$ vector genomes per kg of weight. Expression of the therapeutic FIX transgene was driven by a liver specific promoter. Vectors and FIX levels were monitored by ELISA. Canine FIX plasma levels are shown in FIG. 2. AAV-Rh74 and AAV8 performed roughly equally in hemophilia B dogs, and both were superior to AAV6.

Example 4

This example includes a description of studies showing the presence of anti-AAV neutralizing antibodies (NAb) in humans.

The data in FIG. 7 show anti-AAV neutralizing antibodies (NAb) measured in humans with an in vitro assay. Subjects with a NAb titer of less than or equal to 1:1 are defined as naïve or low-titer for anti-AAV antibodies, and are eligible for gene transfer for that AAV serotype (highlighted in grey). Patients with titers between 1:1 and 1:3 are considered AAV-permissive as long as empty capsids are used as decoys. Samples with titers higher than 1:3 are considered non-permissive to AAV transduction after systemic injection and are filled in light pink. AAV-Rh74 exhibited the lowest prevalence of anti-AAV Nab compared to AAV-2 and AAV-8.

Example 5

This example includes a description of data showing production amounts of different AAV serotypes including AAV-Rh74.

The data in Table 2 show production yield of different AAV serotypes. Reported are the virus batch size in roller bottles, the total vector yield, and the yield per bottle. All serotypes were packaged with the same expression cassette. AAV-Rh74 has a yield comparable to or greater than the other serotypes evaluated, namely AAV-8, AAV-dj, and AAV-2.

TABLE 2

| Serotype | Batch size (number of roller bottles) | Total vector yield (vector genomes) | Yield per roller bottle (vector genomes) |
|---|---|---|---|
| AAV-Rh74 | 80 | 1.21E+15 | 1.51E+13 |
| AAV-Rh74 | 10 | 1.23E+14 | 1.23E+13 |
| AAV-8 | 30 | 2.54E+14 | 8.47E+12 |
| AAV-dj | 20 | 1.79E+14 | 8.95E+12 |
| AAV-2 | 30 | 1.38E+14 | 4.60E+12 |

Example 6

This example includes a description of data showing that AAVrh74 vector expressing human Factor IX (FIX) under the control of a liver-specific promoter administered to rhesus macaques led to production amounts of FIX in animals, and at higher levels than AAV8 vector administered at the same amount.

In brief, animals were administered either AAV8 or AAVrh74 at a dose of $2 \times 10^{12}$ vector genomes (vg)/kg of weight. Vectors were either formulated in saline or in a mixture of vector and empty AAV capsid (denoted EC).

Figure 4:
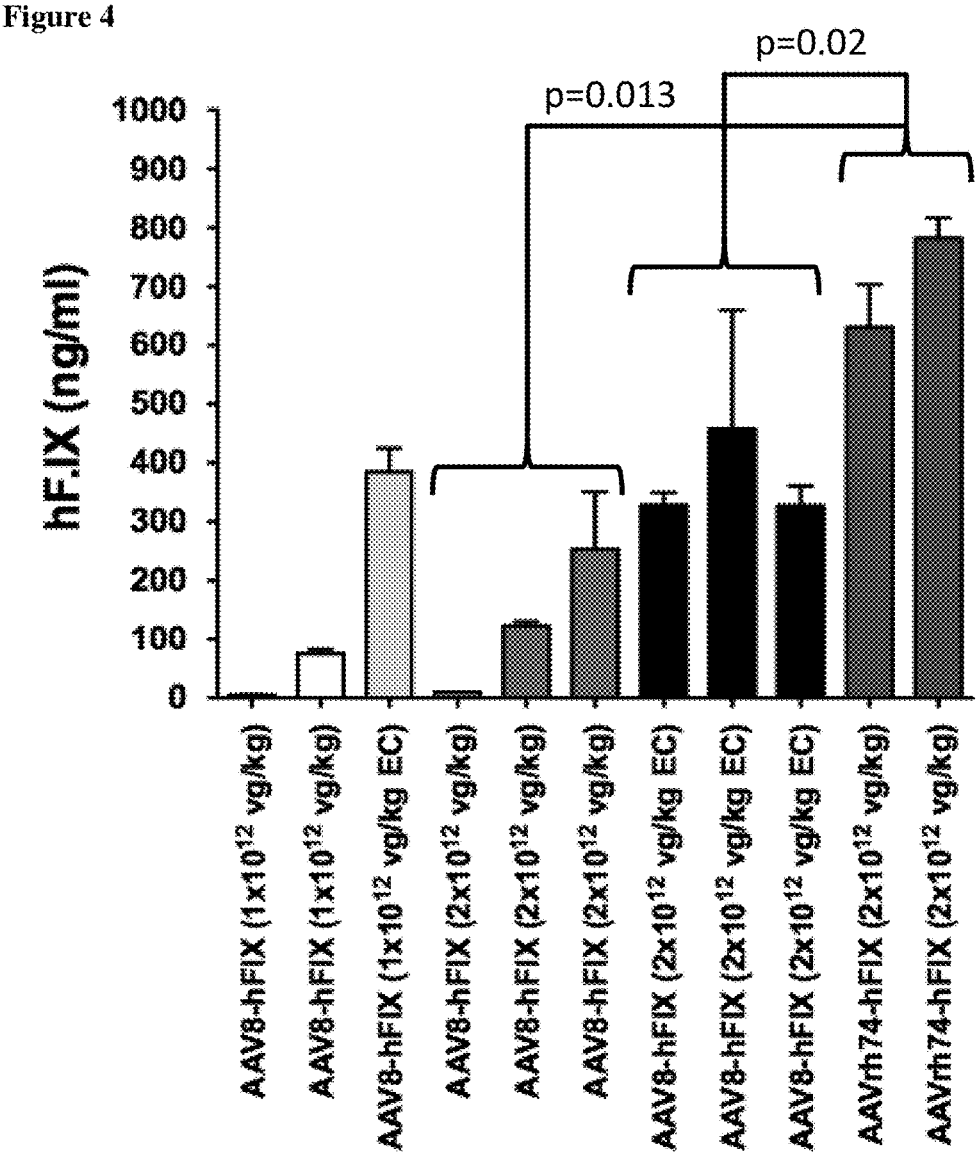
FIG. 4 shows administration of AAV8 and AAVrh74 vector expressing human Factor IX (FIX) (under the control of a liver-specific promoter) to rhesus macaques, a non-human primate, and expression of FIX in the animals. Animals receiving the AAVrh74-FIX vectors (last two bars towards the right margin) expressed the FIX transgene at higher levels compared to the other groups of animals injected at the same dose.

FIG. 4 is a histogram plot of the average (weeks 2 to 8) and standard error or the mean of human FIX measured by an ELISA that detects specifically human FIX in rhesus macaque plasma. Animals receiving the AAVrh74-FIX vector are shown in the last two bars towards the right margin. The data shows that animals receiving the AAVrh74 vectors (last two bars towards right margin) expressed the FIX transgene at higher levels compared to the other groups of animals injected at the same dose (black and grey bars). Average levels were compared using unpaired, two-tailed student t test.

One of the animals receiving AAV-RHM4-1-FIX developed an inhibitor against the human factor IX transgene product, which is a well-documented phenomenon that occurs in approximately 20% of macaques treated with a human FIX vector. The second RHM4-1-treated animal expressed FIX levels around 2-fold higher compared to the AAV8-treated macaques.

Example 7

This example includes a description of several Rh74 capsid variants.

In brief, various substitutions were introduced into Rh74 capsid sequence to produce Rh74 capsid variants. The different Rh74 capsid variants, and substituted amino acids at each position, were as follows:

TABLE 3

| Variants | Amino Acid Substitutions and Indicated Positions in VP1 Capsid |
| --- | --- |
| RHM4_1 | G195A-L199V-S201P-G202N |
| RHM15_1 | G195A-L199V-S201P-G202N K(137/259/333/530/552/569/38/51/77/169/547)R |
| RHM15_2 | G195A-L199V-S201P-G202N K(137/259/333/530/552/569/38/51/77/163/169)R |
| RHM15_3 | G195A-L199V-S201P-G202N K(137/259/333/530/552/569/38/51/77/163/547)R |
| RHM15_4 | G195A-L199V-S201P-G202N K(137/259/333/530/552/569/38/51/77/163/668)R |
| RHM15_5 | G195A-L199V-S201P-G202N K(137/259/333/530/552/569/38/51/77/547/163)R |
| RHM15_6 | G195A-L199V-S201P-G202N K(137/259/333/530/552/569/38/51/77/547/688)R |

RHM4-1 variant had an alanine, a leucine, a proline, and an asparagine substitution at amino acid positions 195, 199, 201 and 202, respectively, of Rh74 VP1 capsid. The RHM4-1 variant VP1 capsid amino acid sequence, with substituted residues a, v, p and n, underlined and in bold, is as follows (SEQ ID NO:5):

```
  1 maadgylpdwlednlsegirewwdlkpgapkpkanqqkqdngrgl
    vlpgykylgpfngld
 61 kgepvnaadaaalehdkaydqqlqagdnpylrynhadaefqerlq
    edtsfggnlgravfq
121 akkrvleplglvespvktapgkkrpvepspqrspdsstgigkkgq
    qpakkrlnfgqtgds
181 esvpdpqpigeppaapsgvgpntmaagggapmadnnegadgvgss
    sgnwhcdstwlgdrv
241 ittstrtwalptynnhlykqisngtsggstndntyfgystpwgyf
    dfnrfhchfsprdwq
301 rlinnnwgfrpkrlnfklfniqvkevtqnegtktiannltstiqv
    ftdseyqlpyvlgsa
361 hqgclppfpadvfmipqygyltlnngsgav grssfycleyfpsq
    mlrtgnnfefsynfed
421 vpfhssyahsqsldrlmnplidqylyylsrtqstggtagtqqllf
    sqagpnnmsaqaknw
481 lpgpcyrqqrvsttlsqnnnsnfawtgatkyhlngrdslvnpgva
    mathkddeerffpss
541 gvlmfgkqgagkdnvdyssvmltseeeikttnpvateqygvvadn
    lqqqnaapivgavns
601 qgalpgmvwqnrdvylqgpiwakiphtdgnfhpsplmggfglkhp
    ppqiliknkntpvpadp
661 pttfnqaklasfitqystgqvsveiewelqkenskrwnpeiqyts
    nyykstnvdfavnte
721 gtyseprpigtryltrnl
```

The RHM4-1 variant VP1 capsid nucleic acid sequence, with codons encoding a, v, p and n, underlined and in bold, is as follows (SEQ ID NO:11):

```
   1 atggctgccgatggttatcttccagattggctcgaggacaacc
     tctctgagggcattcgc
  61 gagtggtgggacctgaaacctggagccccgaaacccaaagcca
     accagcaaaagcaggac
 121 aacggccgggtctggtgcttcctggctacaagtacctcggac
     ccttcaacggactcgac
 181 aaggggagcccgtcaacgcggcgacgcagcggccctcgagc
     acgacaaggcctacgac
 241 cagcagctccaagcgggtgacaatccgtacctgcggtataatc
     acgccgacgccgagttt
 301 caggagcgtctgcaagaagatacgtcttttgggggcaacctcg
     ggcgcgcagtcttccag
 361 gccaaaaagcgggttctcgaacctctgggcctggttgaatcgc
     cggttaagacggctcct
 421 ggaaagaagagaccggtagagccatcaccccagcgctctccag
     actcctctacgggcatc
 481 ggcaagaaaggccagcagcccgcaaaaaagagactcaattttg
     ggcagactggcgactca
 541 gagtcagtccccgaccctcaaccaatcggagaaccaccagcag
     cccctctggtgtggga
 601 cctaatacaatggctgcaggcggtggcgctccaatggcagaca
     ataacgaaggcgccgac
 661 ggagtgggtagttcctcaggaaattggcattgcgattccacat
     ggctgggcgacagagtc
 721 atcaccaccagcacccgcacctgggccctgcccacctacaaca
     accacctctacaagcaa
 781 atctccaacgggacctcggggaggaagcaccaacgacaacacct
     acttcggctacagcacc
 841 ccctgggggtattttgacttcaacagattccactgccacttttt
     caccacgtgactggcag
 901 cgactcatcaacaacaactggggattccggcccaagaggctca
     acttcaagctcttcaac
 961 atccaagtcaaggaggtcacgcagaatgaaggcaccaagacca
     tcgccaataaccttacc
1021 agcacgattcaggtctttacggactcggaataccagctcccgt
     acgtgctcggctcggcg
1081 caccagggctgcctgcctccgttcccggcggacgtcttcatga
     ttcctcagtacgggtac
1141 ctgactctgaacaatggcagtcaggctgtgggccggtcgtcct
     tctactgcctggagtac
1201 tttccttctcaaatgctgagaacgggcaacaactttgaattca
     gctacaacttcgaggac
1261 gtgccttccacagcagctacgcgcacagccagagcctggacc
     ggctgatgaaccctctc
1321 atcgaccagtacttgtactacctgtcccggactcaaagcacgg
     gcggtactgcaggaact
1381 cagcagttgctattttctcaggccgggcctaacaacatgtcgg
     ctcaggccaagaactgg
1441 ctacccggtccctgctaccggcagcaacgcgtctccacgacac
     tgtcgcagaacaacaac
1501 agcaactttgcctggacggtgccaccaagtatcatctgaatg
     gcagagactctctggtg
1561 aatcctggcgttgccatggctacccacaaggacgacgaagagc
     gattttttccatccagc
```

-continued

```
1621  ggagtcttaatgtttgggaaacagggagctggaaaagacaacg
      tggactatagcagcgtg
1681  atgctaaccagcgaggaagaaataaagaccaccaacccagtgg
      ccacagaacagtacggc
1741  gtggtggccgataacctgcaacagcaaaacgccgctcctattg
      taggggccgtcaatagt
1801  caaggagccttacctggcatggtgtggcagaaccgggacgtgt
      acctgcagggtcccatc
1861  tgggccaagattcctcatacggacggcaactttcatccctcgc
      cgctgatgggaggcttt
1921  ggactgaagcatccgcctcctcagatcctgattaaaaacacac
      ctgttcccgcggatcct
1981  ccgaccaccttcaatcaggccaagctggcttctttcatcacgc
      agtacagtaccgccag
2041  gtcagcgtggagatcgagtgggagctgcagaaggagaacagca
      aacgctggaacccagag
2101  attcagtacacttccaactactacaaatctacaaatgtggact
      tgctgtcaatactgag
2161  ggtacttattccgagcctcgccccattggcacccgttacctca
      cccgtaatctg
```

RHM15-1, 15-2, 15-3, 15-4, 1-5 and 15-6 variants also had an alanine, a leucine, a proline, and an asparagine substitution at amino acid positions 195, 199, 201 and 202, respectively, of Rh74 VP1 capsid. In addition, these variants had multiple arginine substitutions of lysine at various positions.

The RHM15-1 variant VP1 capsid amino acid sequence is as follows (SEQ ID NO:6):

```
  1  maadgylpdwlednlsegirewwdlkpgapkpkanqqrqdngrglv
     lpgyrylgpfngld
 61  kgepvnaadaaalehdraydqqlqagdnpylrynhadaefqerlqe
     dtsfggnlgravfq
121  akkrvleplglvespvrtapgkkrpvepspqrspdsstgigkkgqq
     parkrlnfggtgds
181  esvpdpqpigeppaapsgvgpntmaagggapmadnnegadgvgsss
     gnwhcdstwlgdry
241  ittstrtwalptynnhlyrqisngtsggstndntyfgystpwgyfd
     fnrfhchfsprdwg
301  rlinnnwgfrpkrlnfklfniqvkevtqnegtrtiannltstiqvf
     tdseyqlpyvlgsa
361  hqgclppfpadvfmipqygyltlnngsqavgrssfycleyfpsqml
     rtgnnfefsynfed
421  vpfhssyahsqsldrlmnplidqylyylsrtqstggtagtqqllfs
     qagpnnmsaqaknw
481  lpgpcyrqqrvsttlsqnnnsnfawtgatkyhlngrdslvnpgvam
     athrddeerffpss
541  gvlmfgrqgagrdnvdyssvmltseeeirttnpvateqygvvadnl
     qqqn aapivgavns
601  qgalpgmvwqnrdvylqgpiwakiphtdgnfhpsplmggfglkhpp
     pqiliknptpvpadp
661  pttfngaklasfitqystgqvsveiewelqkenskrwnpeiqytsn
     yyksntnvdfavnte
721  gtyseprpigtryltrnl
```

The RHM15-1 variant VP1 capsid nucleic acid sequence is as follows (SEQ ID NO:12):

```
   1  atggctgccgatggttatcttccagattggctcgaggaca
      acctctctgagggcattcgc
  61  gagtggtgggacctgaaacctggagccccgaaacccaaag
      ccaaccagcaaaggcaggac
 121  aacggccgggtctggtgcttcctggctacaggtacctcg
      gacccttcaacggactcgac
 181  aaggggggagcccgtcaacgcggcggacgcagcggccctcg
      agcacgacagggcctacgac
 241  cagcagctccaagcgggtgacaatccgtacctgcggtata
      atcacgccgacgccgagttt
 301  caggagcgtctgcaagaagatacgtcttttgggggcaacc
      tcgggcgcgcagtcttccag
 361  gccaaaaagcgggttctcgaacctctgggcctggttgaat
      cgccggttaggacggctcct
 421  ggaaagaagagaccggtagagccatcaccccagcgctctc
      cagactcctctacgggcatc
 481  ggcaagaaaggccagcagcccgcaagaaagagactcaatt
      ttgggcagactggcgactca
 541  gagtcagtccccgaccctcaaccaatcggagaaccaccag
      cagcccctctggtgtggga
 601  cctaatacaatggctgcaggcggtggcgctccaatggcag
      acaataacgaaggcgccgac
 661  ggagtgggtagttcctcaggaaattggcattgcgattcca
      catggctgggcgacagagtc
 721  atcaccaccagcacccgcacctgggccctgcccacctaca
      acaaccacctctacaggcaa
 781  atctccaacgggacctcgggaggaagcaccaacgacaaca
      cctacttcggctacagcacc
 841  ccctgggggtattttgacttcaacagattccactgccac
      tttcaccacgtgactggcag
 901  cgactcatcaacaacaactgggggattccggcccaagagg
      tcaacttcaagctcttcaac
 961  atccaagtcaaggaggtcacgcagaatgaaggcaccagga
      ccatcgccaa taaccttacc
1021  agcacgattcaggtctttacggactcggaataccagctcc
      cgtacgtgct cggctcggcg
1081  caccagggctgcctgcctccgttcccggcggacgtcttca
      tgattcctca gtacgggtac
1141  ctgactctgaacaatggcagtcaggctgtgggccggtcgt
      ccttctactg cctggagtac
1201  tttccttctcaaatgctgagaacgggcaacaactttgaat
      tcagctacaa cttcgaggac
1261  gtgcccttccacagcagctacgcgcacagccagagcctgg
      accggctgat gaaccctctc
1321  atcgaccagtacttgtactacctgtcccggactcaaagca
      cgggcggtac tgcaggaact
1381  cagcagttgctattttctcaggccgggcctaacaacatgt
      cggctcaggc caagaactgg
1441  ctaccgcgtccctgctaccggcagcaacgcgtctccacga
      cactgtcgca gaacaacaac
1501  agcaactttgcctggacgggtgccaccaagtatcatctga
      atggcagaga ctctctggtg
```

-continued

```
1561  aatcctggcgttgccatggctacccacagggacgacgaag
      agcgattttt tccatccagc 1621  ggagtcttaatgtttgggagacagggagctggaagagaca
      acgtggacta tagcagcgtg 1681  atgctaaccagcgaggaagaaataaggaccaccaacccag
      tggccacaga acagtacggc 1741  gtggtggccgataacctgcaacagcaaaacgccgctccta
      ttgtagggc cgtcaatagt 1801  caaggagccttacctggcatggtgtggcagaaccgggacg
      tgtacctgca gggtcccatc 1861  tgggccaagattcctcatacggacggcaactttcatccct
      cgccgctgat gggaggcttt 1921  ggactgaagcatccgcctcctcagatcctgattaaaaaca
      cacctgttcc cgcggatcct 1981  ccgaccaccttcaatcaggccaagctggcttctttcatca
      cgcagtacag taccggccag 2041  gtcagcgtggagatcgagtgggagctgcagaaggagaaca
      gcaaacgctg gaacccagag 2101  attcagtacacttccaactactacaaatctacaaatgtgg
      actttgctgt caatactgag 2161  ggtacttattccgagcctcgccccattggcacccgttacc
      tcacccgtaa tctgtaa
```

The RHM15-2 variant VP1 capsid amino acid sequence is as follows (SEQ ID NO:7):

```
  1  maadgylpdwlednlsegirewwdlkpgapkpkanqqrqd
     ngrglvlpgy rylgpfngld 61  kgepvnaadaaalehdraydqqlqagdnpylrynhadaef
     qerlqedtsf ggnlgravfq 121  akkrvleplglvespvrtapgkkrpvepspqrspdsstgi
     gkrgqpark rlnfgqtgds 181  esvpdpqpigeppaapsgvgpntmaagggapmadnnegad
     gvgsssgnwh cdstwlgdrv 241  ittstrtwalptynnhlyrqisngtsggstndntyfgyst
     pwgyfdfnrf hchfsprdwq 301  rlinnnwgfrpkrlnfklfniqvkevtqnegtrtiannit
     stiqvftdse yqlpyvlgsa 361  hqgclppfpadvfmipqygyltlnngsqavgrssfycley
     fpsqmlrtgn nfefsynfed 421  vpfhssyahsqsldrlmnplidqylyylsrtqstggtagt
     qqllfsqagp nnmsaqaknw 481  lpgpcyrqqrvsttlsqnnnsnfawtgatkyhlngrdslv
     npgvamathr ddeerffpss 541  gvlmfgkqgagrdnvdyssvmltseeeirttnpvateqyg
     vvadnlqqqn aapivgavns 601  qgalpgmvwqnrdvylqgpiwakiphtdgnfhpsplmggf
     glkhpppqil ikntpvpadp 661  pttfnqaklasfitqystgqvsveiewelqkenskrwnpe
     iqytsnyyks tnvdfavnte 721  gtyseprpigtryltrnl
```

The RHM15-2 variant VP1 capsid nucleic acid sequence is as follows (SEQ ID NO:13):

```
   1  atggctgccgatggttatcttccagattggctcgaggaca
      acctctctga gggcattcgc 61  gagtggtgggacctgaaacctggagccccgaaacccaaag
      ccaaccagca aaggcaggac 121  aacggccgggtctggtgcttcctggctacaggtacctcg
      gacccttcaa cggactcgac 181  aaggggagcccgtcaacgcggcggacgcagcggccctcg
      agcacgacag ggcctacgac 241  cagcagctccaagcgggtgacaatccgtacctgcggtata
      atcacgccga cgccgagttt 301  caggagcgtctgcaagaagatacgtcttttgggggcaacc
      tcgggcgcgc agtcttccag 361  gccaaaaagcgggttctcgaacctctgggcctggttgaat
      cgccggttag gacggctcct 421  ggaaagaagagaccggtagagccatcaccccagcgctctc
      cagactcctc tacgggcatc 481  ggcaagagaggccagcagcccgcaagaaagagactcaatt
      ttgggcagac tggcgactca 541  gagtcagtccccgaccctcaaccaatcggagaaccaccag
      cagcccccct ctggtgtggga 601  cctaatacaatggctgcaggcggtggcgctccaatggcag
      acaataacga aggcgccgac 661  ggagtgggtagttcctcaggaaattggcattgcgattcca
      catggctggg cgacagagtc 721  atcaccaccagcacccgcacctgggccctgcccacctaca
      acaaccacct ctacaggcaa 781  atctccaacgggacctcggggaggaagcaccaacgacaaca
      cctacttcgg ctacagcacc 841  ccctgggggtattttgacttcaacagattccactgccact
      tttcaccacg tgactggcag 901  cgactcatcaacaacaactgggattccggcccaagaggc
      tcaacttcaa gctcttcaac 961  atccaagtcaaggaggtcacgcagaatgaaggcaccagga
      ccatcgccaa taaccttacc 1021  agcacgattcaggtctttacggactcggaataccagctcc
      cgtacgtgct cggctcggcg 1081  caccagggctgcctgcctccgttcccggcggacgtcttca
      tgattcctca gtacgggtac 1141  ctgactctgaacaatggcagtcaggctgtgggccggtcgt
      ccttctactg cctggagtac 1201  tttccttctcaaatgctgagaacgggcaacaactttgaat
      tcagctacaa cttcgaggac 1261  gtgccttccacagcagctacgcgcacagccagagcctgg
      accggctgat gaaccctctc 1321  atcgaccagtacttgtactacctgtcccggactcaaagca
      cgggcggtac tgcaggaact 1381  cagcagttgctatttttctcaggccgggcctaacaacatgt
      cggctcaggc caagaactgg 1441  ctaccggtccctgctaccggcagcaacgcgtctccacga
      cactgtcgca gaacaacaac 1501  agcaactttgcctggacgggtgccaccaagtatcatctga
      atggcagaga ctctctggtg 1561  aatcctggcgttgccatggctacccacagggacgacgaag
      agcgattttt tccatccagc
```

```
1621  ggagtcttaatgtttgggaaacagggagctggaagagaca
      acgtggacta tagcagcgtg
1681  atgctaaccagcgaggaagaaataaggaccaccaacccag
      tggccacaga acagtacggc
1741  gtggtggccgataacctgcaacagcaaaacgccgctccta
      ttgtagggc cgtcaatagt
1801  caaggagccttacctggcatggtgtggcagaaccgggacg
      tgtacctgca gggtcccatc
1861  tgggccaagattcctcatacggacggcaactttcatccct
      cgccgctgat gggaggcttt
1921  ggactgaagcatccgcctcctcagatcctgattaaaaaca
      cacctgttcc cgcggatcct
1981  ccgaccaccttcaatcaggccaagctggcttctttcatca
      cgcagtacag taccggccag
2041  gtcagcgtggagatcgagtgggagctgcagaaggagaaca
      gcaaacgctg gaacccagag
2101  attcagtacacttccaactactacaaatctacaaatgtgg
      actttgctgt caatactgag
2161  ggtacttattccgagcctcgccccattggcacccgttacc
      tcacccgtaa tctgtaa
```

The RHM15-3/RHM15-5 variant VP1 capsid amino acid sequence is as follows (SEQ ID NO:8):

```
  1  maadgylpdwlednlsegir ewwdlkpgapkpkanqqrqd
     ngrglvlpgy rylgpfngld
 61  kgepvnaadaaalehdraydqqlqagdnpylrynhadaef
     qerlqedtsf ggnlgravfq
121  akkrvleplglvespvrtapgkkrpvepspqrspdsstgi
     gkrgqqpakk rlnfgqtgds
181  esvpdpqpigeppaapsgvgpntmaagggapmadnnegad
     gvgsssgnwh cdstwlgdrv
241  ittstrtwalptynnhlyrqisngtsggstndntyfgyst
     pwgyfdfnrf hchfsprdwq
301  rlinnnwgfrpkrlnfklfniqvkevtqnegtrtiannlt
     stiqvftdse yqlpyvlgsa
361  hqgclppfpadvfmipqygyltlnngsqavgrssfycley
     fpsqmlrtgn nfefsynfed
421  vpfhssyahsqsldrlmnplidqylyylsrtqstggtagt
     qqllfsqagp nnmsaqaknw
481  lpgpcyrqqrvsttlsqnnnsnfawtgatkyhlngrdslv
     npgvamathr ddeerffpss
541  gvlmfgrqgagrdnvdyssvmltseeeirttnpvateqyg
     vvadnlqqqn aapivgavns
601  qgalpgmvwqnrdvylqgpiwakiphtdgnfhpsplmggf
     glkhpppqil ikntpvpadp
661  pttfnqaklasfitqystgqvsveiewelqkenskrwnpe
     iqytsnyyks tnvdfavnte
721  gtyseprpigtryltrnl
```

The RHM15-3/RHM15-5 variant VP1 capsid nucleic acid sequence is as follows (SEQ ID NO:14):

```
   1  atggctgccgatggttatcttccagattggctcgaggaca
      acctctctga gggcattcgc
  61  gagtggtgggacctgaaacctggagccccgaaacccaaag
      ccaaccagca aaggcaggac
 121  aacggccgggtctggtgcttcctggctacaggtacctcg
      gacccttcaa cggactcgac
 181  aaggggagcccgtcaacgcggcggacgcagcggccctcg
      agcacgacag ggcctacgac
 241  cagcagctccaagcgggtgacaatccgtacctgcggtata
      atcacgccga cgccgagttt
 301  caggagcgtctgcaagaagatacgtcttttgggggcaacc
      tcgggcgcgc agtcttccag
 361  gccaaaaagcgggttctcgaacctctgggcctggttgaat
      cgccggttag gacggctcct
 421  ggaaagaagagaccggtagagccatcaccccagcgctctc
      cagactcctc tacgggcatc
 481  ggcaagagaggccagcagcccgcaaaaaagagactcaatt
      ttgggcagac tggcgactca
 541  gagtcagtccccgaccctcaaccaatcggagaaccaccag
      cagccccctc tggtgtggga
 601  cctaatacaatggctgcaggcggtggcgctccaatggcag
      acaataacga aggcgccgac
 661  ggagtgggtagttcctcaggaaattggcattgcgattcca
      catggctggg cgacagagtc
 721  atcaccaccagcacccgcacctgggccctgcccacctaca
      acaaccacct ctacaggcaa
 781  atctccaacgggacctcgggaggaagcaccaacgacaaca
      cctacttcgg ctacagcacc
 841  ccctgggggtattttgacttcaacagattccactgccact
      tttcaccacg tgactggcag
 901  cgactcatcaacaacaactggggattccggcccaagaggc
      tcaacttcaa gctcttcaac
 961  atccaagtcaaggaggtcacgcagaatgaaggcaccagga
      ccatcgccaa taaccttacc
1021  agcacgattcaggtctttacggactcggaataccagctcc
      cgtacgtgct cggctcggcg
1081  caccaggctgcctgcctccgttcccggcggacgtcttca
      tgattcctca gtacgggtac
1141  ctgactctgaacaatggcagtcaggctgtgggccggtcgt
      ccttctactg cctggagtac
1201  tttccttctcaaatgctgagaacgggcaacaactttgaat
      tcagctacaa cttcgaggac
1261  gtgcccttccacagcagctacgcgcacagccagagcctgg
      accggctgat gaaccctctc
1321  atcgaccagtacttgtactacctgtcccggactcaaagca
      cgggcggtac tgcaggaact
1381  cagcagttgctattttctcaggccgggcctaacaacatgt
      cggctcaggc caagaactgg
1441  ctaccggtccctgctaccggcagcaacgcgtctccacga
      cactgtcgca gaacaacaac
1501  agcaactttgcctggacgggtgccaccaagtatcatctga
      atggcagaga ctctctggtg
1561  aatcctggcgttgccatggctacccacagggacgacgaag
      agcgatttt tccatccagc
1621  ggagtcttaatgtttgggagacaggagctggaagagaca
      acgtggacta tagcagcgtg
```

```
1681  atgctaaccagcgaggaagaaataaggaccaccaacccag
      tggccacaga acagtacggc 1741  gtggtggccgataacctgcaacagcaaaacgccgctccta
      ttgtagggc cgtcaatagt 1801  caaggagccttacctggcatggtgtggcagaaccgggacg
      tgtacctgca gggtcccatc 1861  tgggccaagattcctcatacggacggcaactttcatccct
      cgccgctgat gggaggcttt 1921  ggactgaagcatccgcctcctcagatcctgattaaaaaca
      cacctgttcc gcggatcct 1981  ccgaccaccttcaatcaggccaagctggcttctttcatca
      cgcagtacag taccggccag 2041  gtcagcgtggagatcgagtgggagctgcagaaggagaaca
      gcaaacgctg gaacccagag 2101  attcagtacacttccaactactacaaatctacaaatgtgg
      actttgctgt caatactgag 2161  ggtacttattccgagcctcgccccattggcacccgttacc
      tcacccgtaa tctgtaa
```

The RHM15-4 variant VP1 capsid amino acid sequence is as follows (SEQ ID NO:9):

```
  1  maadgylpdwlednlsegirewwdlkpgap kpkanqqrqd
     ngrglvlpgy rylgpfngld
 61  kgepvnaadaaalehdraydqqlqagdnpy lrynhadaef
     qerlqedtsf ggnlgravfq
121  akkrvleplglvespvrtapgkkrpvepsp qrspdsstgi
     gkrgqqpakk rlnfgqtgds
181  esvpdpqpigeppaapsgvgpntmaaggga pmadnnegad
     gvgsssgnwh cdstwlgdrv
241  ittstrtwalptynnhlyrqisngtsggst ndntyfgyst
     pwgyfdfnrf hchfsprdwq
301  rlinnnwgfrpkrlnfklfniqvkevtqne gtrtiannlt
     stiqvftdse yqlpyvlgsa
361  hqgclppfpadvfmipqygyltlnngsqav grssfycley
     fpsqmlrtgn nfefsynfed
421  vpfhssyahsqsldrlmnplidqylyylsr tqstggtagt
     qqllfsqagp nnmsaqaknw
481  lpgpcyrqqrvsttlsqnnnsnfawtgatk yhlngrdslv
     npgvamathr ddeerffpss
541  gvlmfgkqgagrdnvdyssvmltseeeirt tnpvateqyg
     vvadnlqqqn aapivgavns
601  qgalpgmvwqnrdvylqgpiwakiphtdgn fhpsplmggf
     glkhpppqil ikntpvpadp
661  pttfnqarlasfitqystgqvsveiewelq kenskrwnpe
     iqytsnyyks tnvdfavnte
721  gtyseprpigtryltrnl
```

The RHM15-4 variant VP1 capsid nucleic acid sequence is as follows (SEQ ID NO:15):

```
   1  atggctgccgatggttatcttccagattggctcgaggaca
      acctctctga gggcattcgc
  61  gagtggtgggacctgaaacctggagccccgaaacccaaag
      ccaaccagca aaggcaggac
 121  aacggccgggtctggtgcttcctggctacaggtacctcg
      gacccttcaa cggactcgac
 181  aagggggagcccgtcaacgcggcggacgcagcggccctcg
      agcacgacag ggcctacgac
 241  cagcagctccaagcgggtgacaatccgtacctgcggtata
      atcacgccga cgccgagttt
 301  caggagcgtctgcaagaagatacgtcttttgggggcaacc
      tcgggcgcgc agtcttccag
 361  gccaaaaagcgggttctcgaacctctgggcctggttgaat
      cgccggttag gacggctcct
 421  ggaaagaagagaccggtagagccatcacccccagcgctctc
      cagactcctc tacgggcatc
 481  ggcaagagaggccagcagcccgcaaaaaagagactcaatt
      ttgggcagac tggcgactca
 541  gagtcagtccccgaccctcaaccaatcggagaaccaccag
      cagcccctc tggtgtggga
 601  cctaatcaatggctgcaggcggtggcgctccaatggcag
      acaataacga aggcgccgac
 661  ggagtgggtagttcctcaggaaattggcattgcgattcca
      catggctggg cgacagagtc
 721  atcaccaccagcacccgcacctgggccctgcccacctaca
      acaaccacct ctacaggcaa
 781  atctccaacgggacctcgggaggaagcaccaacgacaaca
      cctacttcgg ctacagcacc
 841  ccctgggggtatttgacttcaacagattccactgccact
      tttcaccacg tgactggcag
 901  cgactcatcaacaacaactggggattccggcccaagaggc
      tcaacttcaa gctcttcaac
 961  atccaagtcaaggaggtcacgcagaatgaaggcaccagga
      ccatcgccaa taaccttacc
1021  agcacgattcaggtctttacggactcggaataccagctcc
      cgtacgtgct cggctcggcg
1081  caccagggctgcctgcctccgttcccggcggacgtcttca
      tgattcctca gtacgggtac
1141  ctgactctgaacaatggcagtcaggctgtgggccggtcgt
      ccttctactg cctggagtac
1201  tttccttctcaaatgctgagaacgggcaacaactttgaat
      tcagctacaa cttcgaggac
1261  gtgcccttccacagcagctacgcgcacagccagagcctgg
      accggctgat gaaccctctc
1321  atcgaccagtacttgtactacctgtcccggactcaaagca
      cgggcggtac tgcaggaact
1381  cagcagttgctattttctcaggccgggcctaacaacatgt
      cggctcaggc caagaactgg
1441  ctacccggtccctgctaccggcagcaacgcgtctccacga
      cactgtcgca gaacaacaac
1501  agcaactttgcctggacgggtgccaccaagtatcatctga
      atggcagaga ctctctggtg
1561  aatcctggcgttgccatggctacccacagggacgacgaag
      agcgatttt tccatccagc
1621  ggagtcttaatgtttgggaaacagggagctggaagagaca
      acgtggacta tagcagcgtg
1681  atgctaaccagcgaggaagaaataaggaccaccaacccag
      tggccacaga acagtacggc
```

```
1741  gtggtggccgataacctgcaacagcaaaacgccgctccta
      ttgtaggggc cgtcaatagt
1801  caaggagcct tacctggcat ggtgtggcag aaccgggacg
      tgtacctgca gggtcccatc
1861  tgggccaaga ttcctcatac ggacggcaac tttcatccct
      cgccgctgat gggaggcttt
1921  ggactgaagc atccgcctcc tcagatcctg attaaaaaca
      cacctgttcc cgcggatcct
1981  ccgaccacct tcaatcaggc caggctggct tctttcatca
      cgcagtacag taccggccag
2041  gtcagcgtgg agatcgagtg ggagctgcag aaggagaaca
      gcaaacgctg gaacccagag
2101  attcagtaca cttccaacta ctacaaatct acaaatgtgg
      actttgctgt caatactgag
2161  ggtacttatt ccgagcctcg ccccattggc acccgttacc
      tcacccgtaa tctgtaa
```

The RHM15-6 variant VP1 capsid amino acid sequence is as follows (SEQ ID NO:10):

```
  1  maadgylpdwlednlsegirewwdlkpgapkpkanqqrqdngrg
     lvlpgy rylgpfngld
 61  kgepvnaadaaalehdraydqqlqagdnpylrynhadaefgerl
     qedtsf ggnlgravfq
121  akkrvleplglvespvrtapgkkrpvepspqrspdsstgigkkg
     qqpakk rlnfgqtgds
181  esvpdpqpigeppaapsgvgpntmaagggapmadnnegadgvgs
     ssgnwh cdstwlgdrv
241  ittstrtwalptynnhlyrgisngtsggstndntyfgystpwgy
     fdfnrf hchfsprdwq
301  rlinnnwgfrpkrlnfklfniqvkevtgnegtrtiannltstiq
     vftdse yqlpyvlgsa
361  hqgclppfpadvfmipqygyltlnngsgavgrssfycleyfpsc
     plrtgn nfefsynfed
421  vpfhssyahsqsldrlmnplidqylyylsrtqstggtagtqqll
     fsqagp nnmsaqaknw
481  lpgpcyrqqrvsttlsqnnnsnfawtgatkyhlngrdslvnpgv
     amathr ddeerffpss
541  gvlmfgrqgagrdnvdyssvmltseeeirttnpvategygvvad
     nlqqqn aapivgavns
601  qgalpgmvwqnrdvylqgpiwakiphtdgnfhpsplmggfglkh
     pppgil ikntpvpadp
661  pttfnqarlasfitgystgqvsveiewelqkenskrwnpeigyt
     snyyks tnvdfavnte
721  gtyseprpigtryltrnl
```

The RHM15-6 variant VP1 capsid nucleic acid sequence is as follows (SEQ ID NO:16):

```
   1  atggctgccgatggttatcttccagattggctcgaggaca
      acctctctga gggcattcgc
  61  gagtggtggg acctgaaacc tggagccccg aaacccaaag
      ccaaccagca aaggcaggac
 121  aacggccggg gtctggtgct tcctggctac aggtacctcg
      gacccttcaa cggactcgac
 181  aaggggagcc cgtcaacgcg gcggacgcag cggccctcg
      agcacgacag ggcctacgac
 241  cagcagctcc aagcgggtga caatccgtac ctgcggtata
      atcacgccga cgccgagttt
 301  caggagcgtc tgcaagaaga tacgtctttt gggggcaacc
      tcgggcgcgc agtcttccag
 361  gccaaaaagc gggttctcga acctctgggc ctggttgaat
      cgccggttag gacggctcct
 421  ggaaagaaga gaccggtaga gccatcaccc cagcgctctc
      cagactcctc tacgggcatc
 481  ggcaagaaag gccagcagcc cgcaaaaaag agactcaatt
      ttgggcagac tggcgactca
 541  gagtcagtcc ccgaccctca accaatcgga gaaccaccag
      cagccccctc tggtgtggga
 601  cctaatacaa tggctgcagg cggtggcgct ccaatggcag
      acaataacga aggcgccgac
 661  ggagtgggta gttcctcagg aaattggcat tgcgattcca
      catggctggg cgacagagtc
 721  atcaccacca gcacccgcac ctgggccctg cccacctaca
      acaaccacct ctacaggcaa
 781  atctccaacg ggacctcggg aggaagcacc aacgacaaca
      cctacttcgg ctacagcacc
 841  ccctggggta ttttgacttc aacagattcc actgccact
      tttcaccacg tgactggcag
 901  cgactcatca acaacaactg gggattccgg cccaagaggc
      tcaacttcaa gctcttcaac
 961  atccaagtca aggaggtcac gcagaatgaa ggcaccagga
      ccatcgccaa taaccttacc
1021  agcacgattc aggtcttacg gactcggaat accagctcc
      cgtacgtgct cggctcggcg
1081  caccagggct gcctgcctcc gttcccggcg gacgtcttca
      tgattcctca gtacgggtac
1141  ctgactctga acaatggcag tcaggctgtg ggccggtcgt
      ccttctactg cctggagtac
1201  tttccttctc aaatgctgag aacgggcaac aactttgaat
      tcagctacaa cttcgaggac
1261  gtgcccttcc acagcagcta cgcgcacagc cagagcctgg
      accggctgat gaaccctctc
1321  atcgaccagt acttgtacta cctgtcccgg actcaaagca
      cgggcggtac tgcaggaact
1381  cagcagttgc tattttctc aggccgggcc taacaacatgt
      cggctcaggc caagaactgg
1441  ctacccggtc cctgctaccg gcagcaacgc gtctccacga
      cactgtcgca gaacaacaac
1501  agcaactttg cctggacggg tgccaccaag tatcatctga
      atggcagaga ctctctggtg
1561  aatcctggcg ttgccatggc tacccacagg gacgacgaag
      agcgattttt tccatccagc
1621  ggagtcttaa tgtttgggag acaggagctg gaagagaca
      acgtggacta tagcagcgtg
1681  atgctaacca gcgaggaaga aataaggacc accaacccag
      tggccacaga acagtacggc
1741  gtggtggccg ataacctgca acagcaaaac gccgctccta
      ttgtaggggc cgtcaatagt
```

-continued

```
1801    caaggagccttacctggcatggtgtggcagaaccgggacg
        tgtacctgca gggtcccatc 1861    tgggccaagattcctcatacggacggcaactttcatccct
        cgccgctgat gggaggcttt 1921    ggactgaagcatccgcctcctcagatcctgattaaaaaca
        cacctgttcc cgcggatcct 1981    ccgaccaccttcaatcaggccaggctggcttctttcatca
        cgcagtacag taccggccag 2041    gtcagcgtggagatcgagtgggagctgcagaaggagaaca
        gcaaacgctg gaacccagag 2101    attcagtacacttccaactactacaaatctacaaatgtgg
        actttgctgt caatactgag 2161    ggtacttattccgagcctcgccccattggcacccgttacc
        tcaccgtaa tctgtaa
```

Example 8

This example includes a description of human factor IX expression studies using the Rh74 capsid variants compared to Rh74 and AAV8.

In brief, Rh74 capsid variants were used to package an AAV human factor IX expression vector, the AAV particles used to infect mice, and expression levels of factor IX determined in the animals (plasma). The capsid variants had the following amino acid substitutions at the indicated positions:

TABLE 4

| | |
|---|---|
| RHM4_1 | G195A-L199V-S201P-G202N |
| RHM15_1 | G195A-L199V-S201P-G202N K(137/259/333/530/552/569/38/51/77/169/547)R |
| RHM15_2 | G195A-L199V-S201P-G202N K(137/259/333/530/552/569/38/51/77/163/169)R |
| RHM15_3 | G195A-L199V-S201P-G202N K(137/259/333/530/552/569/38/51/77/163/547)R |
| RHM15_4 | G195A-L199V-S201P-G202N K(137/259/333/530/552/569/38/51/77/163/668)R |

TABLE 4-continued

| | |
|---|---|
| RHM15_5 | G195A-L199V-S201P-G202N K(137/259/333/530/552/569/38/51/77/547/163)R |
| RHM15_6 | G195A-L199V-S201P-G202N K(137/259/333/530/552/569/38/51/77/547/688)R |

Figure 5:
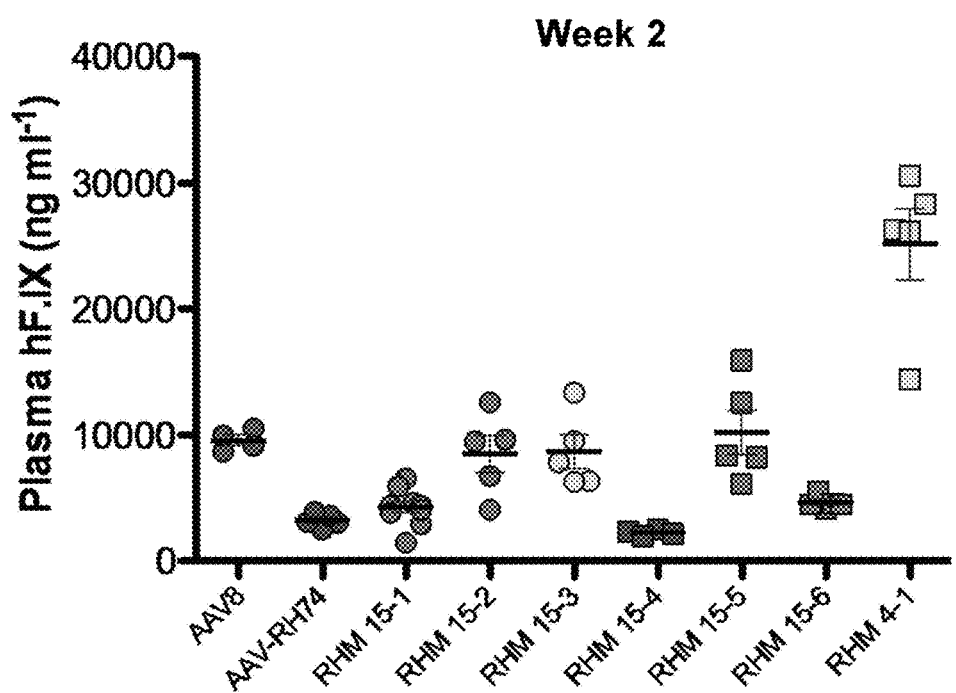
FIG. 5 shows plasma human factor IX expression levels in animals administered AAV human factor IX expression vector encapsidated by the indicated AAV (Rh74 variants, such as RHM4-1 variant), compared to Rh74 and AAV8 encapsidated AAV human factor IX expression vector.

FIG. 5 shows plasma human factor IX expression levels in treated animals after 2 weeks. As illustrated, AAV human factor IX expression vector encapsidated by RHM4-1 variant Capsid provided the highest level of expression, and was substantially greater than expression produced by Rh74 encapsidated AAV human factor IX expression vector, and AAV8 encapsidated AAV human factor IX expression vector.

Example 9

This example includes a description of data showing that AAVrh74 variant RHM4-1 vector expressing human Factor IX (FIX) under the control of a liver-specific promoter administered to cynomolgus macaques led to production amounts of FIX in animals, and at higher levels than AAV8 vector administered at the same amount.

Figure 6:
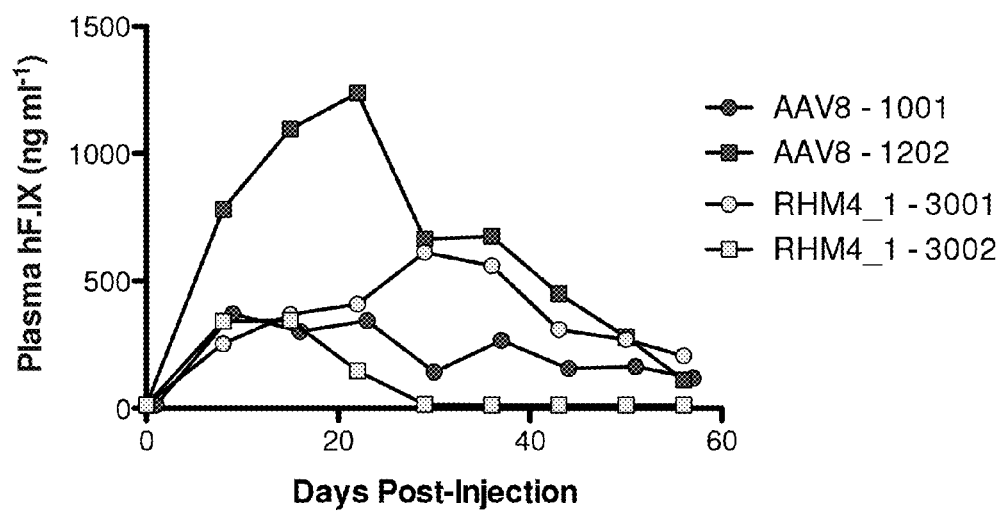
FIG. 6 shows administration of AAV8 and AAV-Rh74 variant RHM4-1 vector expressing human Factor IX (under the control of a liver-specific promoter) to cynomolgus macaques, a non-human primate, and expression of FIX in the animals.

Cynomolgus monkeys were prescreened for neutralizing AAV antibodies, and animals with pre-treatment titers of <1:1 were selected to ensure that transduction was successful. The monkeys were then infused with either AAV8 or AAV-Rh74 variant RHM4-1 vectors expressing a human factor IX transgene at a dose of $3 \times 10^{12}$ vg/kg. Human FIX transgene product (protein) plasma levels in the non-human primates were determined by ELISA weekly throughout the duration of the study and are illustrated in FIG. 6.

One of the animals receiving AAV-RHM4-1-FIX developed an inhibitor against the human factor IX transgene product, which is a well-documented phenomenon that occurs in approximately 20% of macaques treated with a human FIX vector owing to small amino acid differences between the human and macaque proteins. The loss of expression in one animal treated with RHM4-1 was due to the development of an antibody response against the human transgene. The second RHM4-1-treated animal expressed FIX levels around 2-fold higher compared to the AAV8-treated macaques.

What is claimed:

1. A recombinant AAV (rAAV) particle comprising a VP1 capsid protein comprising the amino acid sequence of SEQ ID NO:5, wherein the genome of said rAAV particle comprises an AAV inverted terminal repeat and a heterologous polynucleotide sequence encoding a human Factor IX protein operably linked to an expression control element.

2. The recombinant AAV particle of claim 1, wherein said expression control element comprises a tissue-specific enhancer or promoter.

3. The recombinant AAV particle of claim 2, wherein said tissue-specific enhancer or promoter is specific for liver.

4. The recombinant AAV particle of claim 1, wherein the genome of the recombinant AAV particle further comprises at least a portion of an intron.

5. The recombinant AAV particle of claim 1, wherein the genome of the recombinant AAV particle further comprises a filler or stuffer polynucleotide sequence.

6. A pharmaceutical composition comprising the recombinant AAV particle of claim 1 and a pharmaceutically acceptable carrier.

7. A method for producing the recombinant AAV particle of claim 1, comprising culturing a helper cell comprising a recombinant plasmid comprising the genome of the recombinant AAV particle of claim 1.

8. A method of treating a subject in need of treatment for hemophilia B comprising administering to said subject a therapeutically effective amount of the pharmaceutical composition of claim 6.

9. The method of claim 8, wherein said subject is a human.

10. A recombinant AAV (rAAV) particle comprising a VP1 capsid protein having the amino acid sequence of SEQ ID NO: 5, wherein the genome of said rAAV particle comprises, in 5' to 3' order:
   (a) a first AAV inverted terminal repeat,
   (b) a liver-specific enhancer and promoter,
   (c) a polynucleotide sequence encoding a human Factor IX protein operably linked to the liver-specific enhancer and promoter,
   (d) a poly-A sequence; and
   (e) a second AAV inverted terminal repeat.

11. The recombinant AAV particle of claim 10, wherein said first and second AAV inverted terminal repeats are from AAV2.

12. The recombinant AAV particle of claim 10, wherein said liver-specific enhancer and promoter is an ApoE-hAAT enhancer-promoter.

13. The recombinant AAV particle of claim 10, wherein said polynucleotide sequence encoding the human Factor IX protein further comprises at least a portion of an intron.

14. The recombinant AAV particle of claim 13, wherein said intron is intron I of human Factor IX.

15. The recombinant AAV particle of claim 14, wherein said portion of intron I of human Factor IX has a nucleotide length of 0.1 kb to 1.7 kb.

16. The recombinant AAV particle of claim 10, wherein said polynucleotide sequence is flanked by 5' and 3' untranslated regions.

17. A pharmaceutical composition comprising the recombinant AAV particle of claim 10 and a pharmaceutically acceptable carrier.

18. A method of treating a subject in need of treatment for hemophilia B comprising administering to said subject a therapeutically effective amount of the pharmaceutical composition of claim 17.

19. The recombinant AAV particle of claim 10, wherein the human Factor IX protein is a variant more active than wild type human Factor IX.

20. The recombinant AAV particle of claim 19, wherein the human Factor IX protein variant is naturally occurring.

21. The recombinant AAV particle of claim 10, wherein the human Factor IX protein is a naturally occurring variant that retains activity of human Factor IX.

\* \* \* \* \*

SEQUENCE LISTING

<160> NUMBER OF SEQ ID NOS: 16

<210> SEQ ID NO 1
<211> LENGTH: 738
<212> TYPE: PRT
<213> ORGANISM: Adeno-associated virus

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
```

```
                    85                  90                  95
Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Ser Pro Val Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510
```

```
                                    -continued

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 2
<211> LENGTH: 2217
<212> TYPE: DNA
<213> ORGANISM: Adeno-associated virus

<400> SEQUENCE: 2
atggctgccg atggttatct tccagattgg ctcgaggaca cctctctga gggcattcgc        60 gagtggtggg acctgaaacc tggagccccg aaacccaaag ccaaccagca aaagcaggac      120 aacgccggg gtctggtgct tcctggctac aagtacctcg acccttcaa cggactcgac        180 aagggggagc ccgtcaacgc ggcggacgca gcggccctcg agcacgacaa ggcctacgac      240
cagcagctcc aagcgggtga caatccgtac ctgcggtata tcacgccga cgccgagttt      300 caggagcgtc tgcaagaaga tacgtctttt gggggcaacc tcgggcgcgc agtcttccag      360
gccaaaaagc gggttctcga acctctgggc ctggttgaat cgccggttaa acggctcct      420 ggaaagaaga gaccggtaga gccatcaccc agcgctctc cagactcctc tacgggcatc      480
ggcaagaaag ccagcagcc cgcaaaaaag agactcaatt ttgggcagac tggcgactca      540
gagtcagtcc ccgaccctca accaatcgga gaaccaccag caggcccctc tggtctggga      600
tctggtacaa tggctgcagg cggtggcgct ccaatggcag acaataacga aggcgccgac      660
ggagtgggta gttcctcagg aaattggcat gcgattcca catggctggg cgacagagtc      720
atcaccacca gcacccgcac ctgggcctg cccacctaca caaccacct ctacaagcaa      780
```

```
atctccaacg ggacctcggg aggaagcacc aacgacaaca cctacttcgg ctacagcacc    840
ccctgggggt attttgactt caacagattc cactgccact tttcaccacg tgactggcag    900
cgactcatca acaacaactg gggattccgg cccaagaggc tcaacttcaa gctcttcaac    960
atccaagtca aggaggtcac gcagaatgaa ggcaccaaga ccatcgccaa taaccttacc   1020
agcacgattc aggtctttac ggactcggaa taccagctcc cgtacgtgct cggctcggcg   1080
caccagggct gcctgcctcc gttcccggcg gacgtcttca tgattcctca gtacgggtac   1140
ctgactctga acaatggcag tcaggctgtg gccggtcgt ccttctactg cctggagtac   1200
tttccttctc aaatgctgag aacgggcaac aactttgaat tcagctacaa cttcgaggac   1260
gtgcccttcc acagcagcta cgcgcacagc cagagcctgg accggctgat gaaccctctc   1320
atcgaccagt acttgtacta cctgtcccgg actcaaagca cgggcggtac tgcaggaact   1380
cagcagttgc tattttctca ggccgggcct aacaacatgt cggctcaggc caagaactgg   1440 ctaccggtc cctgctaccg gcagcaacgc gtctccacga cactgtcgca gaacaacaac   1500
agcaactttg cctggacggg tgccaccaag tatcatctga atggcagaga ctctctggtg   1560
aatcctggcg ttgccatggc tacccacaag gacgacgaag agcgattttt tccatccagc   1620
ggagtcttaa tgtttgggaa acaggagct ggaaaagaca cgtggactgc atgctaacca   1680
gcgaggaaga aataaagacc accaacccag tggccacaga acagtacggc   1680
atgctaacca gcgaggaaga aataaagacc accaacccag tggccacaga acagtacggc   1740
gtggtggccg ataacctgca acagcaaaac gccgctccta ttgtagggc cgtcaatagt   1800 caaggagcct tacctggcat ggtgtggcag aaccgggacg tgtacctgca gggtcccatc   1860
tgggccaaga ttcctcatac ggacggcaac tttcatcct cgccgctgat gggaggcttt   1920
ggactgaagc atccgcctcc tcagatcctg attaaaaaca cacctgttcc cgcggatcct   1980
ccgaccacct tcaatcaggc caagctggct tctttcatca cgcagtacag taccggccag   2040
gtcagcgtgg agatcgagtg ggagctgcag aaggagaaca gcaaacgctg gaacccagag   2100
attcagtaca cttccaacta ctacaaatct acaaatgtgg actttgctgt caatactgag   2160
ggtacttatt ccgagcctcg ccccattggc accgttacc tcacccgtaa tctgtaa     2217
```

<210> SEQ ID NO 3
<211> LENGTH: 601
<212> TYPE: PRT
<213> ORGANISM: Adeno-associated virus

<400> SEQUENCE: 3

```
Thr Ala Pro Gly Lys Lys Arg Pro Val Glu Pro Ser Pro Gln Arg Ser
1               5                   10                  15

Pro Asp Ser Ser Thr Gly Ile Gly Lys Lys Gly Gln Gln Pro Ala Lys
            20                  25                  30

Lys Arg Leu Asn Phe Gly Gln Thr Gly Asp Ser Glu Ser Val Pro Asp
        35                  40                  45

Pro Gln Pro Ile Gly Glu Pro Ala Gly Pro Ser Gly Leu Gly Ser
    50                  55                  60

Gly Thr Met Ala Ala Gly Gly Ala Pro Met Ala Asp Asn Asn Glu
65                  70                  75                  80

Gly Ala Asp Gly Val Gly Ser Ser Gly Asn Trp His Cys Asp Ser
            85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125
```

-continued

```
Ser Gly Gly Ser Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Asn Phe Lys Leu Phe Asn Ile Gln Val Lys Glu Val Thr Gln Asn
            180                 185                 190

Glu Gly Thr Lys Thr Ile Ala Asn Asn Leu Thr Ser Thr Ile Gln Val
        195                 200                 205

Phe Thr Asp Ser Glu Tyr Gln Leu Pro Tyr Val Leu Gly Ser Ala His
210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
            260                 265                 270

Asn Asn Phe Glu Phe Ser Tyr Asn Phe Glu Asp Val Pro Phe His Ser
        275                 280                 285

Ser Tyr Ala His Ser Gln Ser Leu Asp Arg Leu Met Asn Pro Leu Ile
    290                 295                 300

Asp Gln Tyr Leu Tyr Tyr Leu Ser Arg Thr Gln Ser Thr Gly Gly Thr
305                 310                 315                 320

Ala Gly Thr Gln Gln Leu Leu Phe Ser Gln Ala Gly Pro Asn Asn Met
                325                 330                 335

Ser Ala Gln Ala Lys Asn Trp Leu Pro Gly Pro Cys Tyr Arg Gln Gln
            340                 345                 350

Arg Val Ser Thr Thr Leu Ser Gln Asn Asn Asn Ser Asn Phe Ala Trp
        355                 360                 365

Thr Gly Ala Thr Lys Tyr His Leu Asn Gly Arg Asp Ser Leu Val Asn
    370                 375                 380

Pro Gly Val Ala Met Ala Thr His Lys Asp Asp Glu Glu Arg Phe Phe
385                 390                 395                 400

Pro Ser Ser Gly Val Leu Met Phe Gly Lys Gln Gly Ala Gly Lys Asp
                405                 410                 415

Asn Val Asp Tyr Ser Ser Val Met Leu Thr Ser Glu Glu Ile Lys
            420                 425                 430

Thr Thr Asn Pro Val Ala Thr Glu Gln Tyr Gly Val Val Ala Asp Asn
        435                 440                 445

Leu Gln Gln Gln Asn Ala Ala Pro Ile Val Gly Ala Val Asn Ser Gln
    450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Gln Ile
            500                 505                 510

Leu Ile Lys Asn Thr Pro Val Pro Ala Asp Pro Pro Thr Thr Phe Asn
        515                 520                 525

Gln Ala Lys Leu Ala Ser Phe Ile Thr Gln Tyr Ser Thr Gly Gln Val
    530                 535                 540
```

```
Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Asn Val
                565                 570                 575

Asp Phe Ala Val Asn Thr Glu Gly Thr Tyr Ser Glu Pro Arg Pro Ile
            580                 585                 590

Gly Thr Arg Tyr Leu Thr Arg Asn Leu
            595                 600

<210> SEQ ID NO 4
<211> LENGTH: 535
<212> TYPE: PRT
<213> ORGANISM: Adeno-associated virus

<400> SEQUENCE: 4

Met Ala Ala Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
            20                  25                  30

Leu Gly Asp Arg Val Ile Thr Thr Ser Thr Arg Thr Trp Ala Leu Pro
            35                  40                  45

Thr Tyr Asn Asn His Leu Tyr Lys Gln Ile Ser Asn Gly Thr Ser Gly
50                  55                  60

Gly Ser Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
            100                 105                 110

Phe Lys Leu Phe Asn Ile Gln Val Lys Glu Val Thr Gln Asn Glu Gly
            115                 120                 125

Thr Lys Thr Ile Ala Asn Asn Leu Thr Ser Thr Ile Gln Val Phe Thr
130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
            195                 200                 205

Phe Glu Phe Ser Tyr Asn Phe Glu Asp Val Pro Phe His Ser Ser Tyr
210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Ser Thr Gly Gly Thr Ala Gly
                245                 250                 255

Thr Gln Gln Leu Leu Phe Ser Gln Ala Gly Pro Asn Asn Met Ser Ala
            260                 265                 270

Gln Ala Lys Asn Trp Leu Pro Gly Pro Cys Tyr Arg Gln Gln Arg Val
            275                 280                 285

Ser Thr Thr Leu Ser Gln Asn Asn Asn Ser Asn Phe Ala Trp Thr Gly
290                 295                 300

Ala Thr Lys Tyr His Leu Asn Gly Arg Asp Ser Leu Val Asn Pro Gly
305                 310                 315                 320
```

-continued

```
Val Ala Met Ala Thr His Lys Asp Asp Glu Glu Arg Phe Phe Pro Ser
                325                 330                 335

Ser Gly Val Leu Met Phe Gly Lys Gln Gly Ala Gly Lys Asp Asn Val
            340                 345                 350

Asp Tyr Ser Ser Val Met Leu Thr Ser Glu Glu Glu Ile Lys Thr Thr
        355                 360                 365

Asn Pro Val Ala Thr Glu Gln Tyr Gly Val Val Ala Asp Asn Leu Gln
    370                 375                 380

Gln Gln Asn Ala Ala Pro Ile Val Gly Ala Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
                420                 425                 430

Leu Met Gly Gly Phe Gly Leu Lys His Pro Pro Gln Ile Leu Ile
            435                 440                 445

Lys Asn Thr Pro Val Pro Ala Asp Pro Pro Thr Thr Phe Asn Gln Ala
    450                 455                 460

Lys Leu Ala Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Asn Val Asp Phe
                500                 505                 510

Ala Val Asn Thr Glu Gly Thr Tyr Ser Glu Pro Arg Pro Ile Gly Thr
                515                 520                 525

Arg Tyr Leu Thr Arg Asn Leu
        530                 535

<210> SEQ ID NO 5
<211> LENGTH: 738
<212> TYPE: PRT
<213> ORGANISM: Adeno-associated virus

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
```

```
            145                 150                 155                 160
        Gly Lys Lys Gly Gln Gln Pro Ala Lys Lys Arg Leu Asn Phe Gly Gln
                        165                 170                 175
        Thr Gly Asp Ser Glu Ser Val Pro Asp Pro Gln Pro Ile Gly Glu Pro
                        180                 185                 190
        Pro Ala Ala Pro Ser Gly Val Gly Pro Asn Thr Met Ala Ala Gly Gly
                        195                 200                 205
        Gly Ala Pro Met Ala Asp Asn Asn Glu Gly Ala Asp Gly Val Gly Ser
                        210                 215                 220
        Ser Ser Gly Asn Trp His Cys Asp Ser Thr Trp Leu Gly Asp Arg Val
        225                 230                 235                 240
        Ile Thr Thr Ser Thr Arg Thr Trp Ala Leu Pro Thr Tyr Asn Asn His
                        245                 250                 255
        Leu Tyr Lys Gln Ile Ser Asn Gly Thr Ser Gly Gly Ser Thr Asn Asp
                        260                 265                 270
        Asn Thr Tyr Phe Gly Tyr Ser Thr Pro Trp Gly Tyr Phe Asp Phe Asn
                        275                 280                 285
        Arg Phe His Cys His Phe Ser Pro Arg Asp Trp Gln Arg Leu Ile Asn
                        290                 295                 300
        Asn Asn Trp Gly Phe Arg Pro Lys Arg Leu Asn Phe Lys Leu Phe Asn
        305                 310                 315                 320
        Ile Gln Val Lys Glu Val Thr Gln Asn Glu Gly Thr Lys Thr Ile Ala
                        325                 330                 335
        Asn Asn Leu Thr Ser Thr Ile Gln Val Phe Thr Asp Ser Glu Tyr Gln
                        340                 345                 350
        Leu Pro Tyr Val Leu Gly Ser Ala His Gln Gly Cys Leu Pro Pro Phe
                        355                 360                 365
        Pro Ala Asp Val Phe Met Ile Pro Gln Tyr Gly Tyr Leu Thr Leu Asn
                        370                 375                 380
        Asn Gly Ser Gln Ala Val Gly Arg Ser Ser Phe Tyr Cys Leu Glu Tyr
        385                 390                 395                 400
        Phe Pro Ser Gln Met Leu Arg Thr Gly Asn Asn Phe Glu Phe Ser Tyr
                        405                 410                 415
        Asn Phe Glu Asp Val Pro Phe His Ser Ser Tyr Ala His Ser Gln Ser
                        420                 425                 430
        Leu Asp Arg Leu Met Asn Pro Leu Ile Asp Gln Tyr Leu Tyr Tyr Leu
                        435                 440                 445
        Ser Arg Thr Gln Ser Thr Gly Gly Thr Ala Gly Thr Gln Gln Leu Leu
        450                 455                 460
        Phe Ser Gln Ala Gly Pro Asn Asn Met Ser Ala Gln Ala Lys Asn Trp
        465                 470                 475                 480
        Leu Pro Gly Pro Cys Tyr Arg Gln Gln Arg Val Ser Thr Thr Leu Ser
                        485                 490                 495
        Gln Asn Asn Asn Ser Asn Phe Ala Trp Thr Gly Ala Thr Lys Tyr His
                        500                 505                 510
        Leu Asn Gly Arg Asp Ser Leu Val Asn Pro Gly Val Ala Met Ala Thr
                        515                 520                 525
        His Lys Asp Asp Glu Glu Arg Phe Phe Pro Ser Ser Gly Val Leu Met
                        530                 535                 540
        Phe Gly Lys Gln Gly Ala Gly Lys Asp Asn Val Asp Tyr Ser Ser Val
        545                 550                 555                 560
        Met Leu Thr Ser Glu Glu Ile Lys Thr Thr Asn Pro Val Ala Thr
                        565                 570                 575
```

-continued

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 6
<211> LENGTH: 738
<212> TYPE: PRT
<213> ORGANISM: Adeno-associated virus

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Arg Gln Asp Asn Gly Arg Gly Leu Val Leu Pro
        35                  40                  45

Gly Tyr Arg Tyr Leu Gly Pro Phe Asn Gly Leu Asp Lys Gly Glu Pro
    50                  55                  60

Val Asn Ala Ala Asp Ala Ala Leu Glu His Asp Arg Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Arg Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

```
Gly Ala Pro Met Ala Asp Asn Asn Glu Gly Ala Asp Gly Val Gly Ser
        210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Arg Gln Ile Ser Asn Gly Thr Ser Gly Gly Ser Thr Asn Asp
                260                 265                 270
Asn Thr Tyr Phe Gly Tyr Ser Thr Pro Trp Gly Tyr Phe Asp Phe Asn
            275                 280                 285
Arg Phe His Cys His Phe Ser Pro Arg Asp Trp Gln Arg Leu Ile Asn
        290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Arg Thr Ile Ala
                325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
            355                 360                 365
Pro Ala Asp Val Phe Met Ile Pro Gln Tyr Gly Tyr Leu Thr Leu Asn
        370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Asn Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
            435                 440                 445
Ser Arg Thr Gln Ser Thr Gly Gly Thr Ala Gly Thr Gln Gln Leu Leu
        450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
            515                 520                 525
His Arg Asp Asp Glu Glu Arg Phe Phe Pro Ser Ser Gly Val Leu Met
        530                 535                 540
Phe Gly Arg Gln Gly Ala Gly Arg Asp Asn Val Asp Tyr Ser Ser Val
545                 550                 555                 560
Met Leu Thr Ser Glu Glu Ile Arg Thr Thr Asn Pro Val Ala Thr
                565                 570                 575
Glu Gln Tyr Gly Val Val Ala Asp Asn Leu Gln Gln Asn Ala Ala
            580                 585                 590
Pro Ile Val Gly Ala Val Asn Ser Gln Gly Ala Leu Pro Gly Met Val
            595                 600                 605
Trp Gln Asn Arg Asp Val Tyr Leu Gln Gly Pro Ile Trp Ala Lys Ile
        610                 615                 620
```

-continued

```
Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu
```

<210> SEQ ID NO 7
<211> LENGTH: 738
<212> TYPE: PRT
<213> ORGANISM: Adeno-associated virus

<400> SEQUENCE: 7

```
Met Ala Ala Asp Gly Tyr Leu Pro Asp Trp Leu Glu Asp Asn Leu Ser
1                   5                   10                  15

Glu Gly Ile Arg Glu Trp Trp Asp Leu Lys Pro Gly Ala Pro Lys Pro
                20                  25                  30

Lys Ala Asn Gln Gln Arg Gln Asp Asn Gly Arg Gly Leu Val Leu Pro
            35                  40                  45

Gly Tyr Arg Tyr Leu Gly Pro Phe Asn Gly Leu Asp Lys Gly Glu Pro
        50                  55                  60

Val Asn Ala Ala Asp Ala Ala Ala Leu Glu His Asp Arg Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Arg Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Arg Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255
```

-continued

```
Leu Tyr Arg Gln Ile Ser Asn Gly Thr Ser Gly Ser Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Arg Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Arg Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Arg Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
```

-continued

```
                675                 680                 685
Leu Gln Lys Glu Asn Ser Lys Arg Trp Asn Pro Glu Ile Gln Tyr Thr
        690                 695                 700
Ser Asn Tyr Tyr Lys Ser Thr Asn Val Asp Phe Ala Val Asn Thr Glu
705                 710                 715                 720
Gly Thr Tyr Ser Glu Pro Arg Pro Ile Gly Thr Arg Tyr Leu Thr Arg
                725                 730                 735
Asn Leu

<210> SEQ ID NO 8
<211> LENGTH: 738
<212> TYPE: PRT
<213> ORGANISM: Adeno-associated virus

<400> SEQUENCE: 8

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Arg Gln Asp Asn Gly Arg Gly Leu Val Leu Pro
        35                  40                  45
Gly Tyr Arg Tyr Leu Gly Pro Phe Asn Gly Leu Asp Lys Gly Glu Pro
    50                  55                  60
Val Asn Ala Ala Asp Ala Ala Leu Glu His Asp Arg Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Ser Pro Val Arg Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Arg Gly Gln Gln Pro Ala Lys Lys Arg Leu Asn Phe Gly Gln
                165                 170                 175
Thr Gly Asp Ser Glu Ser Val Pro Asp Pro Gln Pro Ile Gly Glu Pro
            180                 185                 190
Pro Ala Ala Pro Ser Gly Val Gly Pro Asn Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Arg Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
```

-continued

```
               305                 310                 315                 320
        Ile Gln Val Lys Glu Val Thr Gln Asn Glu Gly Thr Arg Thr Ile Ala
                        325                 330                 335
        Asn Asn Leu Thr Ser Thr Ile Gln Val Phe Thr Asp Ser Glu Tyr Gln
                        340                 345                 350
        Leu Pro Tyr Val Leu Gly Ser Ala His Gln Gly Cys Leu Pro Pro Phe
                        355                 360                 365
        Pro Ala Asp Val Phe Met Ile Pro Gln Tyr Gly Tyr Leu Thr Leu Asn
                        370                 375                 380
        Asn Gly Ser Gln Ala Val Gly Arg Ser Ser Phe Tyr Cys Leu Glu Tyr
        385                 390                 395                 400
        Phe Pro Ser Gln Met Leu Arg Thr Gly Asn Asn Phe Glu Phe Ser Tyr
                        405                 410                 415
        Asn Phe Glu Asp Val Pro Phe His Ser Ser Tyr Ala His Ser Gln Ser
                        420                 425                 430
        Leu Asp Arg Leu Met Asn Pro Leu Ile Asp Gln Tyr Leu Tyr Tyr Leu
                        435                 440                 445
        Ser Arg Thr Gln Ser Thr Gly Gly Thr Ala Gly Thr Gln Gln Leu Leu
                        450                 455                 460
        Phe Ser Gln Ala Gly Pro Asn Asn Met Ser Ala Gln Ala Lys Asn Trp
        465                 470                 475                 480
        Leu Pro Gly Pro Cys Tyr Arg Gln Gln Arg Val Ser Thr Thr Leu Ser
                        485                 490                 495
        Gln Asn Asn Asn Ser Asn Phe Ala Trp Thr Gly Ala Thr Lys Tyr His
                        500                 505                 510
        Leu Asn Gly Arg Asp Ser Leu Val Asn Pro Gly Val Ala Met Ala Thr
                        515                 520                 525
        His Arg Asp Asp Glu Glu Arg Phe Phe Pro Ser Ser Gly Val Leu Met
                        530                 535                 540
        Phe Gly Arg Gln Gly Ala Gly Arg Asp Asn Val Asp Tyr Ser Ser Val
        545                 550                 555                 560
        Met Leu Thr Ser Glu Glu Glu Ile Arg Thr Thr Asn Pro Val Ala Thr
                        565                 570                 575
        Glu Gln Tyr Gly Val Val Ala Asp Asn Leu Gln Gln Asn Ala Ala
                        580                 585                 590
        Pro Ile Val Gly Ala Val Asn Ser Gln Gly Ala Leu Pro Gly Met Val
                        595                 600                 605
        Trp Gln Asn Arg Asp Val Tyr Leu Gln Gly Pro Ile Trp Ala Lys Ile
                        610                 615                 620
        Pro His Thr Asp Gly Asn Phe His Pro Ser Pro Leu Met Gly Gly Phe
        625                 630                 635                 640
        Gly Leu Lys His Pro Pro Gln Ile Leu Ile Lys Asn Thr Pro Val
                        645                 650                 655
        Pro Ala Asp Pro Pro Thr Thr Phe Asn Gln Ala Lys Leu Ala Ser Phe
                        660                 665                 670
        Ile Thr Gln Tyr Ser Thr Gly Gln Val Ser Val Glu Ile Glu Trp Glu
                        675                 680                 685
        Leu Gln Lys Glu Asn Ser Lys Arg Trp Asn Pro Glu Ile Gln Tyr Thr
                        690                 695                 700
        Ser Asn Tyr Tyr Lys Ser Thr Asn Val Asp Phe Ala Val Asn Thr Glu
        705                 710                 715                 720
        Gly Thr Tyr Ser Glu Pro Arg Pro Ile Gly Thr Arg Tyr Leu Thr Arg
                        725                 730                 735
```

Asn Leu

<210> SEQ ID NO 9
<211> LENGTH: 738
<212> TYPE: PRT
<213> ORGANISM: Adeno-associated virus

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Arg Gln Asp Asn Gly Arg Gly Leu Val Leu Pro
        35                  40                  45

Gly Tyr Arg Tyr Leu Gly Pro Phe Asn Gly Leu Asp Lys Gly Glu Pro
50                  55                  60

Val Asn Ala Ala Asp Ala Ala Ala Leu Glu His Asp Arg Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Arg Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Arg Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Arg Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Arg Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365
```

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Asn Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
    435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
            485                 490                 495

Gln Asn Asn Asn Ser Asn Phe Ala Trp Thr Gly Ala Thr Lys Tyr His
        500                 505                 510

Leu Asn Gly Arg Asp Ser Leu Val Asn Pro Gly Val Ala Met Ala Thr
    515                 520                 525

His Arg Asp Asp Glu Glu Arg Phe Phe Pro Ser Ser Gly Val Leu Met
530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Arg Thr Thr Asn Pro Val Ala Thr
            565                 570                 575

Glu Gln Tyr Gly Val Val Ala Asp Asn Leu Gln Gln Gln Asn Ala Ala
        580                 585                 590

Pro Ile Val Gly Ala Val Asn Ser Gln Gly Ala Leu Pro Gly Met Val
    595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650                 655

Pro Ala Asp Pro Pro Thr Thr Phe Asn Gln Ala Arg Leu Ala Ser Phe
        660                 665                 670

Ile Thr Gln Tyr Ser Thr Gly Gln Val Ser Val Glu Ile Glu Trp Glu
    675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 10
<211> LENGTH: 738
<212> TYPE: PRT
<213> ORGANISM: Adeno-associated virus

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Arg Gln Asp Asn Gly Arg Gly Leu Val Leu Pro
            35                  40                  45

Gly Tyr Arg Tyr Leu Gly Pro Phe Asn Gly Leu Asp Lys Gly Glu Pro
50                  55                  60

Val Asn Ala Ala Asp Ala Ala Ala Leu Glu His Asp Arg Ala Tyr Asp
65                  70                  75                  80

Gln Gln Leu Gln Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Ser Pro Val Arg Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
                195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Arg Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Arg Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415
```

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Arg Asp Asp Glu Glu Arg Phe Phe Pro Ser Ser Gly Val Leu Met
    530                 535                 540

Phe Gly Arg Gln Gly Ala Gly Arg Asp Asn Val Asp Tyr Ser Ser Val
545                 550                 555                 560

Met Leu Thr Ser Glu Glu Glu Ile Arg Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Arg Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 11
<211> LENGTH: 2214
<212> TYPE: DNA
<213> ORGANISM: Adeno-associated virus

<400> SEQUENCE: 11
atggctgccg atggttatct tccagattgg ctcgaggaca acctctctga gggcattcgc    60
gagtggtggg acctgaaacc tggagccccg aaacccaaag ccaaccagca aaagcaggac   120
aacggccggg gtctggtgct tcctggctac aagtacctcg gacccttcaa cggactcgac   180
aagggggagc ccgtcaacgc ggcggacgca gcggccctcg agcacgacaa ggcctacgac   240
cagcagctcc aagcgggtga caatccgtac ctgcggtata tcacgccga cgccgagttt   300

-continued

```
caggagcgtc tgcaagaaga tacgtctttt gggggcaacc tcgggcgcgc agtcttccag      360
gccaaaaagc gggttctcga acctctgggc ctggttgaat cgccggttaa gacggctcct      420
ggaaagaaga gaccggtaga gccatcaccc cagcgctctc cagactcctc tacgggcatc      480
ggcaagaaag gccagcagcc cgcaaaaaag agactcaatt ttgggcagac tggcgactca      540
gagtcagtcc ccgaccctca accaatcgga gaaccaccag cagcccctc tggtgtggga       600 cctaatacaa tggctgcagg cggtggcgct ccaatggcag acaataacga aggcgccgac      660
ggagtgggta gttcctcagg aaattggcat gcgattcca catggctggg cgacagagtc       720
atcaccacca gcacccgcac ctgggccctg cccacctaca caaccaccct ctacaagcaa      780
atctccaacg ggacctcggg aggaagcacc aacgacaaca cctacttcgg ctacagcacc      840
ccctgggggt attttgactt caacagattc cactgccact tttcaccacg tgactggcag      900
cgactcatca acaacaactg gggattccgg cccaagaggc tcaacttcaa gctcttcaac      960
atccaagtca aggaggtcac gcagaatgaa ggcaccaaga ccatcgccaa taaccttacc     1020
agcacgattc aggtctttac ggactcggaa taccagctcc cgtacgtgct cggctcggcg     1080
caccagggct gcctgcctcc gttcccggcg gacgtcttca tgattcctca gtacgggtac     1140
ctgactctga acaatggcag tcaggctgtg gccggtcgt ccttctactg cctggagtac      1200
tttccttctc aaatgctgag aacgggcaac aactttgaat tcagctacaa cttcgaggac     1260
gtgcccttcc acagcagcta cgcgcacagc cagagcctgg accggctgat gaaccctctc     1320
atcgaccagt acttgtacta cctgtcccgg actcaaagca cggcggtac tgcaggaact      1380 cagcagttgc tattttctca ggccgggcct aacaacatgt cggctcaggc caagaactgg     1440
ctacccggtc cctgctaccg gcagcaacgc gtctccacga cactgtcgca gaacaacaac     1500
agcaactttg cctggacggg tgccaccaag tatcatctga atggcagaga ctctctggtg     1560
aatcctggcg ttgccatggc tacccacaag gacgacgaag agcgattttt tccatccagc     1620
ggagtcttaa tgtttgggaa acagggagct ggaaaagaca acgtggacta tagcagcgtg     1680
atgctaacca gcgaggaaga aataaagacc accaacccag tggccacaga acagtacggc     1740
gtggtggccg ataacctgca acagcaaaac gccgctccta ttgtagggggc cgtcaatagt     1800 caaggagcct tacctggcat ggtgtggcag aaccgggacg tgtacctgca gggtcccatc     1860
tgggccaaga ttcctcatac ggacggcaac tttcatcct cgccgctgat gggaggcttt     1920
ggactgaagc atccgcctcc tcagatcctg attaaaaaca cacctgttcc cgcggatcct     1980
ccgaccacct tcaatcaggc caagctggct ctttcatca cgcagtacag taccggccag     2040
gtcagcgtgg agatcgagtg ggagctgcag aaggagaaca gcaaacgctg gaacccagag     2100
attcagtaca cttccaacta ctacaaatct acaaatgtgg actttgctgt caatactgag     2160
ggtacttatt ccgagcctcg ccccattggc acccgttacc tcacccgtaa tctg          2214
```

<210> SEQ ID NO 12
<211> LENGTH: 2217
<212> TYPE: DNA
<213> ORGANISM: Adeno-associated virus

<400> SEQUENCE: 12

```
atggctgccg atggttatct tccagattgg ctcgaggaca acctctctga gggcattcgc       60
gagtggtggg acctgaaacc tggagccccg aaacccaaag ccaaccagca aaggcaggac      120
aacgccgggg gtctggtgct tcctggctac aggtacctcg gacccttcaa cggactcgac      180
```

```
aaggggggagc ccgtcaacgc ggcggacgca gcggccctcg agcacgacag ggcctacgac      240
cagcagctcc aagcgggtga caatccgtac ctgcggtata atcacgccga cgccgagttt      300
caggagcgtc tgcaagaaga tacgtctttt gggggcaacc tcgggcgcgc agtcttccag      360
gccaaaaagc gggttctcga acctctgggc ctggttgaat cgccggttag gacggctcct      420
ggaaagaaga gaccggtaga gccatcaccc cagcgctctc cagactcctc tacgggcatc      480
ggcaagaaag gccagcagcc cgcaagaaag agactcaatt ttgggcagac tggcgactca      540
gagtcagtcc ccgaccctca accaatcgga gaaccaccag cagcccctc tggtgtggga      600 cctaatacaa tggctgcagg cggtggcgct ccaatggcag acaataacga aggcgccgac      660
ggagtgggta gttcctcagg aaattggcat tgcgattcca catggctggg cgacagagtc      720
atcaccacca gcacccgcac ctgggccctg cccacctaca caaccaccct ctacaggcaa      780
atctccaacg ggacctcggg aggaagcacc aacgacaaca cctacttcgg ctacagcacc      840 cctgggggt atttgactt caacagattc cactgccact tttcaccacg tgactggcag      900
cgactcatca acaacaactg gggattccgg cccaagaggc tcaacttcaa gctcttcaac      960
atccaagtca aggaggtcac gcagaatgaa ggcaccagga ccatcgccaa taacctacc     1020 agcacgattc aggtctttac ggactcggaa taccagctcc cgtacgtgct cggctcggcg     1080
caccagggct gcctgcctcc gttccggcg gacgtcttca tgattcctca gtacgggtac     1140
ctgactctga acaatggcag tcaggctgtg ggccggtcgt ccttctactg cctggagtac     1200
tttccttctc aaatgctgag aacgggcaac aactttgaat tcagctacaa cttcgaggac     1260
gtgcccttcc acagcagcta cgcgcacagc cagagcctgg accggctgat gaaccctctc     1320
atcgaccagt acttgtacta cctgtcccgg actcaaagca cgggcggtac tgcaggaact     1380
cagcagttgc tattttctca ggccgggcct aacaacatgt cggctcaggc caagaactgg     1440
ctacccggtc cctgctaccg gcagcaacgc gtctccacga cactgtcgca gaacaacaac     1500
agcaactttg cctggacggg tgccaccaag tatcatctga atggcagaga ctctctggtg     1560
aatcctggcg ttgccatggc tacccacagg gacgacgaag agcgattttt tccatccagc     1620
ggagtcttaa tgtttgggag acaggagct ggaagagaca cgtggacta tagcagcgtg     1680 atgctaacca gcgaggaaga aataaggacc accaacccag tggccacaga acagtacggc     1740
gtggtggccg ataacctgca acagcaaaac gccgctccta ttgtagggc cgtcaatagt     1800 caaggagcct tacctggcat ggtgtggcag aaccgggacg tgtacctgca gggtcccatc     1860
tgggccaaga ttcctcatac ggacggcaac tttcatcct cgccgctgat gggaggcttt     1920
ggactgaagc atccgcctcc tcagatcctg attaaaaaca cacctgttcc cgcggatcct     1980
ccgaccacct tcaatcaggc caagctggct tctttcatca gcagtacag taccggccag     2040 gtcagcgtgg agatcgagtg ggagctgcag aaggagaaca gcaaacgctg gaacccagag     2100
attcagtaca cttccaacta ctacaaatct acaaatgtgg actttgctgt caatactgag     2160
ggtacttatt ccgagcctcg ccccattggc acccgttacc tcacccgtaa tctgtaa      2217
```

<210> SEQ ID NO 13
<211> LENGTH: 2217
<212> TYPE: DNA
<213> ORGANISM: Adeno-associated virus

<400> SEQUENCE: 13

```
atggctgccg atggttatct tccagattgg ctcgaggaca acctctctga ggcattcgc       60 gagtggtggg acctgaaacc tggagccccg aaacccaaag ccaaccagca aaggcaggac     120
```

```
aacggccggg gtctggtgct tcctggctac aggtacctcg gacccttcaa cggactcgac    180
aagggggagc ccgtcaacgc ggcggacgca gcggcccctcg agcacgacag ggcctacgac    240
cagcagctcc aagcgggtga caatccgtac ctgcggtata atcacgccga cgccgagttt    300
caggagcgtc tgcaagaaga tacgtctttt gggggcaacc tcgggcgcgc agtcttccag    360
gccaaaaagc gggttctcga acctctgggc ctggttgaat cgccggttag gacggctcct    420
ggaaagaaga gaccggtaga gccatcaccc cagcgctctc cagactcctc tacgggcatc    480
ggcaagagag gccagcagcc cgcaagaaag agactcaatt ttgggcagac tggcgactca    540
gagtcagtcc ccgaccctca accaatcgga gaaccaccag cagcccctc tggtgtggga    600
cctaatacaa tggctgcagg cggtggcgct ccaatggcag acaataacga aggcgccgac    660
ggagtgggta gttcctcagg aaattggcat gcgattcca catggctggg cgacagagtc    720
atcaccacca gcacccgcac ctgggccctg cccacctaca caaccaccct ctacaggcaa    780
atctccaacg gacctcgggg aggaagcacc aacgacaaca cctacttcgg ctacagcacc    840
ccctgggggt attttgactt caacagattc cactgccact tttcaccacg tgactggcag    900
cgactcatca caacaactg gggattccgg cccaagaggc tcaacttcaa gctcttcaac    960
atccaagtca aggaggtcac gcagaatgaa ggcaccagga ccatcgccaa taaccttacc    1020
agcacgattc aggtctttac ggactcggaa taccagctcc cgtacgtgct cggctcggcg    1080
caccagggct gcctgcctcc gttcccggcg gacgtcttca tgattcctca gtacgggtac    1140
ctgactctga acaatggcag tcaggctgtg ggccggtcgt ccttctactg cctggagtac    1200
tttccttctc aaatgctgag aacgggcaac aactttgaat tcagctacaa cttcgaggac    1260
gtgcccttcc acagcagcta cgcgcacagc cagagcctgg accggctgat gaaccctctc    1320
atcgaccagt acttgtacta cctgtcccgg actcaaagca cgggcggtac tgcaggaact    1380
cagcagttgc tattttctca ggccgggcct aacaacatgt cggctcaggc caagaactgg    1440
ctacccggtc cctgctaccg gcagcaacgc gtctccacga cactgtcgca gaacaacaac    1500
agcaactttg cctggacggg tgccaccaag tatcatctga atggcagaga ctctctggtg    1560
aatcctggcg ttgccatggc tacccacagg gacgacgaag agcgattttt tccatccagc    1620
ggagtcttaa tgtttgggaa cagggagct ggaagagaca acgtggacta tagcagcgtg    1680
atgctaacca gcgaggaaga aataaggacc accaacccag tggccacaga acagtacggc    1740
gtggtggccg ataacctgca acagcaaaac gccgctccta ttgtaggggc cgtcaatagt    1800
caaggagcct tacctggcat ggtgtggcag aaccggacg tgtacctgca gggtcccatc    1860
tgggccaaga ttcctcatac ggacggcaac tttcatccct cgccgctgat gggaggcttt    1920
ggactgaagc atccgcctcc tcagatcctg attaaaaaca cacctgttcc gcggatcct    1980
ccgaccacct tcaatcaggc caagctggct tctttcatca cgcagtacag taccggccag    2040
gtcagcgtgg agatcgagtg ggagctgcag aaggagaaca gcaaacgctg gaacccagag    2100
attcagtaca cttccaacta ctacaaatct acaaatgtgg actttgctgt caatactgag    2160
ggtacttatt ccgagcctcg cccccattggc acccgttacc tcacccgtaa tctgtaa    2217
```

<210> SEQ ID NO 14
<211> LENGTH: 2217
<212> TYPE: DNA
<213> ORGANISM: Adeno-associated virus

<400> SEQUENCE: 14

```
atggctgccg atggttatct tccagattgg ctcgaggaca acctctctga gggcattcgc    60
gagtggtggg acctgaaacc tggagccccg aaacccaaag ccaaccagca aaggcaggac   120
aacggccggg gtctggtgct tcctggctac aggtacctcg acccttcaa cggactcgac   180
aaggggagc ccgtcaacgc ggcggacgca gcggccctcg agcacgacag ggcctacgac   240
cagcagctcc aagcgggtga caatccgtac ctgcggtata atcacgccga cgccgagttt   300
caggagcgtc tgcaagaaga tacgtctttt gggggcaacc tcgggcgcgc agtcttccag   360
gccaaaaagc gggttctcga acctctgggc ctggttgaat cgccggttag gacggctcct   420
ggaaagaaga ccggtagaa gccatcaccc cagcgctctc cagactcctc tacgggcatc   480
ggcaagagag gccagcagcc cgcaaaaaag agactcaatt ttgggcagac tggcgactca   540
gagtcagtcc ccgaccctca accaatcgga gaaccaccag cagcccctc tggtgtggga   600
cctaatacaa tggctgcagg cggtggcgct ccaatggcag acaataacga aggcgccgac   660
ggagtgggta gttcctcagg aaattggcat gcgattccaa catggctggg cgacagagtc   720
atcaccacca gcacccgcac ctgggccctg cccacctaca caaccaccct ctacaggcaa   780
atctccaacg ggacctcggg aggaagcacc aacgacaaca cctacttcgg ctacagcacc   840
cccctggggg atttttgactt caacagattc cactgccact tttccaccac tgactggcag   900
cgactcatca caacaactg gggattccgg cccaagaggc tcaacttcaa gctcttcaac   960
atccaagtca aggaggtcac gcagaatgaa ggcaccagga ccatcgccaa taccttacc  1020
agcacgattc aggtctttac ggactcggaa taccagctcc cgtacgtgct cggctcggcg  1080
caccagggct gcctgcctcc gttcccggcg gacgtcttca tgattcctca gtacgggtac  1140
ctgactctga acaatggcag tcaggctgtg ggccggtcgt ccttctactg cctggagtac  1200
tttccttctc aaatgctgag aacgggcaac aactttgaat tcagctacaa cttcgaggac  1260
gtgcccttcc acagcagcta cgcgcacagc cagagcctgg accggctgat gaaccctctc  1320
atcgaccagt acttgtacta cctgtcccgg actcaaagca cgggcggtac tgcaggaact  1380
cagcagttgc tattttctca ggccgggcct aacaacatgt cggctcaggc caagaactgg  1440
ctacccggtc cctgctaccg gcagcaacgc gtctccacga cactgtcgca gaacaacaac  1500
agcaactttg cctggacggg tgccaccaag tatcatctga atggcagaga ctctctggtg  1560
aatcctggcg ttgccatggc tacccacagg gacgacgaag agcgatttc tccatccagc  1620
ggagtcttaa tgtttgggag acagggagct ggaagagaca acgtggacta tagcagcgtg  1680
atgctaacca gcgaggaaga aataaggacc accaacccag tggccacaga acagtacggc  1740
gtggtggccg ataacctgca acagcaaaac gccgctccta ttgtaggggc cgtcaatagt  1800
caaggagcct tacctggcat ggtgtggcag aaccggacg tgtacctgca gggtcccatc  1860
tgggccaaga ttcctcatac ggacggcaac tttcatccct cgccgctgat gggaggcttt  1920
ggactgaagc atccgcctcc tcagatcctg attaaaaaca cacctgttcc cgcggatcct  1980
ccgaccacct tcaatcaggc caagctggct tctttcatca cgcagtacag taccggccag  2040
gtcagcgtgg agatcgagtg ggagctgcag aaggagaaca gcaaacgctg gaacccagag  2100
attcagtaca cttccaacta ctacaaatct acaaatgtgg actttgctgt caatactgag  2160
ggtacttatt ccgagcctcg ccccattggc accgttaccc tcacccgtaa tctgtaa     2217

<210> SEQ ID NO 15
<211> LENGTH: 2217
<212> TYPE: DNA
<213> ORGANISM: Adeno-associated virus
```

<400> SEQUENCE: 15

| | | | | | |
|---|---|---|---|---|---|
| atggctgccg | atggttatct | tccagattgg | ctcgaggaca | acctctctga | gggcattcgc | 60 |
| gagtggtggg | acctgaaacc | tggagccccg | aaacccaaag | ccaaccagca | aaggcaggac | 120 |
| aacggccggg | gtctggtgct | tcctggctac | aggtacctcg | gacccttcaa | cggactcgac | 180 |
| aaggggagc | ccgtcaacgc | ggcggacgca | gcggccctcg | agcacgacag | ggcctacgac | 240 |
| cagcagctcc | aagcgggtga | caatccgtac | ctgcggtata | atcacgccga | cgccgagttt | 300 |
| caggagcgtc | tgcaagaaga | tacgtctttt | gggggcaacc | tcgggcgcgc | agtcttccag | 360 |
| gccaaaaagc | gggttctcga | acctctgggc | ctggttgaat | cgccggttag | gacggctcct | 420 |
| ggaaagaaga | gaccggtaga | gccatcaccc | cagcgctctc | cagactcctc | tacgggcatc | 480 |
| ggcaagagag | ccagcagcc | cgcaaaaaag | agactcaatt | ttgggcagac | tggcgactca | 540 |
| gagtcagtcc | ccgaccctca | accaatcgga | gaaccaccag | cagcccctc | tggtgtggga | 600 |
| cctaatacaa | tggctgcagg | cggtggcgct | ccaatggcag | acaataacga | aggcgccgac | 660 |
| ggagtgggta | gttcctcagg | aaattggcat | tgcgattcca | catggctggg | cgacagagtc | 720 |
| atcaccacca | gcacccgcac | ctgggccctg | cccacctaca | caaccaccct | ctacaggcaa | 780 |
| atctccaacg | ggacctcggg | aggaagcacc | aacgacaaca | cctacttcgg | ctacagcacc | 840 |
| ccctgggggt | attttgactt | caacagattc | cactgccact | tttcaccacg | tgactggcag | 900 |
| cgactcatca | acaacaactg | gggattccgg | cccaagaggc | tcaacttcaa | gctcttcaac | 960 |
| atccaagtca | aggaggtcac | gcagaatgaa | ggcaccagga | ccatcgccaa | taaccttacc | 1020 |
| agcacgattc | aggtctttac | ggactcggaa | taccagctcc | cgtacgtgct | cggctcggcg | 1080 |
| caccagggct | gcctgcctcc | gttcccggcg | gacgtcttca | tgattcctca | gtacgggtac | 1140 |
| ctgactctga | acaatggcag | tcaggctgtg | ggccggtcgt | ccttctactg | cctggagtac | 1200 |
| tttccttctc | aaatgctgag | aacgggcaac | aactttgaat | tcagctacaa | cttcgaggac | 1260 |
| gtgcccttcc | acagcagcta | cgcgcacagc | cagagcctgg | accggctgat | gaaccctctc | 1320 |
| atcgaccagt | acttgtacta | cctgtcccgg | actcaaagca | cgggcggtac | tgcaggaact | 1380 |
| cagcagttgc | tattttctca | ggccgggcct | aacaacatgt | cggctcaggc | caagaactgg | 1440 |
| ctacccggtc | cctgctaccg | gcagcaacgc | gtctccacga | cactgtcgca | gaacaacaac | 1500 |
| agcaactttg | cctggacggg | tgccaccaag | tatcatctga | atggcagaga | ctctctggtg | 1560 |
| aatcctggcg | ttgccatggc | tacccacagg | gacgacgaag | agcgattttt | tccatccagc | 1620 |
| ggagtcttaa | tgtttgggaa | acagggagct | ggaagagaca | acgtggacta | tagcagcgtg | 1680 |
| atgctaacca | gcgaggaaga | aataaggacc | accaacccag | tggccacaga | acagtacggc | 1740 |
| gtggtggccg | ataacctgca | acagcaaaac | gccgctccta | ttgtaggggc | cgtcaatagt | 1800 |
| caaggagcct | tacctggcat | ggtgtggcag | aaccgggacg | tgtacctgca | gggtcccatc | 1860 |
| tgggccaaga | ttcctcatac | ggacggcaac | tttcatccct | cgccgctgat | gggaggcttt | 1920 |
| ggactgaagc | atccgcctcc | tcagatcctg | attaaaaaca | cacctgttcc | cgcggatcct | 1980 |
| ccgaccacct | tcaatcaggc | caggctggct | tctttcatca | cgcagtacag | taccggccag | 2040 |

```
gtcagcgtgg agatcgagtg ggagctgcag aaggagaaca gcaaacgctg gaacccagag    2100
attcagtaca cttccaacta ctacaaatct acaaatgtgg actttgctgt caatactgag    2160
ggtacttatt ccgagcctcg ccccattggc acccgttacc tcacccgtaa tctgtaa      2217

<210> SEQ ID NO 16
<211> LENGTH: 2217
<212> TYPE: DNA
<213> ORGANISM: Adeno-associated virus

<400> SEQUENCE: 16
atggctgccg atggttatct tccagattgg ctcgaggaca acctctctga gggcattcgc      60
gagtggtggg acctgaaacc tggagccccg aaacccaaag ccaaccagca aaggcaggac     120
aacggccggg tctggtgctt cctggctac aggtacctcg gacccttcaa cggactcgac      180
aagggggagc ccgtcaacgc ggcggacgca gcggccctcg agcacgacag gcctacgac      240 cagcagctcc aagcgggtga caatccgtac ctgcggtata atcacgccga cgccgagttt     300
caggagcgtc tgcaagaaga tacgtctttt ggggcaacc tcgggcgcgc agtcttccag      360
gccaaaaagc gggttctcga acctctgggc ctggttgaat cgccggttag acggctcct      420 ggaaagaaga gaccggtaga gccatcaccc cagcgctctc cagactcctc tacgggcatc     480
ggcaagaaag ccagcagcc cgcaaaaaag agactcaatt ttgggcagac tggcgactca     540
gagtcagtcc ccgaccctca accaatcgga gaaccaccag cagcccctc tggtgtggga      600 cctaatacaa tggctgcagg cggtggcgct ccaatggcag acaataacga aggcgccgac     660
ggagtgggta gttcctcagg aaattggcat gcgattccca catggctggg cgacagagtc     720
atcaccacca gcacccgcac ctgggcctg cccacctaca acaaccacct ctacaggcaa     780
atctccaacg gaacctcggg aggaagcacc aacgacaaca cctacttcgg ctacagcacc     840
ccctgggggt attttgactt caacagattc cactgccact tttcaccacg tgactggcag      900
cgactcatca caacaactg gggattccgg cccaagaggc tcaacttcaa gctcttcaac     960
atccaagtca aggaggtcac gcagaatgaa ggcaccagga ccatcgccaa taacctacc    1020 agcacgattc aggtctttac ggactcggaa taccagctcc cgtacgtgct cggctcggcg    1080
caccagggct gcctgcctcc gttcccggcg gacgtcttca tgattcctca gtacgggtac    1140
ctgactctga acaatggcag tcaggctgtg ggccggtcgt ccttctactg cctggagtac    1200
tttccttctc aaatgctgag aacgggcaac aactttgaat tcagctacaa cttcgaggac    1260
gtgcccttcc acagcagcta cgcgcacagc cagagcctgg accggctgat gaaccctctc    1320
atcgaccagt acttgtacta cctgtcccgg actcaaagca cgggcggtac tgcaggaact    1380
cagcagttgc tattttctca ggccgggcct aacaacatgt cggctcaggc caagaactgg    1440
ctacccggtc cctgctaccg gcagcaacgc gtctccacga cactgtcgca gaacaacaac    1500
agcaactttg cctggacggg tgccaccaag tatcatctga atggcagaga ctctctggtg    1560
aatcctggcg ttgccatggc tacccacagg acgacgaag agcgattttt ccatccagc     1620 ggagtcttaa tgtttgggag cagggagct ggaagagaca cgtggacta tagcagcgtg    1680 atgctaacca gcgaggaaga aataaggacc accaacccag tggccacaga acagtacggc    1740
gtggtggccg ataacctgca acagcaaaac gccgctccta ttgtaggggc cgtcaatagt    1800
caaggagcct tacctggcat ggtgtggcag aacggacg tgtacctgca gggtcccatc    1860
tgggccaaga ttcctcatac ggacggcaac tttcatcct cgcgctgat gggaggcttt    1920 ggactgaagc atccgcctcc tcagatcctg attaaaaaca cacctgttcc cgcggatcct    1980
```

```
ccgaccacct tcaatcaggc caggctggct tctttcatca cgcagtacag taccggccag    2040
gtcagcgtgg agatcgagtg ggagctgcag aaggagaaca gcaaacgctg gaacccagag    2100
attcagtaca cttccaacta ctacaaatct acaaatgtgg actttgctgt caatactgag    2160
ggtacttatt ccgagcctcg ccccattggc acccgttacc tcacccgtaa tctgtaa      2217
```

UNITED STATES PATENT AND TRADEMARK OFFICE
CERTIFICATE OF CORRECTION

PATENT NO. : 9,840,719 B2
APPLICATION NO. : 14/338200
DATED : December 12, 2017
INVENTOR(S) : Katherine High et al.

It is certified that error appears in the above-identified patent and that said Letters Patent is hereby corrected as shown below:

In the Specification

At Column 41, Line 12, please replace the "leucine" with "valine"

Signed and Sealed this
Sixth Day of November, 2018

Andrei Iancu
*Director of the United States Patent and Trademark Office*